United States Patent
Keravala et al.

(10) Patent No.: US 10,703,797 B2
(45) Date of Patent: Jul. 7, 2020

(54) GENE THERAPY VECTORS FOR TREATMENT OF DANON DISEASE

(71) Applicant: Rocket Pharmaceuticals, Ltd., New York, NY (US)

(72) Inventors: Annahita Keravala, New York, NY (US); Simon Moore, New York, NY (US); David Ricks, New York, NY (US)

(73) Assignee: Rocket Pharmaceuticals, Ltd., New York, NY (US)

( * ) Notice: Subject to any disclaimer, the term of this patent is extended or adjusted under 35 U.S.C. 154(b) by 0 days.

(21) Appl. No.: 16/729,002

(22) Filed: Dec. 27, 2019

(65) Prior Publication Data

US 2020/0148745 A1    May 14, 2020

Related U.S. Application Data

(63) Continuation of application No. PCT/US2019/041465, filed on Jul. 11, 2019.

(60) Provisional application No. 62/697,302, filed on Jul. 12, 2018.

(51) Int. Cl.
| | | |
|---|---|---|
| C07K 14/705 | (2006.01) | |
| A61P 21/00 | (2006.01) | |
| C12N 15/86 | (2006.01) | |
| A61P 9/00 | (2006.01) | |
| A61K 38/00 | (2006.01) | |

(52) U.S. Cl.
CPC .......... *C07K 14/70596* (2013.01); *A61P 9/00* (2018.01); *A61P 21/00* (2018.01); *C12N 15/86* (2013.01); *A61K 38/00* (2013.01); *C12N 2799/022* (2013.01); *C12N 2799/04* (2013.01); *C12N 2810/85* (2013.01); *C12N 2830/001* (2013.01); *C12N 2830/008* (2013.01)

(58) Field of Classification Search
CPC ...... C07K 14/70596; A61P 21/00; A61P 9/00; C12N 15/86; C12N 2799/022; C12N 2799/04; C12N 2810/85; C12N 2830/001; C12N 2830/008; A61K 38/00
See application file for complete search history.

(56) References Cited

U.S. PATENT DOCUMENTS

| | | |
|---|---|---|
| 5,139,941 A | 8/1992 | Muzycka et al. |
| 5,173,414 A | 12/1992 | Lebkowski et al. |
| 8,796,236 B2 | 8/2014 | Dodge et al. |
| 2004/0053870 A1 | 3/2004 | Yew et al. |
| 2010/0183577 A1 | 7/2010 | Stern et al. |
| 2010/0284990 A1 | 11/2010 | Kaemmerer et al. |
| 2013/0184223 A1 | 7/2013 | Land et al. |
| 2014/0112896 A1 | 4/2014 | Rebar |
| 2015/0273016 A1 | 10/2015 | Parenti et al. |
| 2016/0060656 A1 | 3/2016 | Rebar |
| 2019/0054190 A1 | 2/2019 | Adler et al. |

FOREIGN PATENT DOCUMENTS

| | | |
|---|---|---|
| WO | WO-92/001070 A1 | 3/1993 |
| WO | WO-93/03769 A1 | 3/1993 |
| WO | WO-2004/048537 A2 | 6/2004 |
| WO | WO-2004/048537 A3 | 6/2004 |
| WO | WO-2017/127565 A1 | 7/2017 |

OTHER PUBLICATIONS

Adler, E. et al. (2019). "AAV9.LAMP-2B improves metabolic and physiologic function in murine and human in-vitro models of Danon disease," JACC, Mar. 12, 2019, vol. 73, Issue 9, 1 total page.
Brown, H.C. et al. (2018). "Target-cell directed bioengineering approaches for gene therapy of Hemophilia A," Mol. Ther. Methods Clin. Dev. 9:57-69.
Cearley, C.N. et al. (2008). "Expanded repertoire of AAV vector serotypes mediate unique patterns of transduction in mouse brain," Mol. Ther.16:1710-1718.
Chandler, R.J. et al. (2017). Systemic AAV9 gene therapy improves the lifespan of mice with Niemann-Pick disease, type C1, Human Mol. Genetics 27:52-64.
Cuervo, A.M. et al. (2000). "Unique properties of lamp2a compared to other lamp2 isoforms," Journal of Cell Science 113:4441-4450.
D'Souza, R.S. et al. (2014). "Danon Disease—Clinical features, evaluation, and management," Circ. Heart Failure 7:843-849.
Extended European Search Report dated Jul. 26, 2019, for EP application No. 17 741 940.5, filed on Jan. 19, 2017, 5 pages.
Franco, L.M. et al. (2005). "Evasion of immune response to introduced human acid α-Glucosidase by liver-restricted expression in Glycogen storage disease Type II," Mol. Therapy 12:876-884.
Hashem, S.I. et al. (2015). "Brief report: Oxidative stress mediates cardiomyocyte apoptosis in a human model of Danon disease and heart failure," *Stem Cells* 33:2343-2350.
Ioannou Y.A et al. (2003). "Gene Therapy for Lysosomal Storage Disorders," Expert Opin. Biol. Ther. 3:789-801.
International Search Report dated Oct. 28, 2019, for PCT application No. PCT/US2019/041465, filed on Jul. 11, 2019, 5 pages.
International Search Report dated Apr. 4, 2017, for PCT application No. PCT/US2017/014164, filed on Jan. 19, 2017, 4 pages.
Stypmann, J. et al. (2006). "LAMP-2 deficient mice show depressed cardiac contractile function without significant changes in calcium handling," Basic. Res. Cardiol. 101:281-291.
Su, C. et al. (2016). "Geniposide reduces α-synuclein by blocking microRNA-21/lysosome-associated membrane protein 2A interaction in Parkinson disease models," Brain Res. 1644:98-106.
Sun, B-D. et al. (2003). "Long-term correction of glycogen storage disease type II with a hybrid Ad-AAV vector," Mol. Ther. 7:193-201.

(Continued)

*Primary Examiner* — Thaian N. Ton
(74) *Attorney, Agent, or Firm* — Cooley LLP

(57) ABSTRACT

The disclosure relates to optimized polynucleotide sequences for LAMP-2B, expression cassettes, vectors, and methods of use thereof in treating disease, e.g. Danon disease.

15 Claims, 19 Drawing Sheets

Specification includes a Sequence Listing.

(56) References Cited

OTHER PUBLICATIONS

Tanaka, Y. et al. (2000). "Accumulation of autophagic vacuoles and cardiomyopathy in LAMP-2-deficient mice," *Nature* 406:902-906.
Written Opinion of the International Searching Authority dated Oct. 28, 2019, for PCT application No. PCT/US2019/041465, filed on Jul. 11, 2019, 6 pages.
Written Opinion of the International Searching Authority dated Apr. 4, 2017, for PCT application No. PCT/US2017/014164, filed on Jan. 19, 2017, 5 pages.
Zhou, D. et al. (2005). "Lamp-2a Facilitates MHC Class II Presentation of Cytoplasmic Antigens," *Immunity* 22:571-581.
Danon, M. J. et al. (1981). "Lysosomal glycogen storage disease with normal acid maltase," *Neurology* 31:51-57.
Fu, H. et al. (2011). "Correction of neurological disease of Mucopolysaccharidosis IIIB in adult mice by rAAV9 trans-blood-brain barrier gene delivery," *Mol. Therapy* 19:1025-1033.
Gray, S.J. et al. (2011). "Preclinical differences of intravascular AAV9 delivery to neurons and glia: A comparative study of adult mice and nonhuman primates," *Mol. Therapy* 19:1058-1069.
Inagaki, K. et al. (2006). "Robust systemic transduction with AAV9 vectors in mice: Efficient global cardiac gene transfer superior to that of AAV8," *Mol. Therapy* 14:45-53.
Jackson, K.L. et al. (2016). "Corrigendum: Better targeting, better efficiency for wide-scale neuronal transduction with the Synapsin promoter and AAV-PHP.B," *Front. Mol. Neurosci.* 9:1.
Nishino, I. et al. (2000). "Primary LAMP-2 deficiency causes X-linked vacuolar cardiomyopathy and myopathy (Danon disease)," *Nature* 406(6798):902-926.
Ruzo, A. et al. (2012). "Correction of pathological accumulation of glycosaminoglycans in central nervous system and peripheral tissues of MPSIIIA mice through systemic AAV9 gene transfer," *Human Gene Ther.* 23:1237-1246.
Strausberg—GenBank BC002965 (2002). *Homo sapiens* lysosomal-associated membrane protein 2, mRNA (cDNA clone MGC: 1710 image:3543019), complete cds, 3 total pages.
Weismann, C.M. et al. (2015). "Systemic AAV9 gene transfer in adult GM1 gangliosidosis mice reduces lysosomal storage in CNS and extends lifespan," *Human Molecular Genetics* 24:4353-4364.

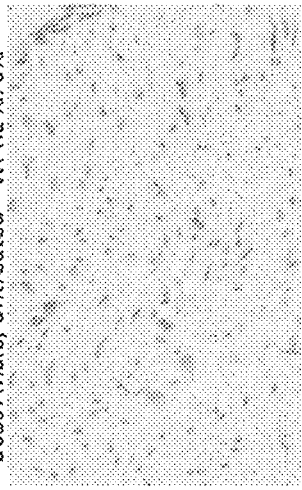
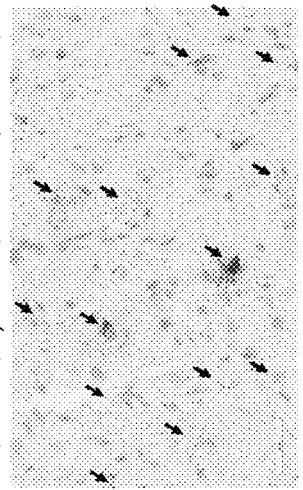
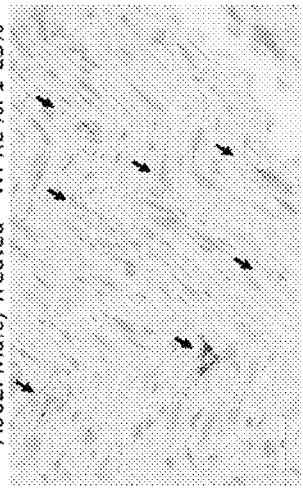

↙ Indicate mRNA staining

FIG. 10F

| Animal | Tissue | Location | Treatment | % Expressing Cells |
|---|---|---|---|---|
| B059 | Heart | left ventricle | Untreated | 0% |
| B059 | Muscle | quadricep | Untreated | 0% |
| B059 | Liver | left lobe | Untreated | 0% |
| A991 | Heart | left ventricle | Treated | 26-50% |
| A991 | Heart | right ventricle | Treated | 26-50% |
| A991 | Heart | left atrium | Treated | 1-25% |
| A991 | Heart | right atrium | Treated | 26-50% |
| A991 | Muscle | quadricep | Treated | 0% |
| A991 | Muscle | gastrocnemius | Treated | 0% |
| A991 | Liver | left lobe | Treated | 26-50% |
| A991 | Liver | right lobe | Treated | 51-75% |
| A602 | Heart | left ventricle | Treated | 1-25% |
| A602 | Heart | right ventricle | Treated | 1-25% |
| A602 | Heart | left atrium | Treated | 26-50% |
| A602 | Heart | right atrium | Treated | 1-25% |
| A602 | Muscle | quadricep | Treated | 1-25% |
| A602 | Muscle | gastrocnemius | Treated | 1-25% |
| A602 | Liver | left lobe | Treated | 51-75% |
| A602 | Liver | right lobe | Treated | 51-75% |

FIG. 10E

SEQUENCE LISTING

<160> NUMBER OF SEQ ID NOS: 38

<210> SEQ ID NO 1
<211> LENGTH: 409
<212> TYPE: PRT
<213> ORGANISM: Homo sapiens

<400> SEQUENCE: 1

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu Glu Leu Asn
            20                  25                  30

Leu Thr Asp Ser Glu Asn Ala Thr Cys Leu Tyr Ala Lys Trp Gln Met
        35                  40                  45

Asn Phe Thr Val Arg Tyr Glu Thr Thr Asn Lys Thr Tyr Lys Thr Val
    50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95

Ser Trp Ile Ala Asn Phe Thr Lys Ala Ala Ser Thr Tyr Ser Ile Asp
            100                 105                 110

Ser Val Ser Phe Ser Tyr Asn Thr Gly Asp Asn Thr Thr Phe Pro Asp
        115                 120                 125

Ala Glu Asp Lys Gly Ile Leu Thr Val Asp Glu Leu Leu Ala Ile Arg
    130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
            180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Ile Ser Met Tyr
    290                 295                 300

Leu Val Asn Gly Ser Val Phe Ser Ile Ala Asn Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Gln Glu Cys
        355                 360                 365

```
Ser Leu Asp Asp Asp Thr Ile Leu Ile Pro Ile Ile Val Gly Ala Gly
    370                 375                 380

Leu Ser Gly Leu Ile Ile Val Ile Val Ile Ala Tyr Val Ile Gly Arg
385                 390                 395                 400

Arg Lys Ser Tyr Ala Gly Tyr Gln Thr
                405
```

<210> SEQ ID NO 2
<211> LENGTH: 1233
<212> TYPE: DNA
<213> ORGANISM: Homo sapiens

<400> SEQUENCE: 2

| | | | | | |
|---|---|---|---|---|---|
| atggtgtgct | tccgcctctt | cccggttccg | ggctcagggc | tcgttctggt | ctgcctagtc | 60 |
| ctgggagctg | tgcggtctta | tgcattggaa | cttaatttga | cagattcaga | aaatgccact | 120 |
| tgcctttatg | caaaatggca | gatgaatttc | acagttcgct | atgaaactac | aaataaaact | 180 |
| tataaaactg | taaccatttc | agaccatggc | actgtgacat | ataatggaag | catttgtggg | 240 |
| gatgatcaga | atggtcccaa | aatagcagtg | cagttcggac | ctggctttc | ctggattgcg | 300 |
| aattttacca | aggcagcatc | tacttattca | attgacagcg | tctcattttc | ctacaacact | 360 |
| ggtgataaca | acacatttcc | tgatgctgaa | gataaggaa | ttcttactgt | tgatgaactt | 420 |
| ttggccatca | gaattccatt | gaatgacctt | tttagatgca | atagtttatc | aactttggaa | 480 |
| aagaatgatg | ttgtccaaca | ctactgggat | gttcttgtac | aagcttttgt | ccaaaatggc | 540 |
| acagtgagca | caaatgagtt | cctgtgtgat | aaagacaaaa | cttcaacagt | ggcacccacc | 600 |
| atacacacca | ctgtgccatc | tcctactaca | acacctactc | caaggaaaa | accagaagct | 660 |
| ggaacctatt | cagttaataa | tggcaatgat | acttgtctgc | tggctaccat | ggggctgcag | 720 |
| ctgaacatca | ctcaggataa | ggttgcttca | gttattaaca | tcaaccccaa | tacaactcac | 780 |
| tccacaggca | gctgccgttc | tcacactgct | ctacttagac | tcaatagcag | caccattaag | 840 |
| tatctagact | ttgtctttgc | tgtgaaaaat | gaaaaccgat | tttatctgaa | ggaagtgaac | 900 |
| atcagcatgt | atttggttaa | tggctccgtt | tcagcattg | caaataacaa | tctcagctac | 960 |
| tgggatgccc | cctgggaag | ttcttatatg | tgcaacaaag | agcagactgt | ttcagtgtct | 1020 |
| ggagcatttc | agataaaatac | ctttgatcta | agggttcagc | ctttcaatgt | gacacaagga | 1080 |
| aagtattcta | cagcccaaga | gtgttcgctg | gatgatgaca | ccattctaat | cccaattata | 1140 |
| gttggtgctg | gtcttttcagg | cttgattatc | gttatagtga | ttgcttacgt | aattggcaga | 1200 |
| agaaaaagtt | atgctggata | tcagactctg | taa | | | 1233 |

<210> SEQ ID NO 3
<211> LENGTH: 1233
<212> TYPE: DNA
<213> ORGANISM: Artificial Sequence
<220> FEATURE:
<223> OTHER INFORMATION: variant of LAMP-2

<400> SEQUENCE: 3

| | | | | | |
|---|---|---|---|---|---|
| atggtctgct | tcagactgtt | ccctgtccct | ggatctggtc | tggtgcttgt | gtgcttggtg | 60 |
| ctgggtgctg | tgagatccta | tgcccttgag | ctgaacctga | ctgactcaga | aaatgccact | 120 |
| tgcctgtatg | ccaagtggca | gatgaacttc | actgtgagat | atgagactac | caacaagacc | 180 |
| tacaagactg | tgaccatctc | agaccatggc | actgtcacct | acaatggatc | aatctgtggt | 240 |
| gatgatcaga | atggcccaaa | gatagcagtg | cagtttgggc | ccggtttttc | ctggattgct | 300 |

| | |
|---|---|
| aacttcacca aggcagcctc cacctacagc attgactcag tcagcttcag ctacaacact | 360 |
| ggggataaca ccaccttccc tgacgcagag gacaagggaa tccttactgt ggacgaactc | 420 |
| ctggcaatca gaatccccct taacgacctg ttcagatgca actcccttc aacccttgaa | 480 |
| aagaatgatg tggtgcaaca ctattgggac gtcctggtgc aagcctttgt gcagaatggg | 540 |
| acagtgagta ccaacgagtt cctctgtgac aaggacaaga ccagcactgt ggcccccact | 600 |
| atccacacca ctgtgcccag ccctaccact accccaccc ctaaagagaa gccagaagct | 660 |
| ggaacctact cagtcaacaa tggaaatgac acatgcctcc ttgccaccat gggactgcag | 720 |
| ctgaacatca ctcaggacaa ggtggcctca gtgattaaca tcaaccctaa caccactcat | 780 |
| agcactggga gctgcagatc acatacagct ctgctgaggc tcaactcctc caccatcaag | 840 |
| tacctggact ttgtgtttgc tgtgaagaat gagaacaggt tctacctcaa ggaagtgaac | 900 |
| atttccatgt acctggtcaa tggttcagtg ttctctattg ccaacaacaa tctgagctac | 960 |
| tgggatgcac ccctgggatc ctcctacatg tgcaacaagg agcagactgt gagtgtgtca | 1020 |
| ggtgcttttc agatcaacac ttttgacctg agggtgcagc ccttcaatgt gactcaggga | 1080 |
| aagtactcca ctgcacaaga gtgttccttg gatgatgaca ctatcctcat ccccattatt | 1140 |
| gtgggagctg gactgtcagg attgattata gtgattgtga ttgcttatgt gattggaagg | 1200 |
| agaaagagct atgctggcta ccagaccctg taa | 1233 |

<210> SEQ ID NO 4
<211> LENGTH: 1233
<212> TYPE: DNA
<213> ORGANISM: Artificial Sequence
<220> FEATURE:
<223> OTHER INFORMATION: variant of LAMP-2

<400> SEQUENCE: 4

| | |
|---|---|
| atggtgtgct ttagactgtt tcctgtgcct ggttcagggc tggtcctggt ctgtctggtg | 60 |
| ctgggggctg tcagaagcta tgccttggag ctgaacctca ctgatagtga aaatgccact | 120 |
| tgtctgtatg ctaagtggca gatgaacttc actgtgagat atgaaaccac caacaagact | 180 |
| tacaaaacag tgaccatctc agatcatgga actgtgacct acaacggcag catttgtgga | 240 |
| gacgaccaga acggaccaaa aatcgctgtc caatttgggc ctggattctc ctggattgcc | 300 |
| aatttcacta aagctgcctc cacatattca attgactcag tgtccttctc ctacaacact | 360 |
| ggggacaaca ctactttccc tgatgctgaa gataagggaa tcttgacagt ggatgagctg | 420 |
| ctggctatca ggatcccttt gaatgacctg tttaggtgta ttcactgag cactctggag | 480 |
| aagaacgacg tggtgcagca ctactgggac gtgctggtgc aggcctttgt gcagaacggc | 540 |
| actgtgtcca ccaacgaatt cctgtgtgat aaggacaaaa cttccactgt ggcacctaca | 600 |
| attcacacta ctgtgccttc acctaccacc actccaactc caaaggaaaa gcctgaagca | 660 |
| ggaacctact ctgtgaacaa tggcaatgat acctgtctgt ggccaccat gggcctccaa | 720 |
| ctgaacatta ctcaggacaa ggtggcctca gtgattaaca ttaaccccaa cactacccac | 780 |
| tccactggca gctgtagatc acacacagcc ttgctcagac tgaatagcag caccatcaag | 840 |
| tatttggatt ttgtgtttgc agtgaagaat gaaaacaggt tctacctcaa ggaagtcaac | 900 |
| atctcaatgt acctggtgaa cggctcagtg ttcagcattg ccaacaacaa cctctcctat | 960 |
| tgggacgctc cactggggag cagctacatg tgtaacaagg aacagactgt gtcagtgtca | 1020 |
| ggagccttcc agattaacac ctttgatctg agggtccaac cctttaatgt cactcaagga | 1080 |
| aagtatagca ctgcccagga gtgctccctg gatgatgaca ccattctgat tccaatcatt | 1140 |

```
gtgggtgcag gactttctgg gcttattatt gtgattgtga ttgcctatgt gattggcaga 1200
aggaaatcct atgcagggta ccaaactctg taa 1233

<210> SEQ ID NO 5
<211> LENGTH: 1233
<212> TYPE: DNA
<213> ORGANISM: Artificial Sequence
<220> FEATURE:
<223> OTHER INFORMATION: variant of LAMP-2

<400> SEQUENCE: 5
atggtctgtt ttaggctgtt ccctgtccct ggttcaggac tggtcttagt gtgtctggtg 60
cttggagctg tcagaagcta tgccctggag ctgaacctga ctgactcaga aaatgccact 120
tgcctgtatg ccaagtggca gatgaacttc actgtcagat atgaaaccac caacaagacc 180
tataagactg tgaccatctc agaccatggc actgtgactt acaatgggtc aatttgtgga 240
gatgaccaga atggccctaa gatagctgtc cagtttggtc caggattcag ctggattgcc 300
```

```
aacttcacca aggcagccag cacctacagc attgactctg tgtccttctc ctacaacaca 360
ggagacaaca ccactttccc tgatgcagag gacaaaggta tcctgactgt ggatgagttg 420
ctggcaatca ggatcccact gaacgatctg ttcaggtgca actcactgtc cactctggaa 480
aagaatgatg tggtgcagca ctattgggat gtgctagtcc aggcctttgt ccagaatggg 540
actgtgtcaa ctaatgagtt cctgtgtgac aaggacaaga caagcactgt agccccccact 600
atccatacca cagtacctag ccccaccact actccaaccc ccaaggagaa gcctgaggct 660
ggcacctact cagtgaacaa tggaatgac acctgtttgc tggccactat gggactccaa 720
ctgaacatca cccaggacaa agtggcctct gtgatcaata tcaatcccaa caccacccac 780
agcactgggt cctgcagaag ccacactgcc ctcctgaggc tcaactcatc aactatcaag 840
tacttggatt ttgtgtttgc agtgaagaat gagaacagat tctacctcaa agaggtcaac 900
atttcaatgt acctggtgaa tgggagtgtg ttctccattg ctaacaacaa cctgagctac 960
tgggatgccc ctctgggctc ctcatacatg tgcaacaagg aacagactgt gagtgtgtca 1020
ggggccttcc agatcaacac ttttgacctg agagtgcagc cctttaatgt gacacaggga 1080
aagtacagca ctgctcagga gtgcagcctg gatgatgaca ctatcctgat ccctatcatt 1140
gtgggggcag gcctgtctgg actcattatt gtgattgtga ttgcctatgt gatagggaga 1200
aggaagtctt atgctggata ccagaccctg taa 1233

<210> SEQ ID NO 6
<211> LENGTH: 13
<212> TYPE: DNA
<213> ORGANISM: Unknown
<220> FEATURE:
<223> OTHER INFORMATION: Kozak sequence

<400> SEQUENCE: 6
gccgccacca tgg 13

<210> SEQ ID NO 7
<211> LENGTH: 387
<212> TYPE: DNA
<213> ORGANISM: Unknown
<220> FEATURE:
<223> OTHER INFORMATION: full-length polyA sequence

<400> SEQUENCE: 7
```

| | |
|---|---|
| tggctaataa aggaaattta ttttcattgc aatagtgtgt tggaattttt tgtgtctctc | 60 |
| actcggaagg acatatggga gggcaaatca tttaaaacat cagaatgagt atttggttta | 120 |
| gagtttggca acatatgccc atatgctggc tgccatgaac aaaggttggc tataaagagg | 180 |
| tcatcagtat atgaaacagc ccctgctgt ccattcctta ttccatagaa aagccttgac | 240 |
| ttgaggttag attttttta tattttgttt tgtgttattt ttttctttaa catccctaaa | 300 |
| attttcctta catgttttac tagccagatt tttcctcctc cctgactac tcccagtcat | 360 |
| agctgtccct cttctcttat ggagatc | 387 |

<210> SEQ ID NO 8
<211> LENGTH: 4549
<212> TYPE: DNA
<213> ORGANISM: Artificial Sequence
<220> FEATURE:
<223> OTHER INFORMATION: expression cassette

<400> SEQUENCE: 8

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| aggggttcct tgtagttaat gattaacccg ccatgctact tatctaccag ggtaatgggg | 180 |
| atcctctaga actatagcta gtcgacattg attattgact agttattaat agtaatcaat | 240 |
| tacggggtca ttagttcata gcccatatat ggagttccgc gttacataac ttacggtaaa | 300 |
| tggcccgcct ggctgaccgc ccaacgaccc cgcccattg acgtcaataa tgacgtatgt | 360 |
| tcccatagta acgccaatag ggactttcca ttgacgtcaa tgggtggagt atttacggta | 420 |
| aactgcccac ttggcagtac atcaagtgta tcatatgcca agtacgcccc ctattgacgt | 480 |
| caatgacggt aaatggcccg cctggcatta tgcccagtac atgaccttat gggactttcc | 540 |
| tacttggcag tacatctacg tattagtcat cgctattacc atggtcgagg tgagccccac | 600 |
| gttctgcttc actctcccca tctccccccc ctccccaccc ccaattttgt atttatttat | 660 |
| tttttaatta ttttgtgcag cgatggggc gggggggggg ggggggcgcg cgccaggcgg | 720 |
| ggcggggcgg ggcgaggggc ggggcgggc gaggcggaga ggtgcggcgg cagccaatca | 780 |
| gagcggcgcg ctccgaaagt ttccttttat ggcgaggcgg cggcggcggc ggccctataa | 840 |
| aaagcgaagc gcgcggcggg cgggagtcgc tgcgcgctgc cttcgccccg tgccccgctc | 900 |
| cgccgccgcc tcgcgccgcc cgccccggct ctgactgacc gcgttactcc cacaggtgag | 960 |
| cgggcgggac ggcccttctc ctccgggctg taattagcgc ttggtttaat gacggcttgt | 1020 |
| ttcttttctg tggctgcgtg aaagccttga ggggctccgg gagggccctt tgtgcggggg | 1080 |
| gagcggctcg gggggtgcgt gcgtgtgtgt gtgcgtgggg agcgccgcgt gcggctccgc | 1140 |
| gctgcccggc ggctgtgagc gctgcgggcg cggcgcgggg ctttgtgcgc tccgcagtgt | 1200 |
| gcgcgagggg agcgcggccg ggggcggtgc cccgcggtgc ggggggggct gcgaggggaa | 1260 |
| caaaggctgc gtgcggggtg tgtgcgtggg ggggtgagca ggggtgtgg gcgcgtcggt | 1320 |
| cgggctgcaa ccccccctgc acccccctcc ccgagttgct gagcacggcc cggcttcggg | 1380 |
| tgcgggctc cgtacggggc gtggcgcggg gctcgccgtg ccgggcgggg ggtgcggca | 1440 |
| ggtgggggtg ccgggcgggg cggggccgcc tcgggccggg gagggctcgg ggaggggcg | 1500 |
| cggcggcccc cggagcgccg cgcggctgtc g aggcgcggcg agccgcagcc attgccttt | 1560 |
| atggtaatcg tgcgagaggg cgcagggact tcctttgtcc caaatctgtg cggagccgaa | 1620 |
| atctgggagg cgccgccgca cccccctctag cgggcgcggg gcgaagcggt gcggcgccgg | 1680 |

```
caggaaggaa atgggcgggg agggccttcg tgcgtcgccg cgccgccgtc cccttctccc    1740
tctccagcct cggggctgtc cgcgggggga cggctgcctt cggggggggac ggggcagggc    1800 ggggttcggc ttctggcgtg tgaccggcgg ctctagagcc tctgctaacc atgttcatgc    1860
cttcttcttt ttcctacagc tcctgggcaa cgtgctggtt attgtgctgt ctcatcattt    1920
tggcaaagaa ttcgagcggc cgccagccgc caccatggtc tgcttcagac tgttccctgt    1980
ccctggatct ggtctggtgc ttgtgtgctt ggtgctgggt gctgtgagat cctatgccct    2040
tgagctgaac ctgactgact cagaaaatgc cacttgcctg tatgccaagt ggcagatgaa    2100
cttcactgtg agatatgaga ctaccaacaa gacctacaag actgtgacca tctcagacca    2160
tggcactgtc acctacaatg gatcaatctg tggtgatgat cagaatggcc aaagatagc    2220 agtgcagttt gggcccggtt tttcctggat tgctaacttc accaaggcag cctccaccta    2280
cagcattgac tcagtcagct tcagctacaa cactggggat aacaccacct tccctgacgc    2340
agaggacaag ggaatcctta ctgtggacga actcctggca atcagaatcc cccttaacga    2400
cctgttcaga tgcaactccc tttcaaccct tgaaaagaat gatgtggtgc aacactattg    2460
ggacgtcctg gtgcaagcct tgtgcagaaa tgggacagtg agtaccaacg agttcctctg    2520
tgacaaggac aagaccagca ctgtggcccc cactatccac accactgtgc ccagccctac    2580
cactaccccc acccctaaag agaagccaga agctggaacc tactcagtca acaatggaaa    2640
tgacacatgc ctccttgcca ccatgggact gcagctgaac atcactcagg acaaggtggc    2700
ctcagtgatt aacatcaacc ctaacaccac tcatagcact gggagctgca gatcacatac    2760
agctctgctg aggctcaact cctccaccat caagtacctg actttgtgt tgctgtgaa    2820 gaatgagaac aggttctacc tcaaggaagt gaacatttcc atgtacctgg tcaatggttc    2880
agtgttctct attgccaaca caatctgag ctactgggat gcacccctgg atcctccta    2940 catgtgcaac aaggagcaga ctgtgagtgt gtcaggtgct tttcagatca acactttga    3000 cctgagggtg cagcccttca atgtgactca gggaaagtac tccactgcac aagagtgttc    3060
cttggatgat gacactatcc tcatccccat tattgtggga gctggactgt caggattgat    3120
tatagtgatt gtgattgctt atgtgattgg aaggagaaag agctatgctg gctaccagac    3180
cctgtaaaag ggcgaattcc agcacacgcg tcctaggagc tcgagtacta ctggcggccg    3240
ttactagtgg atccgcggta caagtaagca tgcaagcttc gaggacgggg tgaactacgc    3300
ctgaatcaag cttatcgata aattcgagca tcttaccgcc atttattccc atatttgttc    3360
tgtttttctt gatttgggta tacatttaaa tgttaataaa acaaaatggt ggggcaatca    3420
tttacatttt tagggatatg taattactag ttcaggtgta ttgccacaag acaaacatgt    3480
taagaaactt tcccgttatt tacgctctgt tcctgttaat caacctctgg attacaaaat    3540
ttgtgaaaga ttgactgata ttcttaacta tgttgctcct tttacgctgt gtggatatgc    3600
tgctttaatg cctctgtatc atgctattgc ttcccgtacg gctttcgttt tctcctcctt    3660
gtataaatcc tggttgctgt ctctttatga ggagttgtgg cccgttgtcc gtcaacgtgg    3720
cgtggtgtgc tctgtgtttg ctgacgcaac ccccactggc tggggcattg ccaccacctg    3780
tcaactcctt tctgggactt tcgctttccc cctcccgatc gccacggcag aactcatcgc    3840
cgcctgcctt gcccgctgct ggacagggc taggttgctg gcactgata attccgtggt    3900 gttgtcgggg aagggcctcg ataccgtcga tatcgatcct ggctaataaa ggaaatttat    3960
tttcattgca atagtgtgtt ggaatttttt gtgtctctca ctcggaagga catatgggag    4020
```

```
ggcaaatcat ttaaaacatc agaatgagta tttggtttag agtttggcaa catatgccca    4080
tatgctggct gccatgaaca aaggttggct ataaagaggt catcagtata tgaaacagcc    4140
ccctgctgtc cattccttat tccatagaaa agccttgact tgaggttaga ttttttttat    4200
attttgtttt gtgttatttt tttctttaac atccctaaaa ttttccttac atgttttact    4260
agccagattt ttcctcctct cctgactact cccagtcata gctgtccctc ttctcttatg    4320
gagatcgaag caattcgttg atctgaattt cgaccaccca taatagatct cccattaccc    4380
tggtagataa gtagcatggc gggttaatca ttaactacaa ggaacccta gtgatggagt     4440 tggccactcc ctctctgcgc gctcgctcgc tcactgaggc cgggcgacca aaggtcgccc    4500
gacgcccggg ctttgcccgg cggcctcag tgagcgagcg agcgcgcag               4549

<210> SEQ ID NO 9
<211> LENGTH: 4549
<212> TYPE: DNA
<213> ORGANISM: Artificial Sequence
<220> FEATURE:
<223> OTHER INFORMATION: expression cassette

<400> SEQUENCE: 9
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct tgtagttaat gattaacccg ccatgctact tatctaccag ggtaatgggg    180
atcctctaga actatagcta gtcgacattg attattgact agttattaat agtaatcaat    240
tacggggtca ttagttcata gcccatatat ggagttccgc gttacataac ttacggtaaa    300
tggcccgcct ggctgaccgc ccaacgaccc ccgcccattg acgtcaataa tgacgtatgt    360
tcccatagta acgccaatag ggactttcca ttgacgtcaa tgggtggagt atttacggta    420
aactgcccac ttggcagtac atcaagtgta tcatatgcca agtacgcccc ctattgacgt    480
caatgacggt aaatggcccg cctggcatta tgcccagtac atgaccttat gggactttcc    540
tacttggcag tacatctacg tattagtcat cgctattacc atggtcgagg tgagccccac    600
gttctgcttc actctcccca tctcccccccc ctccccaccc caatttttgt atttatttat    660
tttttaatta ttttgtgcag cgatgggggc ggggggggggg ggggcgcg cgccaggcgg     720 ggcggggcgg ggcgaggggc ggggcgggc gaggcggaga ggtgcggcgg cagccaatca    780
gagcggcgcg ctccgaaagt ttccttttat ggcgaggcgg cggcggcggc ggccctataa    840
aaagcgaagc gcgcggcggg cgggagtcgc tgcgcgctgc cttcgcccg tgccccgctc    900 cgccgccgcc tcgcgccgcc cgccccggct ctgactgacc gcgttactcc cacaggtgag    960
cgggcgggac ggcccttctc ctccgggctg taattagcgc ttggtttaat gacggcttgt    1020
ttcttttctg tggctgcgtg aaagccttga ggggctccgg gagggccctt tgtgcggggg    1080
gagcggctcg ggggtgcgt gcgtgtgtgt gtgcgtgggg agcgccgcgt gcggctccgc    1140
gctgcccggc ggctgtgagc gctgcgggcg cggcgcgggg ctttgtgcgc tccgcagtgt    1200
gcgcgagggg agcgcggccg ggggcggtgc cccgcggtgc gggggggggct gcgaggggaa    1260 caaaggctgc gtgcggggtg tgtgcgtggg gggtgagca ggggtgtgg gcgcgtcggt     1320 cgggctgcaa ccccccctgc acccccctcc ccgagttgct gagcacggcc cggcttcggg    1380
tgcggggctc cgtacggggc gtggcgcggg gctcgccgtg ccgggcgggg ggtggcggca    1440
ggtgggggtg ccgggcgggg cggggccgcc tcggccgggg gagggctcgg gggaggggcg    1500
cggcggcccc cggagcgccg gcggctgtcg aggcgcggcg agccgcagcc attgccttt     1560
```

```
atggtaatcg tgcgagaggg cgcagggact tcctttgtcc caaatctgtg cggagccgaa    1620
atctgggagg cgccgccgca cccctctag cgggcgcggg gcgaagcggt gcggcgccgg     1680
caggaaggaa atgggcgggg agggccttcg tgcgtcgccg cgccgccgtc cccttctccc    1740
tctccagcct cggggctgtc cgcggggga cggctgcctt cggggggac ggggcagggc      1800 ggggttcggc ttctggcgtg tgaccggcgg ctctagagcc tctgctaacc atgttcatgc    1860
cttcttcttt ttcctacagc tcctgggcaa cgtgctggtt attgtgctgt ctcatcattt    1920
tggcaaagaa ttcgagcggc cgccagccgc caccatggtg tgctttagac tgtttcctgt    1980
gcctggttca gggctggtcc tggtctgtct ggtgctgggg gctgtcagaa gctatgcctt    2040
ggagctgaac ctcactgata gtgaaaatgc cacttgtctg tatgctaagt ggcagatgaa    2100
cttcactgtg agatatgaaa ccaccaacaa gacttacaaa acagtgacca tctcagatca    2160
tggaactgtg acctacaacg gcagcatttg tggagacgac cagaacggac aaaaatcgc    2220 tgtccaattt gggcctggat ctcctggat tgccaatttc actaaagctg cctccacata    2280
ttcaattgac tcagtgtcct tctcctacaa cactgggac aacactactt ccctgatgc      2340 tgaagataag ggaatcttga cagtggatga gctgctggct atcaggatcc ctttgaatga    2400
cctgttaggg tgtaattcac tgagcactct ggagaagaac gacgtggtgc agcactactg    2460
ggacgtgctg gtgcaggcct ttgtgcagaa cggcactgtg tccaccaacg aattcctgtg    2520
tgataaggac aaaacttcca ctgtggcacc tacaattcac actactgtgc cttcacctac    2580
caccactcca actccaaagg aaaagcctga agcaggaacc tactctgtga caatggcaa     2640 tgatacctgt ctgttggcca ccatgggcct ccaactgaac attactcagg acaaggtggc    2700
ctcagtgatt aacattaacc ccaacactac ccactccact ggcagctgta gatcacacac    2760
agccttgctc agactgaata gcagcaccat caagtatttg gattttgtgt ttgcagtgaa    2820
gaatgaaaac aggttctacc tgaaggaagt caacatctca atgtacctgg tgaacggctc    2880
agtgttcagc attgccaaca caacctctc ctattgggac gctccactgg ggagcagcta    2940
catgtgtaac aaggaacaga ctgtgtcagt gtcaggagcc ttccagatta acacctttga    3000
tctgagggtc caacccttta atgtcactca aggaaagtat agcactgccc aggagtgctc    3060
cctggatgat gacaccattc tgattccaat cattgtgggt gcaggacttt ctgggcttat    3120
tattgtgatt gtgattgcct atgtgattgg cagaaggaaa tcctatgcag ggtaccaaac    3180
tctgtaaaag ggcgaattcc agcacacgcg tcctaggagc tcgagtacta ctggcggccg    3240
ttactagtgg atccgcggta caagtaagca tgcaagcttc gaggacgggg tgaactacgc    3300
ctgaatcaag cttatcgata aattcgagca tcttaccgcc atttattccc atatttgttc    3360 tgttttctt gatttgggta tacatttaaa tgttaataaa acaaaatggt ggggcaatca    3420
tttacatttt tagggatatg taattactag ttcaggtgta ttgccacaag acaaacatgt    3480
taagaaactt tcccgttatt tacgctctgt tcctgttaat caacctctgg attacaaaat    3540
ttgtgaaaga ttgactgata ttcttaacta tgttgctcct tttacgctgt gtggatatgc    3600
tgctttaatg cctctgtatc atgctattgc ttcccgtacg gctttcgttt tctcctcctt    3660
gtataaatcc tggttgctgt ctctttatga ggagttgtgg cccgttgtcc gtcaacgtgg    3720
cgtggtgtgc tctgtgtttg ctgacgcaac ccccactggc tggggcattg ccaccacctg    3780
tcaactcctt tctgggactt tcgctttccc cctcccgatc gccacggcag aactcatcgc    3840
cgcctgcctt gcccgctgct ggacaggggc taggttgctg ggcactgata attccgtggt    3900
```

| | |
|---|---|
| gttgtcgggg aagggcctcg ataccgtcga tatcgatcct ggctaataaa ggaaatttat | 3960 |
| tttcattgca atagtgtgtt ggaattttt gtgtctctca ctcggaagga catatgggag | 4020 |
| ggcaaatcat ttaaaacatc agaatgagta tttggtttag agtttggcaa catatgccca | 4080 |
| tatgctggct gccatgaaca aaggttggct ataaagaggt catcagtata tgaaacagcc | 4140 |
| ccctgctgtc cattccttat tccatagaaa agccttgact tgaggttaga ttttttttat | 4200 |
| attttgtttt gtgttatttt tttctttaac atccctaaaa ttttccttac atgttttact | 4260 |
| agccagattt ttcctcctct cctgactact cccagtcata gctgtccctc ttctcttatg | 4320 |
| gagatcgaag caattcgttg atctgaattt cgaccaccca taatagatct cccattaccc | 4380 |
| tggtagataa gtagcatggc gggttaatca ttaactacaa ggaacccta gtgatggagt | 4440 |
| tggccactcc ctctctgcgc gctcgctcgc tcactgaggc cgggcgacca aaggtcgccc | 4500 |
| gacgcccggg ctttgcccgg gcggcctcag tgagcgagcg agcgcgcag | 4549 |

<210> SEQ ID NO 10
<211> LENGTH: 4549
<212> TYPE: DNA
<213> ORGANISM: Artificial Sequence
<220> FEATURE:
<223> OTHER INFORMATION: expression cassette

<400> SEQUENCE: 10

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| aggggttcct tgtagttaat gattaacccg ccatgctact tatctaccag ggtaatgggg | 180 |
| atcctctaga actatagcta gtcgacattg attattgact agttattaat agtaatcaat | 240 |
| tacggggtca ttagttcata gcccatatat ggagttccgc gttacataac ttacggtaaa | 300 |
| tggcccgcct ggctgaccgc ccaacgaccc ccgcccattg acgtcaataa tgacgtatgt | 360 |
| tcccatagta acgccaatag ggactttcca ttgacgtcaa tgggtggagt atttacggta | 420 |
| aactgcccac ttggcagtac atcaagtgta tcatatgcca agtacgcccc ctattgacgt | 480 |
| caatgacggt aaatggcccg cctggcatta tgcccagtac atgaccttat gggactttcc | 540 |
| tacttggcag tacatctacg tattagtcat cgctattacc atggtcgagg tgagccccac | 600 |
| gttctgcttc actctcccca tctcccccc ctccccaccc caatttgt atttattat | 660 |
| ttttaatta ttttgtgcag cgatgggggc gggggggggg ggggggcgcg cgccaggcgg | 720 |
| ggcggggcgg ggcgaggggc ggggcgggc gaggcggaga ggtgcggcgg cagccaatca | 780 |
| gagcggcgcg ctccgaaagt ttccttttat ggcgaggcgg cggcggcggc ggccctataa | 840 |
| aaagcgaagc gcgcggcggg cgggagtcgc tgcgcgctgc cttcgccccg tgccccgctc | 900 |
| cgccgccgcc tcgcgccgcc cgccccggct ctgactgacc gcgttactcc cacaggtgag | 960 |
| cgggcgggac ggcccttctc ctccgggctg taattagcgc ttggtttaat gacggcttgt | 1020 |
| ttcttttctg tggctgcgtg aaagccttga ggggctccgg gagggccctt tgtgcggggg | 1080 |
| gagcggctcg gggggtgcgt gcgtgtgtgt gtgcgtgggg agcgccgcgt gcggctccgc | 1140 |
| gctgcccggc ggctgtgagc gctgcgggcg cggcgcgggg ctttgtgcgc tccgcagtgt | 1200 |
| gcgcgagggg agcgcggccg ggggcggtgc cccgcggtgc gggggggct gcgaggggaa | 1260 |
| caaaggctgc gtgcggggtg tgtgcgtggg ggggtgagca gggggtgtgg gcgcgtcggt | 1320 |
| cgggctgcaa cccccctgc acccccctcc ccgagttgct gagcacggcc cggcttcggg | 1380 |
| tgcggggctc cgtacggggc gtggcgcggg gctcgccgtg ccgggcgggg ggtggcggca | 1440 |

```
ggtgggggtg  ccgggcgggg  cggggccgcc  tcgggccggg  gagggctcgg  ggggaggggcg   1500 cggcggcccc  cggagcgccg  gcggctgtcg  aggcgcggcg  agccgcagcc  attgccttt    1560 atggtaatcg  tgcgagaggg  cgcagggact  tcctttgtcc  caaatctgtg  cggagccgaa   1620
atctgggagg  cgccgccgca  cccccctctag cggggcgcgg  gcgaagcggt  gcggcgccgg   1680
caggaaggaa  atgggcgggg  agggccttcg  tgcgtcgccg  cgccgccgtc  cccttctccc   1740
tctccagcct  cggggctgtc  cgcggggggga cggctgcctt  cgggggggac  ggggcagggc   1800
ggggttcggc  ttctggcgtg  tgaccggcgg  ctctagagcc  tctgctaacc  atgttcatgc   1860
cttcttcttt  ttcctacagc  tcctgggcaa  cgtgctggtt  attgtgctgt  ctcatcattt   1920
tggcaaagaa  ttcgagcggc  cgccagccgc  caccatggtc  tgttttaggc  tgttccctgt   1980
ccctggttca  ggactggtct  tagtgtgtct  ggtgcttgga  gctgtcagaa  gctatgccct   2040
ggagctgaac  ctgactgact  cagaaaatgc  cacttgcctg  tatgccaagt  ggcagatgaa   2100
cttcactgtc  agatatgaaa  ccaccaacaa  gacctataag  actgtgacca  tctcagacca   2160
tggcactgtg  acttacaatg  ggtcaatttg  tggagatgac  cagaatggcc  ctaagatagc   2220
tgtccagttt  ggtccaggat  tcagctggat  tgccaacttc  accaaggcag  ccagcaccta   2280
cagcattgac  tctgtgtcct  tctcctacaa  cacaggagac  aacaccactt  tccctgatgc   2340
agaggacaaa  ggtatcctga  ctgtggatga  gttgctggca  atcaggatcc  cactgaacga   2400
tctgttcagg  tgcaactcac  tgtccactct  ggaaaagaat  gatgtggtgc  agcactattg   2460
ggatgtgcta  gtccaggcct  ttgtccagaa  tgggactgtg  tcaactaatg  agttcctgtg   2520
tgacaaggac  aagacaagca  ctgtagcccc  cactatccat  accacagtac  ctagccccac   2580
cactactcca  accccccaagg agaagcctga  ggctggcacc  tactcagtga  caatgggaa    2640 tgacacctgt  ttgctggcca  ctatgggact  ccaactgaac  atcacccagg  acaaagtggc   2700
ctctgtgatc  aatatcaatc  ccaacaccac  ccacagcact  gggtcctgca  gaagccacac   2760
tgccctcctg  aggctcaact  catcaactat  caagtacttg  gattttgtgt  ttgcagtgaa   2820
gaatgagaac  agattctacc  tcaaagaggt  caacatttca  atgtacctgg  tgaatgggag   2880
tgtgttctcc  attgctaaca  caaacctgag  ctactgggat  gcccctctgg  gctcctcata   2940
catgtgcaac  aaggaacaga  ctgtgagtgt  gtcaggggcc  ttccagatca  acacttttga   3000
cctgagagtg  cagcccttta  atgtgacaca  gggaaagtac  agcactgctc  aggagtgcag   3060
cctggatgat  gacactatcc  tgatccctat  cattgtgggg  gcaggcctgt  ctggactcat   3120
tattgtgatt  gtgattgcct  atgtgatagg  gagaaggaag  tcttatgctg  gataccagac   3180
cctgtaaaag  ggcgaattcc  agcacacgcg  tcctaggagc  tcgagtacta  ctggcggccg   3240
ttactagtgg  atccgcggta  caagtaagca  tgcaagcttc  gaggacgggg  tgaactacgc   3300
ctgaatcaag  cttatcgata  aattcgagca  tcttaccgcc  atttattccc  atatttgttc   3360 tgttttctt   gatttgggta  tacatttaaa  tgttaataaa  acaaaatggt  ggggcaatca   3420
tttacatttt  tagggatatg  taattactag  ttcaggtgta  ttgccacaag  acaaacatgt   3480
taagaaactt  tcccgttatt  tacgctctgt  tcctgttaat  caacctctgg  attacaaaat   3540
ttgtgaaaga  ttgactgata  ttcttaacta  tgttgctcct  tttacgctgt  gtggatatgc   3600
tgctttaatg  cctctgtatc  atgctattgc  ttcccgtacg  gctttcgttt  tctcctcctt   3660
gtataaatcc  tggttgctgt  ctctttatga  ggagttgtgg  cccgttgtcc  gtcaacgtgg   3720
cgtggtgtgc  tctgtgtttg  ctgacgcaac  ccccactggc  tggggcattg  ccaccacctg   3780
```

-continued

```
tcaactccttt tctgggactt tcgctttccc cctcccgatc gccacggcag aactcatcgc    3840
cgcctgcctt gcccgctgct ggacaggggc taggttgctg ggcactgata attccgtggt    3900
gttgtcgggg aagggcctcg ataccgtcga tatcgatcct ggctaataaa ggaaatttat    3960
tttcattgca atagtgtgtt ggaattttt gtgtctctca ctcggaagga catatgggag     4020
ggcaaatcat ttaaaacatc agaatgagta tttggtttag agtttggcaa catatgccca    4080
tatgctggct gccatgaaca aaggttggct ataaagaggt catcagtata tgaaacagcc    4140
ccctgctgtc cattccttat tccatagaaa agccttgact tgaggttaga ttttttttat    4200
attttgtttt gtgttatttt tttctttaac atccctaaaa ttttccttac atgttttact    4260
agccagattt ttcctcctct cctgactact cccagtcata gctgtccctc ttctcttatg    4320
gagatcgaag caattcgttg atctgaattt cgaccaccca taatagatct cccattaccc    4380
tggtagataa gtagcatggc gggttaatca ttaactacaa ggaaccccta gtgatggagt    4440
tggccactcc ctctctgcgc gctcgctcgc tcactgaggc cgggcgacca aaggtcgccc    4500
gacgcccggg ctttgcccgg gcggcctcag tgagcgagcg agcgcgcag              4549

<210> SEQ ID NO 11
<211> LENGTH: 130
<212> TYPE: DNA
<213> ORGANISM: Unknown
<220> FEATURE:
<223> OTHER INFORMATION: inverted terminal repeat (ITR) sequence

<400> SEQUENCE: 11
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct                                                          130

<210> SEQ ID NO 12
<211> LENGTH: 130
<212> TYPE: DNA
<213> ORGANISM: Unknown
<220> FEATURE:
<223> OTHER INFORMATION: inverted terminal repeat (ITR) sequence

<400> SEQUENCE: 12
aggaacccct agtgatggag ttggccactc cctctctgcg cgctcgctcg ctcactgagg     60
ccgggcgacc aaaggtcgcc cgacgcccgg gctttgcccg gcggcctca gtgagcgagc     120 gagcgcgcag                                                          130

<210> SEQ ID NO 13

<400> SEQUENCE: 13

000

<210> SEQ ID NO 14
<211> LENGTH: 13
<212> TYPE: RNA
<213> ORGANISM: Unknown
<220> FEATURE:
<223> OTHER INFORMATION: alternative Kozak sequence
<220> FEATURE:
<221> NAME/KEY: misc_feature
<222> LOCATION: (1)..(3)
<223> OTHER INFORMATION: May be absent
<220> FEATURE:
<221> NAME/KEY: misc_feature
<222> LOCATION: (1)..(1)
```

```
<223> OTHER INFORMATION: g is the most common base, but may vary
<220> FEATURE:
<221> NAME/KEY: misc_feature
<222> LOCATION: (2)..(3)
<223> OTHER INFORMATION: c is the most common base, but may vary
<220> FEATURE:
<221> NAME/KEY: misc_feature
<222> LOCATION: (4)..(4)
<223> OTHER INFORMATION: g is the most common base, but may vary
<220> FEATURE:
<221> NAME/KEY: misc_feature
<222> LOCATION: (5)..(6)
<223> OTHER INFORMATION: c is the most common base, but may vary
<220> FEATURE:
<221> NAME/KEY: misc_feature
<222> LOCATION: (8)..(9)
<223> OTHER INFORMATION: c is the most common base, but may vary

<400> SEQUENCE: 14
nnnnnnrnna ugg                                                            13

<210> SEQ ID NO 15
<211> LENGTH: 8
<212> TYPE: RNA
<213> ORGANISM: Unknown
<220> FEATURE:
<223> OTHER INFORMATION: alternative Kozak sequence
<220> FEATURE:
<221> NAME/KEY: misc_feature
<222> LOCATION: (3)..(4)
<223> OTHER INFORMATION: n is a, c, g, or u
<220> FEATURE:
<221> NAME/KEY: misc_feature
<222> LOCATION: (8)..(8)
<223> OTHER INFORMATION: n is a, c, g, or u

<400> SEQUENCE: 15 agnnaugn                                                                   8

<210> SEQ ID NO 16
<211> LENGTH: 7
<212> TYPE: RNA
<213> ORGANISM: Unknown
<220> FEATURE:
<223> OTHER INFORMATION: alternative Kozak sequence
<220> FEATURE:
<221> NAME/KEY: misc_feature
<222> LOCATION: (2)..(3)
<223> OTHER INFORMATION: n is a, c, g, or u

<400> SEQUENCE: 16 annaugg                                                                    7

<210> SEQ ID NO 17
<211> LENGTH: 7
<212> TYPE: RNA
<213> ORGANISM: Unknown
<220> FEATURE:
<223> OTHER INFORMATION: alternative Kozak sequence

<400> SEQUENCE: 17 accaugg                                                                    7

<210> SEQ ID NO 18
<211> LENGTH: 10
<212> TYPE: RNA
<213> ORGANISM: Unknown
<220> FEATURE:
<223> OTHER INFORMATION: alternative Kozak sequence

<400> SEQUENCE: 18
```

```
gacaccaugg                                                              10

<210> SEQ ID NO 19
<211> LENGTH: 235
<212> TYPE: DNA
<213> ORGANISM: Bos taurus

<400> SEQUENCE: 19
tcgactgtgc cttctagttg ccagccatct gttgtttgcc cctcccccgt gccttccttg       60
accctggaag gtgccactcc cactgtcctt tcctaataaa atgaggaaat tgcatcgcat      120
tgtctgagta ggtgtcattc tattctgggg ggtggggtgg ggcaggacag caaggggagg     180
gattgggagg acaatagcag gcatgctggg gatgcggtgg gctctatggc ttctg           235

<210> SEQ ID NO 20
<211> LENGTH: 222
<212> TYPE: DNA
<213> ORGANISM: Simian virus 40

<400> SEQUENCE: 20
cagacatgat aagatacatt gatgagtttg gacaaaccac aactagaatg cagtgaaaaa       60
aatgctttat ttgtgaaatt tgtgatgcta ttgctttatt tgtaaccatt ataagctgca      120
ataaacaagt taacaacaac aattgcattc attttatgtt tcaggttcag ggggagatgt      180
gggaggtttt ttaaagcaag taaaacctct acaaatgtgg ta                          222

<210> SEQ ID NO 21
<211> LENGTH: 202
<212> TYPE: DNA
<213> ORGANISM: Homo sapiens

<400> SEQUENCE: 21
ctgcccgggt ggcatccctg tgaccccctcc ccagtgcctc tcctggcccct ggaagttgcc     60 actccagtgc ccaccagcct tgtcctaata aaattaagtt gcatcatttt gtctgactag      120
gtgtccttct ataatattat ggggtggagg ggggtggtat ggagcaaggg gcccaagttg      180 ggaagaaaacc tgtagggcct gc                                               202

<210> SEQ ID NO 22
<211> LENGTH: 1730
<212> TYPE: DNA
<213> ORGANISM: Unknown
<220> FEATURE:
<223> OTHER INFORMATION: CAG promoter

<400> SEQUENCE: 22
ctagtcgaca ttgattattg actagttatt aatagtaatc aattacgggg tcattagttc       60
atagcccata tatggagttc cgcgttacat aacttacggt aaatggcccg cctggctgac      120
cgcccaacga cccccgccca ttgacgtcaa taatgacgta tgttcccata gtaacgccaa      180
tagggacttt ccattgacgt caatgggtgg agtatttacg gtaaactgcc cacttggcag      240
tacatcaagt gtatcatatg ccaagtacgc cccctattga cgtcaatgac ggtaaatggc      300
ccgcctggca ttatgcccag tacatgacct tatgggactt tcctacttgg cagtacatct      360
acgtattagt catcgctatt accatggtcg aggtgagccc cacgttctgc ttcactctcc      420
ccatctcccc cccctcccca ccccaatttt gtatttattt attttttaa ttattttgtg       480 cagcgatggg ggcggggggg gggggggggc gcgcgccagg cggggcgggg cggggcgagg      540
```

```
ggcggggcgg ggcgaggcgg agaggtgcgg cggcagccaa tcagagcggc gcgctccgaa      600
agtttccttt tatggcgagg cggcggcggc ggcggcccta taaaaagcga agcgcgcggc      660
gggcgggagt cgctgcgcgc tgccttcgcc ccgtgccccg ctccgccgcc gcctcgcgcc      720
gcccgccccg gctctgactg accgcgttac tcccacaggt gagcgggcgg gacggccctt      780
ctcctccggg ctgtaattag cgcttggttt aatgacggct tgtttctttt ctgtggctgc      840
gtgaaagcct tgagggggctc cgggagggcc ctttgtgcgg ggggagcggc tcgggggggtg    900 cgtgcgtgtg tgtgtgcgtg gggagcgccg cgtgcggctc cgcgctgccc ggcggctgtg      960
agcgctgcgg gcgcggcgcg gggctttgtg cgctccgcag tgtgcgcgag gggagcgcgg     1020 ccggggggcgg tgccccgcgg tgcgggggggg gctgcgaggg gaacaaaggc tgcgtgcggg   1080
gtgtgtgcgt gggggggtga gcaggggggtg tgggcgcgtc ggtcgggctg caaccccccc   1140
tgcacccccc tccccgagtt gctgagcacg gcccggcttc gggtgcgggg ctccgtacgg    1200
ggcgtggcgc ggggctcgcc gtgccggggcg ggggtggcg gcaggtgggg gtgccgggcg    1260
gggcggggcc gcctcgggcc ggggagggct cggggggaggg gcgcggcggc ccccggagcg   1320
ccggcggctg tcgaggcgcg gcgagccgca gccattgcct tttatggtaa tcgtgcgaga    1380
gggcgcaggg acttcctttg tcccaaatct gtgcggagcc gaaatctggg aggcgccgcc    1440
gcaccccctc tagcgggcgc ggggcgaagc ggtgcggcgc cggcaggaag gaaatgggcg    1500
gggagggcct tcgtgcgtcg ccgcgccgcc gtccccttct ccctctccag cctcgggct     1560 gtccgcgggg ggacggctgc cttcgggggg gacggggcag ggcggggttc ggcttctggc    1620
gtgtgaccgg cggctctaga gcctctgcta accatgttca tgccttcttc tttttcctac    1680
agctcctggg caacgtgctg gttattgtgc tgtctcatca ttttggcaaa                1730

<210> SEQ ID NO 23
<211> LENGTH: 204
<212> TYPE: DNA
<213> ORGANISM: Human cytomegalovirus

<400> SEQUENCE: 23
gtgatgcggt tttggcagta catcaatggg cgtggatagc ggtttgactc acggggattt       60
ccaagtctcc accccattga cgtcaatggg agtttgtttt ggcaccaaaa tcaacgggac      120
tttccaaaat gtcgtaacaa ctccgcccca ttgacgcaaa tgggcggtag cgtgtacgg      180 tgggaggtct atataagcag agct                                             204

<210> SEQ ID NO 24
<211> LENGTH: 317
<212> TYPE: DNA
<213> ORGANISM: Simian virus 40

<400> SEQUENCE: 24
ggtgtggaaa gtccccaggc tccccagcag gcagaagtat gcaaagcatg catctcaatt       60
agtcagcaac caggtgtgga aagtccccag gctccccagc aggcagaagt atgcaaagca      120
tgcatctcaa ttagtcagca accatagtcc cgcccctaac tccgcccatc cgcccctaa      180 ctccgcccag ttccgcccat tctccgcccc atggctgact aatttttttt atttatgcag     240
aggccgaggc cgcctcggcc tctgagctat tccagaagta gtgaggaggc ttttttggag     300
gcctaggctt ttgcaaa                                                      317

<210> SEQ ID NO 25
<211> LENGTH: 500
```

<212> TYPE: DNA
<213> ORGANISM: Unknown
<220> FEATURE:
<223> OTHER INFORMATION: PGK promoter

<400> SEQUENCE: 25

| | | | | | | |
|---|---|---|---|---|---|---|
| gggtagggga | ggcgcttttc | ccaaggcagt | ctggagcatg | cgctttagca | gccccgctgg | 60 |
| gcacttggcg | ctacacaagt | ggcctctggc | ctcgcacaca | ttccacatcc | accggtaggc | 120 |
| gccaaccggc | tccgttcttt | ggtggcccct | tcgcgccacc | ttctactcct | ccctagtca | 180 |
| ggaagttccc | ccccgccccg | cagctcgcgt | cgtgcaggac | gtgacaaatg | gaagtagcac | 240 |
| gtctcactag | tctcgtgcag | atggacagca | ccgctgagca | atggaagcgg | gtaggccttt | 300 |
| ggggcagcgg | ccaatagcag | ctttgctcct | tcgctttctg | ggctcagagg | ctgggaaggg | 360 |
| gtgggtccgg | gggcgggctc | aggggcgggc | tcaggggcgg | ggcgggcgcc | cgaaggtcct | 420 |
| ccggaggccc | ggcattctgc | acgcttcaaa | agcgcacgtc | tgccgcgctg | ttctcctctt | 480 |
| cctcatctcc | gggcctttcg | | | | | 500 |

<210> SEQ ID NO 26
<211> LENGTH: 2403
<212> TYPE: DNA
<213> ORGANISM: Homo sapiens

<400> SEQUENCE: 26

| | | | | | | |
|---|---|---|---|---|---|---|
| cctgcagggc | ccactagttc | catgtcctta | tatggactca | tctttgccta | ttgcgacaca | 60 |
| cactcaatga | acacctacta | cgcgctgcaa | agagccccgc | aggcctgagg | tgccccacc | 120 |
| tcaccactct | tcctatttt | gtgtaaaaat | ccagcttctt | gtcaccacct | ccaaggaggg | 180 |
| ggaggaggag | gaaggcaggt | tcctctaggc | tgagccgaat | gccctctgt | ggtcccacgc | 240 |
| cactgatcgc | tgcatgccca | ccacctgggt | acacacagtc | tgtgattccc | ggagcagaac | 300 |
| ggaccctgcc | cacccggtct | tgtgtgctac | tcagtggaca | gacccaaggc | aagaaagggt | 360 |
| gacaaggaca | gggtcttccc | aggctggctt | tgagttccta | gcaccgcccc | gccccaatc | 420 |
| ctctgtggca | catggagtct | tggtccccag | agtcccccag | cggcctccag | atggtctggg | 480 |
| agggcagttc | agctgtggct | gcgcatagca | gacatacaac | ggacggtggg | cccagaccca | 540 |
| ggctgtgtag | acccagcccc | cccgccccgc | agtgcctagg | tcacccacta | acgcccagg | 600 |
| cctggtcttg | gctgggcgtg | actgttaccc | tcaaaagcag | gcagctccag | ggtaaaaggt | 660 |
| gccctgccct | gtagagccca | ccttccttcc | cagggctgcg | gctgggtagg | tttgtagcct | 720 |
| tcatcacggg | ccacctccag | ccactggacc | gctggcccct | gccctgtcct | ggggagtgtg | 780 |
| gtcctgcgac | ttctaagtgg | ccgcaagcca | cctgactccc | caacaccac | actctacctc | 840 |
| tcaagcccag | gtctctccct | agtgaccac | ccagcacatt | tagctagctg | agccccacag | 900 |
| ccagaggtcc | tcaggccctg | ctttcagggc | agttgctctg | aagtcggcaa | ggggagtga | 960 |
| ctgcctggac | actccatgcc | ctccaagagc | tccttctgca | ggagcgtaca | gaacccaggg | 1020 |
| ccctggcacc | cgtgcagacc | ctggcccacc | ccacctgggc | gctcagtgcc | caagagatgt | 1080 |
| ccacacctag | gatgtcccgc | ggtgggtggg | gggcccgaga | gacgggcagg | ccgggggcag | 1140 |
| gcctggccat | gcggggccga | accgggcact | gcccagcgtg | gggcgcgggg | gccacggcgc | 1200 |
| gcgcccccag | cccccgggcc | cagcacccca | aggcggccaa | cgccaaaact | ctccctcctc | 1260 |
| ctcttcctca | atctcgctct | cgctctttt | tttttcgca | aaaggagggg | agaggggta | 1320 |
| aaaaaatgct | gcactgtgcg | gcgaagccgg | tgagtgagcg | gcgcggggcc | aatcagcgtg | 1380 |

```
cgccgttccg aaagttgcct tttatggctc gagcggccgc ggcggcgccc tataaaaccc    1440
agcggcgcga cgcgccacca ccgccgagac cgcgtccgcc ccgcgagcac agagcctcgc    1500
ctttgccgat ccgccgcccg tccacacccg ccgccaggta agcccggcca gccgaccggg    1560
gcaggcggct cacggcccgg ccgcaggcgg ccgcggcccc ttcgcccgtg cagagccgcc    1620
gtctgggccg cagcggggg cgcatggggg gggaaccgga ccgccgtggg gggcgcggga    1680
gaagcccctg ggcctccgga gatgggggac accccacgcc agttcggagg cgcgaggccg    1740
cgctcgggag gcgcgctccg ggggtgccgc tctcggggcg ggggcaaccg gcggggtctt    1800
tgtctgagcc gggctcttgc caatgggggat cgcagggtgg gcgcggcgga gccccgcca    1860 ggcccggtgg gggctgggc gccattgcgc gtgcgcgctg gtcctttggg cgctaactgc    1920
gtgcgcgctg ggaattggcg ctaattgcgc gtgcgcgctg ggactcaagg cgctaactgc    1980
gcgtgcgttc tggggcccgg ggtgccgcgg cctgggctgg ggcgaaggcg ggctcggccg    2040 gaagggggtgg ggtcgccgcg gctcccgggc gcttgcgcgc acttcctgcc cgagccgctg    2100
gccgcccgag ggtgtggccg ctgcgtgcgc gcgcgccgac ccggcgctgt ttgaaccggg    2160
cggaggcggg gctggcgccc ggttgggagg gggttggggc ctggcttcct gccgcgcgcc    2220
gcggggacgc ctccgaccag tgtttgcctt ttatggtaat aacgcggccg gcccggcttc    2280
ctttgtcccc aatctgggcg cgcgccggcg cccctggcg gcctaaggac tcggcgcgcc    2340
ggaagtggcc agggcggggg cgacctcggc tcacagcgcg cccggctatt ctcgcagctc    2400
acc                                                                2403

<210> SEQ ID NO 27
<211> LENGTH: 596
<212> TYPE: DNA
<213> ORGANISM: Woodchuck hepatitis virus

<400> SEQUENCE: 27
attcgagcat cttaccgcca tttattccca tatttgttct gttttttcttg atttgggtat      60 acatttaaat gttaataaaa caaaatggtg gggcaatcat ttacattttt agggatatgt     120
aattactagt tcaggtgtat tgccacaaga caaacatgtt aagaaacttt cccgttattt     180
acgctctgtt cctgttaatc aacctctgga ttacaaaatt tgtgaaagat tgactgatat     240
tcttaactat gttgctcctt ttacgctgtg tggatatgct gctttaatgc ctctgtatca     300
tgctattgct tcccgtacgg ctttcgtttt ctcctccttg tataaatcct ggttgctgtc     360
tctttatgag gagttgtggc ccgttgtccg tcaacgtggc gtggtgtgct ctgtgtttgc     420
tgacgcaacc cccactggct ggggcattgc caccacctgt caactccttt ctgggacttt     480
cgctttcccc ctcccgatcg ccacggcaga actcatcgcc gcctgccttg cccgctgctg     540 gacagggggct aggttgctgg gcactgataa ttccgtggtg ttgtcgggga agggcc         596

<210> SEQ ID NO 28
<211> LENGTH: 736
<212> TYPE: PRT
<213> ORGANISM: adeno-associated virus 9

<400> SEQUENCE: 28

Met Ala Ala Asp Gly Tyr Leu Pro Asp Trp Leu Glu Asp Asn Leu Ser
1               5                  10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
```

```
            35                  40                  45
Gly Tyr Lys Tyr Leu Gly Pro Gly Asn Gly Leu Asp Lys Gly Glu Pro
 50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
        130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
450                 455                 460
```

| | | | | | | | | | | | | |
|---|---|---|---|---|---|---|---|---|---|---|---|---|
| Val | Ala | Gly | Pro | Ser | Asn | Met | Ala | Val | Gln | Gly | Arg | Asn | Tyr | Ile | Pro |
| 465 | | | | 470 | | | | 475 | | | | 480 |

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
        500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735

<210> SEQ ID NO 29
<211> LENGTH: 1233
<212> TYPE: DNA
<213> ORGANISM: Homo sapiens

<400> SEQUENCE: 29
atggtgtgct tccgcctctt cccggttccg ggctcagggc tcgttctggt ctgcctagtc      60
ctgggagctg tgcggtctta tgcattggaa cttaatttga cagattcaga aaatgccact     120
tgcctttatg caaatggca gatgaatttc acagtacgct atgaaactac aaataaaact     180
tataaaactg taaccatttc agaccatggc actgtgacat ataatggaag catttgtggg     240
gatgatcaga atggtcccaa aatagcagtg cagttcggac ctggcttttc ctggattgcg     300
aattttacca aggcagcatc tactattca attgacagcg tctcattttc ctacaacact     360
ggtgataaca acacatttcc tgatgctgaa gataaggaa ttcttactgt tgatgaactt     420
ttggccatca gaattccatt gaatgacctt tttagatgca atagtttatc aactttggaa     480
aagaatgatg ttgtccaaca ctactgggat gttcttgtac aagcttttgt ccaaatggc     540 acagtgagca caaatgagtt cctgtgtgat aaagacaaaa cttcaacagt ggcacccacc     600

```
atacacacca ctgtgccatc tcctactaca acacctactc caaaggaaaa accagaagct    660
ggaacctatt cagttaataa tggcaatgat acttgtctgc tggctaccat ggggctgcag    720
ctgaacatca ctcaggataa ggttgcttca gttattaaca tcaaccccaa tacaactcac    780
tccacaggca gctgccgttc tcacactgct ctacttagac tcaatagcag caccattaag    840
tatctagact ttgtctttgc tgtgaaaaat gaaaaccgat tttatctgaa ggaagtgaac    900
atcagcatgt atttggttaa tggctccgtt ttcagcattg caaataacaa tctcagctac    960
tgggatgccc ccctgggaag ttcttatatg tgcaacaaag agcagactgt ttcagtgtct   1020
ggagcatttc agataaatac ctttgatcta agggttcagc ctttcaatgt gacacaagga   1080
aagtattcta cagctcaaga ctgcagtgca gatgacgaca acttccttgt gcccatagcg   1140
gtgggagctg ccttggcagg agtacttatt ctagtgttgc tggcttattt tattggtctc   1200
aagcaccatc atgctggata tgagcaattt tag                                1233

<210> SEQ ID NO 30
<211> LENGTH: 1236
<212> TYPE: DNA
<213> ORGANISM: Homo sapiens

<400> SEQUENCE: 30
atggtgtgct tccgcctctt cccggttccg ggctcagggc tcgttctggt ctgcctagtc     60
ctgggagctg tgcggtctta tgcattggaa cttaatttga cagattcaga aaatgccact    120
tgcctttatg caaaatggca gatgaatttc acagtacgct atgaaactac aaataaaact    180
tataaaactg taaccatttc agaccatggc actgtgacat ataatggaag catttgtggg    240
gatgatcaga atggtcccaa aatagcagtg cagttcggac ctggcttttc ctggattgcg    300
aattttacca aggcagcatc tacttattca attgacagcg tctcatttt c ctacaacact    360 ggtgataaca caacatttcc tgatgctgaa gataaaggaa ttcttactgt tgatgaactt    420
ttggccatca gaattccatt gaatgacctt tttagatgca atagtttat c aactttggaa    480 aagaatgatg ttgtccaaca ctactgggat gttcttgtac aagcttttgt ccaaaatggc    540
acagtgagca caaatgagtt cctgtgtgat aaagacaaaa cttcaacagt ggcacccacc    600
atacacacca ctgtgccatc tcctactaca acacctactc caaaggaaaa accagaagct    660
ggaacctatt cagttaataa tggcaatgat acttgtctgc tggctaccat ggggctgcag    720
ctgaacatca ctcaggataa ggttgcttca gttattaaca tcaaccccaa tacaactcac    780
tccacaggca gctgccgttc tcacactgct ctacttagac tcaatagcag caccattaag    840
tatctagact ttgtctttgc tgtgaaaaat gaaaaccgat tttatctgaa ggaagtgaac    900
atcagcatgt atttggttaa tggctccgtt ttcagcattg caaataacaa tctcagctac    960
tgggatgccc ccctgggaag ttcttatatg tgcaacaaag agcagactgt ttcagtgtct   1020
ggagcatttc agataaatac ctttgatcta agggttcagc ctttcaatgt gacacaagga   1080
aagtattcta cagctgaaga atgttctgct gactctgacc tcaactttct tattcctgtt   1140
gcagtgggtg tggccttggg cttccttata attgttgtct ttatctctta tatgattgga   1200
agaaggaaaa gtcgtactgg ttatcagtct gtgtaa                             1236

<210> SEQ ID NO 31
<211> LENGTH: 1000
<212> TYPE: DNA
<213> ORGANISM: Artificial Sequence
<220> FEATURE:
```

<223> OTHER INFORMATION: variant of LAMP-2

<400> SEQUENCE: 31

| | | | | | |
|---|---|---|---|---|---|
| atggtctgct | tcagactgtt | ccctgtccct | ggatctggtc | tggtgcttgt | gtgcttggtg | 60 |
| ctgggtgctg | tgagatccta | tgcccttgag | ctgaacctga | ctgactcaga | aaatgccact | 120 |
| tgcctgtatg | ccaagtggca | gatgaacttc | actgtgagat | atgagactac | caacaagacc | 180 |
| tacaagactg | tgaccatctc | agaccatggc | actgtcacct | acaatggatc | aatctgtggt | 240 |
| gatgatcaga | atggcccaaa | gatagcagtg | cagtttgggc | ccggtttttc | ctggattgct | 300 |
| aacttcacca | aggcagcctc | cacctacagc | attgactcag | tcagcttcag | ctacaacact | 360 |
| ggggataaca | ccaccttccc | tgacgcagag | gacaagggaa | tccttactgt | ggacgaactc | 420 |
| ctggcaatca | gaatcccct | taacgacctg | ttcagatgca | actccctttc | aacccttgaa | 480 |
| aagaatgatg | tggtgcaaca | ctattgggac | gtcctggtgc | aagcctttgt | gcagaatggg | 540 |
| acagtgagta | ccaacgagtt | cctctgtgac | aaggacaaga | ccagcactgt | ggcccccact | 600 |
| atccacacca | ctgtgcccag | ccctaccact | accccaccc | ctaaagagaa | gccagaagct | 660 |
| ggaacctact | cagtcaacaa | tggaaatgac | acatgcctcc | ttgccaccat | gggactgcag | 720 |
| ctgaacatca | ctcaggacaa | ggtggcctca | gtgattaaca | tcaaccctaa | caccactcat | 780 |
| agcactggga | gctgcagatc | acatacagct | ctgctgaggc | tcaactcctc | caccatcaag | 840 |
| tacctggact | ttgtgtttgc | tgtgaagaat | gagaacaggt | tctacctcaa | ggaagtgaac | 900 |
| atttccatgt | acctggtcaa | tggttcagtg | ttctctattg | ccaacaacaa | tctgagctac | 960 |
| tgggatgcac | ccctgggatc | ctcctacatg | tgcaacaagg | | | 1000 |

<210> SEQ ID NO 32
<211> LENGTH: 1000
<212> TYPE: DNA
<213> ORGANISM: Artificial Sequence
<220> FEATURE:
<223> OTHER INFORMATION: variant of LAMP-2

<400> SEQUENCE: 32

| | | | | | |
|---|---|---|---|---|---|
| atggtgtgct | ttagactgtt | tcctgtgcct | ggttcagggc | tggtcctggt | ctgtctggtg | 60 |
| ctgggggctg | tcagaagcta | tgccttggag | ctgaacctca | ctgatagtga | aaatgccact | 120 |
| tgtctgtatg | ctaagtggca | gatgaacttc | actgtgagat | atgaaaccac | caacaagact | 180 |
| tacaaaacag | tgaccatctc | agatcatgga | actgtgacct | acaacggcag | catttgtgga | 240 |
| gacgaccaga | acggaccaaa | aatcgctgtc | caatttgggc | ctggattctc | ctggattgcc | 300 |
| aatttcacta | agctgcctc | cacatattca | attgactcag | tgtccttctc | ctacaacact | 360 |
| ggggacaaca | ctactttccc | tgatgctgaa | gataagggaa | tcttgacagt | ggatgagctg | 420 |
| ctggctatca | ggatcccttt | gaatgacctg | tttaggtgta | attcactgag | cactctggag | 480 |
| aagaacgacg | tggtgcagca | ctactgggac | gtgctggtgc | aggcctttgt | gcagaacggc | 540 |
| actgtgtcca | ccaacgaatt | cctgtgtgat | aaggacaaaa | cttccactgt | ggcacctaca | 600 |
| attcacacta | ctgtgccttc | acctaccacc | actccaactc | caaaggaaaa | gcctgaagca | 660 |
| ggaacctact | ctgtgaacaa | tggcaatgat | acctgtctgt | tggccaccat | gggcctccaa | 720 |
| ctgaacatta | ctcaggacaa | ggtggcctca | gtgattaaca | ttaaccccaa | cactacccac | 780 |
| tccactggca | gctgtagatc | acacacagcc | ttgctcagac | tgaatagcag | caccatcaag | 840 |
| tatttggatt | ttgtgtttgc | agtgaagaat | gaaaacaggt | tctacctgaa | ggaagtcaac | 900 |
| atctcaatgt | acctggtgaa | cggctcagtg | ttcagcattg | ccaacaacaa | cctctcctat | 960 | tgggacgctc cactggggag cagctacatg tgtaacaagg    1000

<210> SEQ ID NO 33
<211> LENGTH: 1000
<212> TYPE: DNA
<213> ORGANISM: Artificial Sequence
<220> FEATURE:
<223> OTHER INFORMATION: variant of LAMP-2

<400> SEQUENCE: 33
atggtctgtt ttaggctgtt ccctgtccct ggttcaggac tggtcttagt gtgtctggtg    60
cttggagctg tcagaagcta tgccctggag ctgaacctga ctgactcaga aaatgccact    120
tgcctgtatg ccaagtggca gatgaacttc actgtcagat atgaaaccac caacaagacc    180
tataagactg tgaccatctc agaccatggc actgtgactt acaatgggtc aatttgtgga    240
gatgaccaga atggccctaa gatagctgtc cagtttggtc caggattcag ctggattgcc    300
aacttcacca aggcagccag cacctacagc attgactctg tgtccttctc ctacaacaca    360
ggagacaaca ccactttccc tgatgcagag acaaaggta tcctgactgt ggatgagttg    420
ctggcaatca ggatcccact gaacgatctg ttcaggtgca actcactgtc cactctggaa    480
aagaatgatg tggtgcagca ctattgggat gtgctagtcc aggcctttgt ccagaatggg    540
actgtgtcaa ctaatgagtt cctgtgtgac aaggacaaga caagcactgt agccccccact    600
atccatacca cagtacctag cccaccact actccaaccc caaggagaa gcctgaggct    660
ggcacctact cagtgaacaa tgggaatgac acctgtttgc tggccactat gggactccaa    720
ctgaacatca cccaggacaa agtggcctct gtgatcaata tcaatcccaa caccacccac    780
agcactgggt cctgcagaag ccacactgcc ctcctgaggc tcaactcatc aactatcaag    840
tacttggatt ttgtgtttgc agtgaagaat gagaacagat tctacctcaa agaggtcaac    900
atttcaatgt acctggtgaa tgggagtgtg ttctccattg ctaacaacaa cctgagctac    960
tgggatgccc tctgggctc ctcatacatg tgcaacaagg    1000

<210> SEQ ID NO 34
<211> LENGTH: 410
<212> TYPE: PRT
<213> ORGANISM: Homo sapiens

<400> SEQUENCE: 34

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu Glu Leu Asn
            20                  25                  30

Leu Thr Asp Ser Glu Asn Ala Thr Cys Leu Tyr Ala Lys Trp Gln Met
        35                  40                  45

Asn Phe Thr Val Arg Tyr Glu Thr Thr Asn Lys Thr Tyr Lys Thr Val
    50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95

Ser Trp Ile Ala Asn Phe Thr Lys Ala Ala Ser Thr Tyr Ser Ile Asp
            100                 105                 110

Ser Val Ser Phe Ser Tyr Asn Thr Gly Asp Asn Thr Thr Phe Pro Asp
        115                 120                 125

```
Ala Glu Asp Lys Gly Ile Leu Thr Val Asp Glu Leu Leu Ala Ile Arg
    130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
            180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Ile Ser Met Tyr
    290                 295                 300

Leu Val Asn Gly Ser Val Phe Ser Ile Ala Asn Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Gln Asp Cys
        355                 360                 365

Ser Ala Asp Asp Asp Asn Phe Leu Val Pro Ile Ala Val Gly Ala Ala
    370                 375                 380

Leu Ala Gly Val Leu Ile Leu Val Leu Leu Ala Tyr Phe Ile Gly Leu
385                 390                 395                 400

Lys His His His Ala Gly Tyr Glu Gln Phe
                405                 410

<210> SEQ ID NO 35
<211> LENGTH: 411
<212> TYPE: PRT
<213> ORGANISM: Homo sapiens

<400> SEQUENCE: 35

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu Glu Leu Asn
            20                  25                  30

Leu Thr Asp Ser Glu Asn Ala Thr Cys Leu Tyr Ala Lys Trp Gln Met
        35                  40                  45

Asn Phe Thr Val Arg Tyr Glu Thr Thr Asn Lys Thr Tyr Lys Thr Val
    50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95
```

```
Ser Trp Ile Ala Asn Phe Thr Lys Ala Ser Thr Tyr Ser Ile Asp
            100                 105                 110

Ser Val Ser Phe Ser Tyr Asn Thr Gly Asp Asn Thr Thr Phe Pro Asp
            115                 120                 125

Ala Glu Asp Lys Gly Ile Leu Thr Val Asp Glu Leu Leu Ala Ile Arg
130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
            180                 185                 190

Lys Thr Ser Thr Val Ala Pro Thr Ile His Thr Thr Val Pro Ser Pro
                195                 200                 205

Thr Thr Thr Pro Thr Pro Lys Glu Lys Pro Glu Ala Gly Thr Tyr Ser
            210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
            275                 280                 285

Lys Asn Glu Asn Arg Phe Tyr Leu Lys Glu Val Asn Ile Ser Met Tyr
            290                 295                 300

Leu Val Asn Gly Ser Val Phe Ser Ile Ala Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Glu Glu Cys
            355                 360                 365

Ser Ala Asp Ser Asp Leu Asn Phe Leu Ile Pro Val Ala Val Gly Val
370                 375                 380

Ala Leu Gly Phe Leu Ile Ile Val Phe Ile Ser Tyr Met Ile Gly
385                 390                 395                 400

Arg Arg Lys Ser Arg Thr Gly Tyr Gln Ser Val
                405                 410

<210> SEQ ID NO 36
<211> LENGTH: 21
<212> TYPE: DNA
<213> ORGANISM: Woodchuck hepatitis virus

<400> SEQUENCE: 36
atcatgctat tgcttcccgt a                                         21

<210> SEQ ID NO 37
<211> LENGTH: 20
<212> TYPE: DNA
<213> ORGANISM: Woodchuck hepatitis virus

<400> SEQUENCE: 37
```

```
gggccacaac tcctcataaa                                             20

<210> SEQ ID NO 38
<211> LENGTH: 29
<212> TYPE: DNA
<213> ORGANISM: Woodchuck hepatitis virus

<400> SEQUENCE: 38
cctccttgta taaatcctgg ttgctgtct                                   29
```

GENE THERAPY VECTORS FOR TREATMENT OF DANON DISEASE

RELATED APPLICATIONS

This application is a continuation of International Patent Application No. PCT/US2019/041465, filed Jul. 11, 2019, which claims priority to U.S. Provisional Patent Application No. 62/697,302, filed Jul. 12, 2018, each of which is incorporated herein by reference in its entirety.

SEQUENCE LISTING

This application is being filed electronically via EFS-Web and includes an electronically submitted sequence listing in .txt format. The .txt file contains a sequence listing entitled "ROPA_011_01US_ST25.txt" created on Dec. 11, 2019 and having a size of 62 kilobytes. The sequence listing contained in this .txt file is part of the specification and is incorporated herein by reference in its entirety.

FIELD OF INVENTION

The invention relates generally to gene therapy for diseases associated with mutations in lysosome-associated membrane protein 2 (LAMP-2, also known as CD107b).

BACKGROUND

Lysosome-associated membrane protein 2 (LAMP-2, also known as CD107b) is a gene that encodes a lysosome-associated membrane glycoprotein. Alternative splicing of the gene produces three isoforms: LAMP-2A, LAMP-2B, and LAMP-2C. Loss-of-function mutations in LAMP-2 are associated with human diseases, including Danon disease, a familial cardiomyopathy associated with impaired autophagy.

International Patent Application Publication No. WO2017127565A1 discloses that overexpression of LAMP-2 in human induced pluripotent stem cells (hiPSCs) derived from patients with LAMP-2 mutations, as described in Hashem, et al., Stem Cells. 2015 July; 33(7):2343-50, results in reduced oxidative stress levels and apoptotic cell death, confirming the importance of LAMP-2B in disease pathophysiology.

There remains a need in the art for gene therapy vectors for LAMP-2. The present disclosure provides such gene therapy vectors, methods of use thereof, pharmaceutical compositions, and more.

SUMMARY OF THE INVENTION

The present disclosure provides improved gene therapy vectors comprising a polynucleotide sequence encoding a LAMP-2 polypeptide, methods of use thereof, pharmaceutical compositions, and more.

In one aspect, the disclosure provides a gene therapy vector comprising an expression cassette comprising a transgene encoding an isoform of lysosome-associated membrane protein 2 (LAMP-2) or a functional variant thereof, wherein the transgene is codon-optimized for expression in a human host cell.

In an embodiment, the expression cassette contains fewer CpG sites than SEQ ID: 2.

In an embodiment, the expression cassette contains fewer cryptic splice sites than SEQ ID: 2.

In an embodiment, the expression cassette encodes fewer alternative open reading frames than SEQ ID: 2.

In an embodiment, the transgene shares at least 95% identity to a sequence selected from SEQ ID NOs: 3-5.

In an embodiment, the transgene shares at least 99% identity to a sequence selected from SEQ ID NOs: 3-5.

In an embodiment, the transgene comprises a sequence selected from SEQ ID NOs: 3-5.

In an embodiment, the transgene shares at least 95% identity to SEQ ID NO: 3.

In an embodiment, the transgene shares at least 99% identity to SEQ ID NO: 3.

In an embodiment, the transgene comprises a sequence identical to SEQ ID NO: 3.

In an embodiment, the expression cassette comprises a consensus optimal Kozak sequence operatively linked to the transgene, wherein optionally the consensus optimal Kozak sequence comprises SEQ ID NO: 6.

In an embodiment, the expression cassette comprises a full-length polyA sequence operatively linked to the transgene, wherein optionally the full-length polyA sequence comprises SEQ ID NO: 7.

In an embodiment, the expression cassette comprises no start site 5' to the transgene capable of generating alternative mRNAs.

In an embodiment, the expression cassette comprises operatively linked, in the 5' to 3' direction, a first inverse terminal repeat, an enhancer/promoter region, a consensus optimal Kozak sequence, the transgene, a 3' untranslated region including a full-length polyA sequence, and a second inverse terminal repeat.

In an embodiment, the enhancer/promoter region comprises in the 5' to 3' direction a CMV IE enhancer and a chicken beta-actin promoter.

In an embodiment, the expression cassette shares at least 95% identity to a sequence selected from SEQ ID NOs: 8-10.

In an embodiment, the expression cassette shares complete identity to a sequence selected from SEQ ID NOs: 8-10.

In a second aspect, the disclosure provides a method of preventing, mitigating, ameliorating, reducing, inhibiting, eliminating and/or reversing one or more symptoms of Danon disease or another autophagy disorder in a subject in need thereof, comprising administering to the subject any gene therapy vector of the disclosure.

In an embodiment, the vector is administered via a route selected from the group consisting of intravenous, intra-arterial, intracardiac, intracoronary, intramyocardial, intrarenal, intraurethral, epidural, and intramuscular.

In an embodiment, the autophagy disorder is selected from the group consisting of end-stage heart failure, myocardial infarction, drug toxicities, diabetes, end-stage renal failure, and aging.

In an embodiment, the subject is a human.

In an embodiment, the subject is exhibiting symptoms of Danon disease or another autophagy disorder.

In an embodiment, the subject has been identified as having reduced or non-detectable LAMP-2 expression.

In an embodiment, the subject has been identified as having a mutated LAMP-2 gene.

In a third aspect, the disclosure provides a pharmaceutical composition for use in preventing, mitigating, ameliorating, reducing, inhibiting, eliminating and/or reversing one or more symptoms of Danon disease or another autophagy disorder, comprising any gene therapy vector of the disclosure.

Other features and advantages of the invention will be apparent from and encompassed by the following detailed description and claims.

BRIEF DESCRIPTION OF THE DRAWINGS

FIG. 10E shows percentage of cells expressing transgene mRNA in situ in heart, muscle and liver tissue isolated from primates injected with AAV9-optimized human LAMP-2B vector (treated) or no vector vehicle control (untreated). Individuals are denoted as B059 (male, M), A991 (female, F), and A602 (male, M).

FIG. 10F shows transgene mRNA staining in situ in heart tissue isolated from primates injectioned with the AAV9-optimized human LAMP-2B vector or no vector vehicle control (untreated). Individuals are denoted as B059 (male, M), A991 (female, F), and A602 (male, M).

DETAILED DESCRIPTION OF THE INVENTION

Figure 1A:
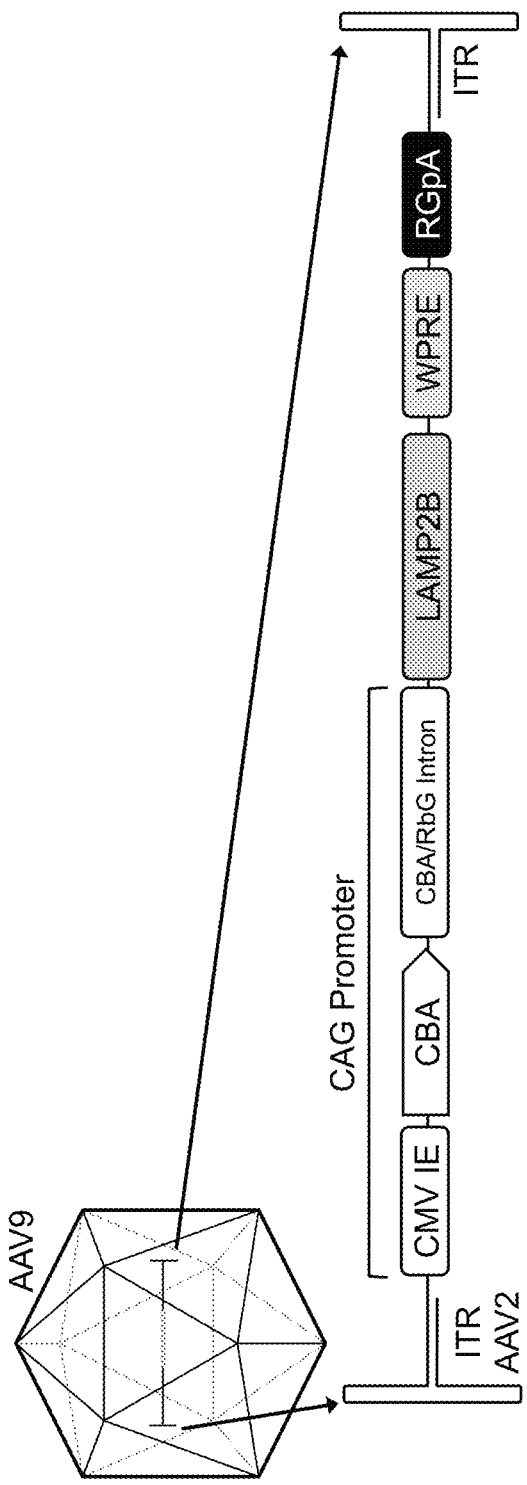
FIG. 1A provides a diagram of an illustrative embodiment of a viral vector of the disclosure.

The present disclosure provides improved polynucleotide sequences, expression cassettes, and vectors encoding an isoform of LAMP-2 (e.g., LAMP-2B), as well as related pharmaceutical compositions, and their use to treat diseases and disorders associated with LAMP-2 deficiency or mutation. The present inventors have discovered that modifications to the gene sequence of LAMP-2B result in increased transgene expression. In addition, the presence of specific sequence elements in the expression cassettes of gene therapy vectors encoding LAMP-2B result in an improvement in transgene expression. Accordingly, the LAMP-2 polynucleotide sequences, expression cassettes, and vectors disclosed herein offer advantages for gene therapy as compared to previous gene therapy vectors, including the ability to achieve higher levels of LAMP-2 expression in therapeutically relevant tissues.

The wild-type polypeptide sequence of human LAMP-2B (SEQ ID NO: 1) and the wild-type polynucleotide sequence encoding human LAMP-2B (SEQ ID NO: 2) are, respectively:

```
                                                                     (SEQ ID NO: 1)
    1    MVCFRLFPVP GSGLVLVCLV LGAVRSYALE LNLTDSENAT CLYAKWQMNF TVRYETTNKT

61    YKTVTISDHG TVTYNGSICG DDQNGPKIAV QFGPGFSWIA NFTKAASTYS IDSVSFSYNT

121    GDNTTFPDAE DKGILTVDEL LAIRIPLNDL FRCNSLSTLE KNDVVQHYWD VLVQAFVQNG

181    TVSTNEFLCD KDKTSTVAPT IHTTVPSPTT TPTPKEKPEA GTYSVNNGND TCLLATMGLQ

241    LNITQDKVAS VININPNTTH STGSCRSHTA LLRLNSSTIK YLDFVPAVKN ENRFYLKEVN

301    ISMYLVNGSV FSIANNNLSY WDAPLGSSYM CNKEQTVSVS GAFQINTFDL RVQPFNVTQG

361    KYSTAQECSL DDDTILIPII VGAGLSGLII VIVIAYVIGR RKSYAGYQT;
and
```

```
                                                                     (SEQ ID NO: 2)
    1    ATGGTGTGCT TCCGCCTCTT CCCGGTTCCG GGCTCAGGGC TCGTTCTGGT CTGCCTAGTC

61    CTGGGAGCTG TGCGGTCTTA TGCATTGGAA CTTAATTTGA CAGATTCAGA AAATGCCACT

121    TGCCTTTATG CAAAATGGCA GATGAATTTC ACAGTTCGCT ATGAAACTAC AAATAAAACT

181    TATAAAACTG TAACCATTTC AGACCATGGC ACTGTGACAT ATAATGGAAG CATTTGTGGG

241    GATGATCAGA ATGGTCCCAA AATAGCAGTG CAGTTCGGAC CTGGCTTTTC CTGGATTGCG

301    AATTTTACCA AGGCAGCATC TACTTATTCA ATTGACAGCG TCTCATTTTC CTACAACACT

361    GGTGATAACA CAACATTTCC TGATGCTGAA GATAAAGGAA TTCTTACTGT TGATGAACTT

421    TTGGCCATCA GAATTCCATT GAATGACCTT TTTAGATGCA ATAGTTTATC AACTTTGGAA

481    AAGAATGATG TTGTCCAACA CTACTGGGAT GTTCTTGTAC AAGCTTTTGT CCAAAATGGC

541    ACAGTGAGCA CAAATGAGTT CCTGTGTGAT AAAGACAAAA CTTCAACAGT GGCACCCACC

601    ATACACACCA CTGTGCCATC TCCTACTACA ACACCTACTC CAAAGGAAAA ACCAGAAGCT

661    GGAACCTATT CAGTTAATAA TGGCAATGAT ACTTGTCTGC TGGCTACCAT GGGGCTGCAG

721    CTGAACATCA CTCAGGATAA GGTTGCTTCA GTTATTAACA TCAACCCCAA TACAACTCAC

781    TCCACAGGCA GCTGCCGTTC TCACACTGCT CTACTTAGAC TCAATAGCAG CACCATTAAG

841    TATCTAGACT TTGTCTTTGC TGTGAAAAAT GAAAACCGAT TTTATCTGAA GGAAGTGAAC

901    ATCAGCATGT ATTTGGTTAA TGGCTCCGTT TTCAGCATTG CAAATAACAA TCTCAGCTAC

961    TGGGATGCCC CCTGGGAAG TTCTTATATG TGCAACAAAG AGCAGACTGT TTCAGTGTCT

1021    GGAGCATTTC AGATAAATAC CTTTGATCTA AGGGTTCAGC CTTTCAATGT GACACAAGGA

1081    AAGTATTCTA CAGCCCAAGA GTGTTCGCTG GATGATGACA CCATTCTAAT CCCAATTATA

1141    GTTGGTGCTG GTCTTTCAGG CTTGATTATC GTTATAGTGA TTGCTTACGT AATTGGCAGA

1201    AGAAAAAGTT ATGCTGGATA TCAGACTCTG TAA.
```

Disclosed herein are modified polynucleotide sequences encoding an isoform of lysosome-associated membrane protein 2 (LAMP-2) or a functional variant thereof. In certain embodiments, the modified polynucleotide sequences comprise one or more of the following modifications as compared to the wild-type polynucleotide encoding the isoform of LAMP-2: codon-optimization, CpG depletion, removal of cryptic splice sites, or a reduced number of alternative open-reading frames (ORFs). In some embodiments, the modified polynucleotide encodes LAMP-2A, LAMP-2B, LAMP-2C or a functional variant of any of these isoforms.

In embodiments, the disclosure provides a polynucleotide sequence or transgene encoding LAMP-2B or a functional variant thereof comprising one or more nucleotide substitutions as compared to SEQ ID NO:2. In embodiments, the transgene shares at least 85%, 86%, 87%, 88%, 89%, 90%, 91%, 92%, 93%, 94%, 95%, 96%, 97%, 98%, 99%, or complete identity to a sequence selected from SEQ ID NOs: 3-5. The disclosure provides at least three illustrative variant transgene sequences encoding LAMP-2B (SEQ ID NOs: 3-5):

```
                                                            (SEQ ID NO: 3)
   1  ATGGTCTGCT TCAGACTGTT CCCTGTCCCT GGATCTGGTC TGGTGCTTGT GTGCTTGGTG
  61  CTGGGTGCTG TGAGATCCTA TGCCCTTGAG CTGAACCTGA CTGACTCAGA AAATGCCACT
 121  TGCCTGTATG CCAAGTGGCA GATGAACTTC ACTGTGAGAT ATGAGACTAC CAACAAGACC
 181  TACAAGACTG TGACCATCTC AGACCATGGC ACTGTCACCT ACAATGGATC AATCTGTGGT
 241  GATGATCAGA ATGGCCCAAA GATAGCAGTG CAGTTTGGGC CCGGTTTTTC CTGGATTGCT
 301  AACTTCACCA AGGCAGCCTC CACCTACAGC ATTGACTCAG TCAGCTTCAG CTACAACACT
 361  GGGGATAACA CCACCTTCCC TGACGCAGAG GACAAGGGAA TCCTTACTGT GGACGAACTC
 421  CTGGCAATCA GAATCCCCCT TAACGACCTG TTCAGATGCA ACTCCCTTTC AACCCTTGAA
 481  AAGAATGATG TGGTGCAACA CTATTGGGAC GTCCTGGTGC AAGCCTTTGT GCAGAATGGG
 541  ACAGTGAGTA CCAACGAGTT CCTCTGTGAC AAGGACAAGA CCAGCACTGT GGCCCCCACT
 601  ATCCACACCA CTGTGCCCAG CCCTACCACT ACCCCCACCC TAAAGAGAA GCCAGAAGCT
 661  GGAACCTACT CAGTCAACAA TGGAAATGAC ACATGCCTCC TTGCCACCAT GGGACTGCAG
 721  CTGAACATCA CTCAGGACAA GGTGGCCTCA GTGATTAACA TCAACCCTAA CACCACTCAT
 781  AGCACTGGGA GCTGCAGATC ACATACAGCT CTGCTGAGGC TCAACTCCTC CACCATCAAG
 841  TACCTGGACT TTGTGTTTGC TGTGAAGAAT GAGAACAGGT TCTACCTCAA GGAAGTGAAC
 901  ATTTCCATGT ACCTGGTCAA TGGTTCAGTG TTCTCTATTG CCAACAACAA TCTGAGCTAC
 961  TGGGATGCAC CCCTGGGATC CTCCTACATG TGCAACAAGG AGCAGACTGT GAGTGTGTCA
1021  GGTGCTTTTC AGATCAACAC TTTTGACCTG AGGGTGCAGC CCTTCAATGT GACTCAGGGA
1081  AAGTACTCCA CTGCACAAGA GTGTTCCTTG GATGATGACA CTATCCTCAT CCCCATTATT
1141  GTGGGAGCTG GACTGTCAGG ATTGATTATA GTGATTGTGA TTGCTTATGT GATTGGAAGG
1201  AGAAAGAGCT ATGCTGGCTA CCAGACCCTG TAA;
                                                            (SEQ ID NO: 4)
   1  ATGGTGTGCT TTAGACTGTT TCCTGTGCCT GGTTCAGGGC TGGTCCTGGT CTGTCTGGTG
  61  CTGGGGGCTG TCAGAAGCTA TGCCTTGGAG CTGAACCTCA CTGATAGTGA AAATGCCACT
 121  TGTCTGTATG CTAAGTGGCA GATGAACTTC ACTGTGAGAT ATGAAACCAC CAACAAGACT
 181  TACAAAACAG TGACCATCTC AGATCATGGA ACTGTGACCT ACAACGGCAG CATTTGTGGA
 241  GACGACCAGA ACGGACCAAA AATCGCTGTC CAATTTGGGC CTGGATTCTC CTGGATTGCC
 301  AATTTCACTA AGGCTGCCTC CACATATTCA ATTGACTCAG TGTCCTTCTC CTACAACACT
 361  GGGGACAACA CTACTTTCCC TGATGCTGAA GATAAGGGAA TCTTGACAGT GGATGAGCTG
 421  CTGGCTATCA GGATCCCTTT GAATGACCTG TTTAGGTGTA ATTCACTGAG CACTCTGGAG
 481  AAGAACGACG TGGTGCAGCA CTACTGGGAC GTGCTGGTGC AGGCCTTTGT GCAGAACGGC
 541  ACTGTGTCCA CCAACGAATT CCTGTGTGAT AAGGACAAAA CTTCCACTGT GGCACCTACA
 601  ATTCACACTA CTGTGCCTTC ACCTACCACC ACTCCAACTC AAAGGAAAA GCCTGAAGCA
 661  GGAACCTACT CTGTGAACAA TGGCAATGAT ACCTGTCTGT TGGCCACCAT GGGCCTCCAA
```

-continued

```
 721  CTGAACATTA CTCAGGACAA GGTGGCCTCA GTGATTAACA TTAACCCCAA CACTACCCAC

781  TCCACTGGCA GCTGTAGATC ACACACAGCC TTGCTCAGAC TGAATAGCAG CACCATCAAG

841  TATTTGGATT TTGTGTTTGC AGTGAAGAAT GAAACAGGT TCTACCTGAA GGAAGTCAAC

901  ATCTCAATGT ACCTGGTGAA CGGCTCAGTG TTCAGCATTG CCAACAACAA CCTCTCCTAT

961  TGGGACGCTC CACTGGGGAG CAGCTACATG TGTAACAAGG AACAGACTGT GTCAGTGTCA

1021  GGAGCCTTCC AGATTAACAC CTTTGATCTG AGGGTCCAAC CCTTTAATGT CACTCAAGGA

1081  AAGTATAGCA CTGCCCAGGA GTGCTCCCTG GATGATGACA CCATTCTGAT TCCAATCATT

1141  GTGGGTGCAG GACTTTCTGG GCTTATTATT GTGATTGTGA TTGCCTATGT GATTGGCAGA

1201  AGGAAATCCT ATGCAGGGTA CCAAACTCTG TAA;
and
```

(SEQ ID NO: 5)
```
   1  ATGGTCTGTT TTAGGCTGTT CCCTGTCCCT GGTTCAGGAC TGGTCTTAGT GTGTCTGGTG

61  CTTGGAGCTG TCAGAAGCTA TGCCCTGGAG CTGAACCTGA CTGACTCAGA AAATGCCACT

121  TGCCTGTATG CCAAGTGGCA GATGAACTTC ACTGTCAGAT ATGAAACCAC CAACAAGACC

181  TATAAGACTG TGACCATCTC AGACCATGGC ACTGTGACTT ACAATGGGTC AATTTGTGGA

241  GATGACCAGA ATGGCCCTAA GATAGCTGTC CAGTTTGGTC CAGGATTCAG CTGGATTGCC

301  AACTTCACCA AGGCAGCCAG CACCTACAGC ATTGACTCTG TGTCCTTCTC CTACAACACA

361  GGAGACAACA CCACTTTCCC TGATGCAGAG GACAAAGGTA TCCTGACTGT GGATGAGTTG

421  CTGGCAATCA GGATCCCACT GAACGATCTG TTCAGGTGCA ACTCACTGTC CACTCTGGAA

481  AAGAATGATG TGGTGCAGCA CTATTGGGAT GTGCTAGTCC AGGCCTTTGT CCAGAATGGG

541  ACTGTGTCAA CTAATGAGTT CCTGTGTGAC AAGGACAAGA CAAGCACTGT AGCCCCCACT

601  ATCCATACCA CAGTACCTAG CCCCACCACT ACTCCAACCC CAAGGAGAA GCCTGAGGCT

661  GGCACCTACT CAGTGAACAA TGGGAATGAC ACCTGTTTGC TGGCCACTAT GGGACTCCAA

721  CTGAACATCA CCCAGGACAA AGTGGCCTCT GTGATCAATA TCAATCCCAA CACCACCCAC

781  AGCACTGGGT CCTGCAGAAG CCACACTGCC CTCCTGAGGC TCAACTCATC AACTATCAAG

841  TACTTGGATT TTGTGTTTGC AGTGAAGAAT GAGAACAGAT TCTACCTCAA AGAGGTCAAC

901  ATTTCAATGT ACCTGGTGAA TGGGAGTGTG TTCTCCATTG CTAACAACAA CCTGAGCTAC

961  TGGGATGCCC CTCTGGGCTC CTCATACATG TGCAACAAGG AACAGACTGT GAGTGTGTCA

1021  GGGGCCTTCC AGATCAACAC TTTTGACCTG AGAGTGCAGC CCTTTAATGT GACACAGGGA

1081  AAGTACAGCA CTGCTCAGGA GTGCAGCCTG GATGATGACA CTATCCTGAT CCCTATCATT

1141  GTGGGGGCAG GCCTGTCTGG ACTCATTATT GTGATTGTGA TTGCCTATGT GATAGGGAGA

1201  AGGAAGTCTT ATGCTGGATA CCAGACCCTG TAA.
```

In an embodiment, the transgene shares at least 95% identity to a sequence selected from SEQ ID NOs: 3-5. In an embodiment, the transgene shares at least 99% identity to a sequence selected from SEQ ID NOs: 3-5. In an embodiment, the transgene comprises a sequence selected from SEQ ID NOs: 3-5. In an embodiment, the transgene shares at least 85%, 86%, 87%, 88%, 89%, 90%, 91%, 92%, 93%, 94%, 95%, 96%, 97%, 98%, 99%, or complete identity to SEQ ID NO: 3. In an embodiment, the transgene shares at least 85%, 86%, 87%, 88%, 89%, 90%, 91%, 92%, 93%, 94%, 95%, 96%, 97%, 98%, 99%, or complete identity to SEQ ID NO: 4. In an embodiment, the transgene shares at least 85%, 86%, 87%, 88%, 89%, 90%, 91%, 92%, 93%, 94%, 95%, 96%, 97%, 98%, 99%, or complete identity to SEQ ID NO: 5.

In some embodiments, the transgene is similar to or identical to a subsequence of any one of SEQ ID NOs: 3-5. In some embodiments, the transgene comprises a subsequence of any one of SEQ ID NOs: 3-5. In various embodiments, the subsequence may comprise any set of consecutive nucleotides (nt) in the full sequence having a length of at least about 50 nt, at least about 100 nt, at least about 150 nt, at least about 250 nt, at least about 200 nt, at least about 350 nt, at least about 450 nt, at least about 400 nt, at least about 450 nt, at least about 550 nt, at least about 600 nt, at least about 650 nt, at least about 600 nt, at least about 650 nt, at least about 700 nt, at least about 750 nt, at least about 800 nt, at least about 850 nt, at least about 900 nt, at least about 950 nt, or at least about 1000 nt.

In some embodiments, the transgene shares at least 95% identity to a subsequence that comprises nucleotides 1-500, 250-750, 500-1000, or 750-1240 of any one of SEQ ID NO: 3-5. In an embodiment, the transgene shares at least 99% identity to a subsequence that comprises nucleotides 1-500, 250-750, 500-1000, or 750-1240 of any one of SEQ ID NO: 3-5. In an embodiment, the transgene comprises a sequence that comprises nucleotides 1-500, 250-750, 500-1000, or 750-1240 of any one of SEQ ID NOs: 3-5. In embodiment, the transgene shares at least 85%, 86%, 87%, 88%, 89%, 90%, 91%, 92%, 93%, 94%, 95%, 96%, 97%, 98%, 99%, or complete identity to a subsequence that comprises nucleotides 1-500, 250-750, 500-1000, or 750-1240 of any one of SEQ ID NOs: 3-5. In embodiments, the transgene shares at least 85%, 86%, 87%, 88%, 89%, 90%, 91%, 92%, 93%, 94%, 95%, 96%, 97%, 98%, 99%, or complete identity to a subsequence that comprises nucleotides 1-500, 250-750, 500-1000, or 750-1240 of SEQ ID NO: 3. In embodiment, the transgene shares at least 85%, 86%, 87%, 88%, 89%, 90%, 91%, 92%, 93%, 94%, 95%, 96%, 97%, 98%, 99%, or complete identity to a subsequence that comprises nucleotides 1-500, 250-750, 500-1000, or 750-1240 of SEQ ID NO: 3.

In certain embodiments, the transgene encodes any of the various isoforms of LAMP-2, including any of LAMP-2A, LAMP-2B, or LAMP-2C, or a functional fragment or variant of any of these isoforms. Thus, in particular embodiments, the expression cassette is an optimized polynucleotide sequence encoding any of LAMP-2A, LAMP-2B, or LAMP-2C, or a functional fragment or variant thereof, which comprises one or more modifications as compared to the corresponding wild-type polynucleotide sequence, including one or more modification selected from: codon-optimization of the transgene sequence encoding LAMP-2A, LAMP-2B, or LAMP-2C; the expression cassette or transgene sequence contains fewer CpG sites than its corresponding wild-type sequence; the expression cassette or transgene sequence contains fewer CpG sites than its corresponding wild-type sequence; the expression cassette or transgene sequence contains fewer cryptic splice sites than its corresponding wild-type sequence; and/or the expression cassette or transgene sequence contains fewer open reading frames than its corresponding wild-type sequence. In particular embodiments, the optimized sequence is optimized for increased expression in human cells. The wild-type human polynucleotide sequences encoding the LAMP-2A and LAMP-2C isoforms are set forth in SEQ ID NOs: 29 and 30, respectively. The wild-type sequences of human LAMP-2A and LAMP-2C proteins are set forth in SEQ ID NOs: 34 and 35, respectively. The sequences of the wild-type LAMP-2 isoforms and coding sequences are also publicly available. While the specification describes specific embodiments with respect to LAMP-2B, it is understood that LAMP-2A or LAMP-2C could alternatively be used in each embodiment.

The coding sequences of wild-type LAMP-2A (SEQ ID NO: 29) and wild-type LAMP-2C (SEQ ID NO: 30) are 100% identical to the coding sequence of wild-type LAMP-2B (SEQ ID NO: 2) across at least nucleotides 1-1080. Accordingly, it will be readily recognized by those in the art that that transgenes, expression cassettes, and vectors disclosed herein can be adapted for expression of these isoforms of LAMP-2 by substituting the 3' end (nucleotides 1081—end) of either of LAMP-2A (SEQ ID NO: 29) or wild-type LAMP-2C (SEQ ID NO: 30) in place of nucleotides 1081-1233 of LAMP-2B (e.g., an optimized LAMP-2B of any of SEQ ID NO: 3-5). For example, embodiments of the invention utilize nucleotides 1-1080 of the optimized LAMP-2B gene sequences, SEQ ID NOs: 3-5, which are, respectively, SEQ ID NOs: 31-33.

In an embodiment, the transgene shares at least 95% identity to a sequence selected from SEQ ID NOs: 31-33. In an embodiment, the transgene shares at least 99% identity to a sequence selected from SEQ ID NOs: 31-33. In an embodiment, the transgene comprises a sequence selected from SEQ ID NOs: 31-33. In an embodiment, the transgene shares at least 85%, 86%, 87%, 88%, 89%, 90%, 91%, 92%, 93%, 94%, 95%, 96%, 97%, 98%, 99%, or complete identity to SEQ ID NO: 31. In an embodiment, the transgene shares at least 85%, 86%, 87%, 88%, 89%, 90%, 91%, 92%, 93%, 94%, 95%, 96%, 97%, 98%, 99%, or complete identity to SEQ ID NO: 32. In an embodiment, the transgene shares at least 85%, 86%, 87%, 88%, 89%, 90%, 91%, 92%, 93%, 94%, 95%, 96%, 97%, 98%, 99%, or complete identity to SEQ ID NO: 33. In some cases, the transgene has a polynucleotide sequence that is different from the polynucleotide sequence of a reference sequence, e.g., a "native" or "wild-type" LAMP-2B sequence. In some embodiments, the transgene shares at most 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or 95% identity with a reference sequence. In some embodiments, the reference sequence is SEQ ID NO: 2. For example, SEQ ID NO: 3 shares 78.5% identity to SEQ ID NO: 2.

In some cases, the transgene has a polynucleotide sequence that is different from the polynucleotide sequence of a reference sequence, e.g., a "native" or "wild-type" LAMP-2A sequence. In some embodiments, the transgene shares at most 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or 95% identity with a reference sequence. In some embodiments, the reference sequence is the wild-type human LAMP-2A sequence set forth in SEQ ID NO: 29.

In some cases, the transgene has a polynucleotide sequence that is different from the polynucleotide sequence of a reference sequence, e.g., a "native" or "wild-type" LAMP-2C sequence. In some embodiments, the transgene shares at most 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or 95% identity with a reference sequence. In some embodiments, the reference sequence is the wild-type human LAMP-2A sequence set forth in SEQ ID NO: 30.

In an embodiment, the transgene is codon-optimized for expression in a human host cell. In an embodiment, the transgene coding sequence is modified, or "codon optimized" to enhance expression by replacing infrequently represented codons with more frequently represented codons. The coding sequence is the portion of the mRNA sequence that encodes the amino acids for translation. During translation, each of 61 trinucleotide codons are translated to one of 20 amino acids, leading to a degeneracy, or redundancy, in the genetic code. However, different cell types, and different animal species, utilize tRNAs (each bearing an anticodon) coding for the same amino acids at different frequencies. When a gene sequence contains codons that are infrequently represented by the corresponding tRNA, the ribosome translation machinery may slow, impeding efficient translation. Expression can be improved via "codon optimization" for a particular species, where the coding sequence is altered to encode the same protein sequence, but utilizing codons that are highly represented, and/or utilized by highly expressed human proteins (Cid-Arregui et al., 2003; J. Virol. 77: 4928).

In some embodiments, the coding sequence of the transgene is modified to replace codons infrequently expressed in mammal or in primates with codons frequently expressed in primates. For example, in some embodiments, the transgene encodes a polypeptide having at least 85% sequence identity to a reference polypeptide (e.g. wild-type LAMP-2B; SEQ ID NO: 3)—for example, at least 90% sequence identity, at least 95% sequence identity, at least 98% identity, or at least 99% identity to the reference polypeptide—wherein at least one codon of the coding sequence has a higher tRNA frequency in humans than the corresponding codon in the sequence disclosed above or herein.

In an embodiment, the transgene comprises fewer alternative open reading frames than SEQ ID: 2. In an embodiment, the transgene is modified to enhance expression by termination or removal of open reading frames (ORFs) that do not encode the desired transgene. An open reading frame (ORF) is the nucleic acid sequence that follows a start codon and does not contain a stop codon. ORFs may be in the forward or reverse orientation, and may be "in frame" or "out of frame" compared with the gene of interest. Such open reading frames have the potential to be expressed in an expression cassette alongside the gene of interest, and could lead to undesired adverse effects. In some embodiments the transgene has been modified to remove open reading frames by further altering codon usage. This may be done by eliminating one or more start codons (ATG) and/or introducing one or more stop codons (TAG, TAA, or TGA) in reverse orientation or out-of-frame to the desired ORF, while preserving the encoded amino acid sequence and, optionally, maintaining highly utilized codons in the gene of interest (i.e., avoiding codons with frequency <20%).

In some embodiments, the expression cassette comprises at most one, at most two, at most three, at most four, or at most five start codons 5' to the start codon of the transgene. In some embodiments, the expression cassette comprises no start codon 5' to the start codon of the transgene. In some embodiments, one or more ATG codons in the 5' UTR, the promoter, the enhance, the promoter/enhancer element, or other sequences 5' to the start codon of the transgene remain after one or more cryptic start sites are removed. In some embodiments, the expression cassette comprises no cryptic starts sites upstream of transgene to generate erroneous mRNAs.

In variations of the present disclosure, the transgene coding sequence may be optimized by either codon optimization or removal of non-transgene ORFs or using both techniques. In some cases, one removes or minimizes non-transgene ORFs after codon optimization in order to remove ORFs introduced during codon optimization.

In an embodiment, the transgene contains fewer CpG sites than SEQ ID: 2. Without being bound by theory, it is believed that the presence of CpG sites in a polynucleotide sequence is associated with the undesirable immunological responses of the host against a viral vector comprising the polynucleotide sequence. In some embodiments, the transgene is designed to reduce the number of CpG sites. Exemplary methods are provides in U.S. Patent Application Publication No. US20020065236A1.

In an embodiment, the transgene contains fewer cryptic splice sites than SEQ ID: 2. For the optimization, GeneArt® software may be used, e.g., to increase the GC content and/or remove cryptic splice sites in order to avoid transcriptional silencing and, therefore, increase transgene expression. Alternatively, any optimization method known in the art may be used. Removal of cryptic splice sites is described, for example, in International Patent Application Publication No. WO2004015106A1.

Also disclosed herein are expression cassettes and gene therapy vectors encoding LAMP-2B. In certain embodiments, the expression cassettes and gene therapy vectors comprise a codon-optimized or variant LAMP-2B polynucleotide sequence or transgene sequence disclosed herein.

In particular embodiments, an expression cassette or gene therapy vector encoding LAMP-2B comprises: a consensus optimal Kozak sequence, a full-length polyadenylation (polyA) sequence (or substitution of full-length polyA by a truncated polyA), and minimal or no upstream (i.e. 5') or cryptic start codons (i.e. ATG sites). In some embodiments, the expression cassette comprises no start site 5' to the transgene capable of generating alternative mRNAs. In certain embodiments, the expression cassette or gene therapy vector comprises a sequence encoding LAMP-2B, e.g., a codon-optimized or variant LAMP-2B polynucleotide sequence or transgene sequence disclosed herein.

In some cases, the expression cassette contains two or more of a first inverted terminal repeat, an enhancer/promoter region, a consensus optimal Kozak sequence, a transgene (e.g., a transgene encoding a LAMP-2B disclosed herein), a 3' untranslated region including a full-length polyA sequence, and a second inverted terminal repeat. In some embodiments, one or both of the inverted terminal repeats (ITRs) are AAV1, AAV2, AAV3, AAV4, AAV5, AAV6, AAV7, or AAV9 ITRs, or any one ITR known in the art. In some embodiments, the expression cassette comprises exactly two ITRs. In some embodiments, both ITRs are AAV2, AAV5, or AAV9 ITRs. In some embodiments, both ITRs are AAV2 ITRs.

In an embodiment, the expression cassette comprises a Kozak sequence operatively linked to the transgene. In an embodiment, the Kozak sequence is a consensus optimal Kozak sequence comprising or consisting of SEQ ID NO: 6:

```
                                              (SEQ ID NO: 6)
                GCCGCCACCATGG.
```

In various embodiments, the expression cassette comprises an alternative Kozak sequence operatively linked to the transgene. In an embodiment, the Kozak sequence is an alternative Kozak sequence comprising or consisting of any one of SEQ ID NOs. 14-18:

```
                                              (SEQ ID NO: 14)
             (gcc)gccRccAUGG;

(SEQ ID NO: 15)
                AGNNAUGN;

(SEQ ID NO: 16)
                ANNAUGG;

(SEQ ID NO: 17)
                ACCAUGG;

(SEQ ID NO: 18)
                GACACCAUGG.
```

In some embodiments, the expression cassette comprises no Kozak sequence.

In SEQ ID NO: 14, a lower-case letter denotes the most common base at a position where the base can nevertheless vary; an upper-case letter indicate a highly conserved base;

indicates adenine or guanine. In SEQ ID NO: 14, the sequence in parentheses (gcc) is optional. In SEQ ID NOs: 15-17, 'N' denotes any base.

A variety of sequences can be used in place of this consensus optimal Kozak sequence as the translation-initiation site and it is within the skill of those in the art to identify and test other sequences. See Kozak M. An analysis of vertebrate mRNA sequences: intimations of translational control. *J. Cell Biol.* 115 (4): 887-903 (1991).

In an embodiment, the expression cassette comprises a full-length polyA sequence operatively linked to the transgene. In an embodiment, the full-length polyA sequence comprises SEQ ID NO: 7:

In some cases, expression of the transgene is increased by ensuring that the expression cassette does not contain competing ORFs. In an embodiment, the expression cassette comprises no start codon within 20, 30, 40, 50, 60, 70, 80, 90, 100, 200, 300, 400, or 500 base pairs 5' of the start codon of the transgene. In some embodiment, the expression cassette comprises no start codon 5' of the start codon of the transgene. In some embodiments, the expression cassette comprises no start site 5' to the transgene capable of generating alternative mRNAs.

In an embodiment, the expression cassette comprises operatively linked, in the 5' to 3' direction, a first inverted terminal repeat, an enhancer/promoter region, introns, a

```
                                                          (SEQ ID NO: 7)
  1   TGGCTAATAA AGGAAATTTA TTTTCATTGC AATAGTGTGT TGGAATTTTT TGTGTCTCTC

61   ACTCGGAAGG ACATATGGGA GGGCAAATCA TTTAAAACAT CAGAATGAGT ATTTGGTTTA

121   GAGTTTGGCA ACATATGCCC ATATGCTGGC TGCCATGAAC AAAGGTTGGC TATAAAGAGG

181   TCATCAGTAT ATGAAACAGC CCCCTGCTGT CCATTCCTTA TTCCATAGAA AAGCCTTGAC

241   TTGAGGTTAG ATTTTTTTA TATTTTGTTT TGTGTTATTT TTTTCTTTAA CATCCCTAAA

301   ATTTTCCTTA CATGTTTTAC TAGCCAGATT TTTCCTCCTC TCCTGACTAC TCCCAGTCAT

361   AGCTGTCCCT CTTCTCTTAT GGAGATC.
```

Various alternative polyA sequences may be used in expression cassettes of the present disclosure, including without limitation, bovine growth hormone polyadenylation signal (bGHpA) (SEQ ID NO: 19), the SV40 early/late polyadenylation signal (SEQ ID NO: 20), and human growth hormone (HGH) polyadenylation signal (SEQ ID NO: 21):

consensus optimal Kozak sequence, the transgene, a 3' untranslated region including a full-length polyA sequence, and a second inverted terminal repeat, wherein the expression cassette comprises no start site 5' to the transgene capable of generating alternative mRNAs.

In some embodiments, the enhancer/promoter region comprises, in the 5' to 3' direction: a CMV IE enhancer and

```
                                                          (SEQ ID NO: 19)
  1   TCGACTGTGC CTTCTAGTTG CCAGCCATCT GTTGTTTGCC CCTCCCCCGT GCCTTCCTTG

61   ACCCTGGAAG GTGCCACTCC CACTGTCCTT TCCTAATAAA ATGAGGAAAT TGCATCGCAT

121   TGTCTGAGTA GGTGTCATTC TATTCTGGGG GGTGGGGTGG GGCAGGACAG CAAGGGGGAG

181   GATTGGGAGG ACAATAGCAG GCATGCTGGG GATGCGGTGG GCTCTATGGC TTCTG;

(SEQ ID NO: 20)
  1   CAGACATGAT AAGATACATT GATGAGTTTG GACAAACCAC AACTAGAATG CAGTGAAAAA

61   AATGCTTTAT TTGTGAAATT TGTGATGCTA TTGCTTTATT TGTAACCATT ATAAGCTGCA

121   ATAAACAAGT TAACAACAAC AATTGCATTC ATTTTATGTT TCAGGTTCAG GGGGAGATGT

181   GGGAGGTTTT TTAAAGCAAG TAAAACCTCT ACAAATGTGG TA;

(SEQ ID NO: 21)
  1   CTGCCCGGGT GGCATCCCTG TGACCCCTCC CCAGTGCCTC TCCTGGCCCT GGAAGTTGCC

61   ACTCCAGTGC CCACCAGCCT TGTCCTAATA AAATTAAGTT GCATCATTTT GTCTGACTAG

121   GTGTCCTTCT ATAATATTAT GGGGTGGAGG GGGTGGTAT GGAGCAAGGG GCCCAAGTTG

181   GGAAGAAACC TGTAGGGCCT GC.
```

In some embodiments, the expression cassette comprises an active fragment of a polyA sequence. In particular embodiments, the active fragment of the polyA sequence comprises or consists of less than 20 base pair (bp), less than 50 bp, less than 100 bp, or less than 150 bp, e.g., of any of the polyA sequences disclosed herein.

a chicken beta-actin promoter. In an embodiment, the enhancer/promoter region comprises a CAG promoter (SEQ ID NO: 22). As used herein "CAG promoter" refers to a polynucleotide sequence comprising a CMV early enhancer element, a chicken beta-actin promoter, the first exon and first intron of the chicken beta-actin gene, and a splice acceptor from the rabbit beta-globin gene.

```
                                                             (SEQ ID NO: 22)
   1  CTAGTCGACA TTGATTATTG ACTAGTTATT AATAGTAATC AATTACGGGG TCATTAGTTC
  61  ATAGCCCATA TATGGAGTTC CGCGTTACAT AACTTACGGT AAATGGCCCG CCTGGCTGAC
 121  CGCCCAACGA CCCCCGCCCA TTGACGTCAA TAATGACGTA TGTTCCCATA GTAACGCCAA
 181  TAGGGACTTT CCATTGACGT CAATGGGTGG AGTATTTACG GTAAACTGCC CACTTGGCAG
 241  TACATCAAGT GTATCATATG CCAAGTACGC CCCCTATTGA CGTCAATGAC GGTAAATGGC
 301  CCGCCTGGCA TTATGCCCAG TACATGACCT TATGGGACTT TCCTACTTGG CAGTACATCT
 361  ACGTATTAGT CATCGCTATT ACCATGGTCG AGGTGAGCCC CACGTTCTGC TTCACTCTCC
 421  CCATCTCCCC CCCCTCCCCA CCCCCAATTT TGTATTTATT TATTTTTTAA TTATTTTGTG
 481  CAGCGATGGG GGCGGGGGGG GGGGGGGGGC GCGCGCCAGG CGGGGCGGGG CGGGGCGAGG
 541  GGCGGGGCGG GGCGAGGCGA AGAGGTGCGG CGGCAGCCAA TCAGAGCGGC GCGCTCCGAA
 601  AGTTTCCTTT TATGGCGAGG CGGCGGCGGC GGCGGCCCTA TAAAAGCGA  AGCGCGCGGC
 661  GGGCGGGAGT CGCTGCGCGC TGCCTTCGCC CCGTGCCCCG CTCCGCCGCC GCCTCGCGCC
 721  GCCCGCCCCG GCTCTGACTG ACCGCGTTAC TCCCACAGGT GAGCGGGCGG GACGGCCCTT
 781  CTCCTCCGGG CTGTAATTAG CGCTTGGTTT AATGACGGCT TGTTTCTTTT CTGTGGCTGC
 841  GTGAAAGCCT TGAGGGGCTC CGGGAGGGCC CTTTGTGCGG GGGGAGCGGC TCGGGGGTG
 901  CGTGCGTGTG TGTGTGCGTG GGGAGCGCCG CGTGCGGCTC CGCGCTGCCC GGCGGCTGTG
 961  AGCGCTGCGG GCGCGGCGCG GGGCTTTGTG CGCTCCGCAG TGTGCGCGAG GGGAGCGCGG
1021  CCGGGGGCGG TGCCCCGCGG TGCGGGGGGG GCTGCGAGGG GAACAAAGGC TGCGTGCGGG
1081  GTGTGTGCGT GGGGGGGTGA GCAGGGGGTG TGGGCGCGTC GGTCGGGCTG CAACCCCCCC
1141  TGCACCCCCC TCCCCGAGTT GCTGAGCACG GCCCGGCTTC GGGTGCGGGG CTCCGTACGG
1201  GGCGTGGCGC GGGGCTCGCC GTGCCGGGCG GGGGGTGGCG GCAGGTGGGG GTGCCGGGCG
1261  GGGCGGGGCC GCCTCGGGCC GGGGAGGGCT CGGGGGAGGG GCGCGGCGGC CCCCGGAGCG
1321  CCGGCGGCTG TCGAGGCGCG GCGAGCCGCA GCCATTGCCT TTTATGGTAA TCGTGCGAGA
1381  GGGCGCAGGG ACTTCCTTTG TCCCAAATCT GTGCGGAGCC GAAATCTGGG AGGCGCCGCC
1441  GCACCCCCTC TAGCGGGCGC GGGGCGAAGC GGTGCGGCGC CGGCAGGAAG GAAATGGGCG
1501  GGGAGGGCCT TCGTGCGTCG CCGCGCCGCC GTCCCCTTCT CCCTCTCCAG CCTCGGGGCT
1561  GTCCGCGGGG GGACGGCTGC CTTCGGGGGG GACGGGGCAG GGCGGGGTTC GGCTTCTGGC
1621  GTGTGACCGG CGGCTCTAGA GCCTCTGCTA ACCATGTTCA TGCCTTCTTC TTTTTCCTAC
1681  AGCTCCTGGG CAACGTGCTG GTTATTGTGC TGTCTCATCA TTTTGGCAAA.
```

In some embodiments, the enhancer/promoter region comprises a ubiquitous promoter. In some embodiments, the enhancer/promoter region comprises a CMV promoter (SEQ. ID NO: 23), an SV40 promoter (SEQ ID NO: 24), a PGK promoter (SEQ ID NO: 25), and/or a human beta-actin promoter (SEQ ID NO: 26). In some embodiments, the enhancer/promoter region comprises a polynucleotide that shares at least 75%, 80%, 85%, 90%, 95%, 96%, 97%, 98%, 99%, or 100% sequence identity with any one of SEQ ID NOs: 23-26:

```
                                                             (SEQ ID NO: 23)
   1  GTGATGCGGT TTTGGCAGTA CATCAATGGG CGTGGATAGC GGTTTGACTC ACGGGGATTT
  61  CCAAGTCTCC ACCCCATTGA CGTCAATGGG AGTTTGTTTT GGCACCAAAA TCAACGGGAC
 121  TTTCCAAAAT GTCGTAACAA CTCCGCCCCA TTGACGCAAA TGGGCGGTAG CGTGTACGG
 181  TGGGAGGTCT ATATAAGCAG AGCT;
                                                             (SEQ ID NO: 24)
   1  GGTGTGGAAA GTCCCCAGGC TCCCCAGCAG GCAGAAGTAT GCAAAGCATG CATCTCAATT
  61  AGTCAGCAAC CAGGTGTGGA AAGTCCCCAG GCTCCCCAGC AGGCAGAAGT ATGCAAAGCA
```

-continued

```
121  TGCATCTCAA TTAGTCAGCA ACCATAGTCC CGCCCCTAAC TCCGCCCATC CCGCCCCTAA
181  CTCCGCCCAG TTCCGCCCAT TCTCCGCCCC ATGGCTGACT AATTTTTTTT ATTTATGCAG
241  AGGCCGAGGC CGCCTCGGCC TCTGAGCTAT TCCAGAAGTA GTGAGGAGGC TTTTTTGGAG
301  GCCTAGGCTT TTGCAAA;
```

(SEQ ID NO: 25)
```
  1  GGGTAGGGGA GGCGCTTTTC CCAAGGCAGT CTGGAGCATG CGCTTTAGCA GCCCCGCTGG
 61  GCACTTGGCG CTACACAAGT GGCCTCTGGC CTCGCACACA TTCCACATCC ACCGGTAGGC
121  GCCAACCGGC TCCGTTCTTT GGTGGCCCCT TCGCGCCACC TTCTACTCCT CCCCTAGTCA
181  GGAAGTTCCC CCCCGCCCCG CAGCTCGCGT CGTGCAGGAC GTGACAAATG GAAGTAGCAC
241  GTCTCACTAG TCTCGTGCAG ATGGACAGCA CCGCTGAGCA ATGGAAGCGG GTAGGCCTTT
301  GGGGCAGCGG CCAATAGCAG CTTTGCTCCT TCGCTTTCTG GGCTCAGAGG CTGGGAAGGG
361  GTGGGTCCGG GGGCGGGCTC AGGGGCGGGC TCAGGGGCGG GGCGGGCGCC CGAAGGTCCT
421  CCGGAGGCCC GGCATTCTGC ACGCTTCAAA AGCGCACGTC TGCCGCGCTG TTCTCCTCTT
481  CCTCATCTCC GGGCCTTTCG;
```

(SEQ ID NO: 26)
```
   1  CCTGCAGGGC CCACTAGTTC CATGTCCTTA TATGGACTCA TCTTTGCCTA TTGCGACACA
  61  CACTCAATGA ACACCTACTA CGCGCTGCAA AGAGCCCCGC AGGCCTGAGG TGCCCCCACC
 121  TCACCACTCT TCCTATTTTT GTGTAAAAAT CCAGCTTCTT GTCACCACCT CCAAGGAGGG
 181  GGAGGAGGAG GAAGGCAGGT TCCTCTAGGC TGAGCCGAAT GCCCCTCTGT GGTCCCACGC
 241  CACTGATCGC TGCATGCCCA CCACCTGGGT ACACACAGTC TGTGATTCCC GGAGCAGAAC
 301  GGACCCTGCC CACCCGGTCT TGTGTGCTAC TCAGTGGACA GACCCAAGGC AAGAAAGGGT
 361  GACAAGGACA GGGTCTTCCC AGGCTGGCTT TGAGTTCCTA GCACCGCCCC GCCCCCAATC
 421  CTCTGTGGCA CATGGAGTCT TGGTCCCCAG AGTCCCCAG CGGCCTCCAG ATGGTCTGGG
 481  AGGGCAGTTC AGCTGTGGCT GCGCATAGCA GACATACAAC GGACGGTGGG CCCAGACCCA
 541  GGCTGTGTAG ACCCAGCCCC CCCGCCCCGC AGTGCCTAGG TCACCCACTA ACGCCCCAGG
 601  CCTGGTCTTG GCTGGGCGTG ACTGTTACCC TCAAAAGCAG GCAGCTCCAG GTAAAAGGT
 661  GCCCTGCCCT GTAGAGCCCA CCTTCCTTCC CAGGGCTGCG GCTGGGTAGG TTTGTAGCCT
 721  TCATCACGGG CCACCTCCAG CCACTGGACC GCTGGCCCCT GCCCTGTCCT GGGGAGTGTG
 781  GTCCTGCGAC TTCTAAGTGG CCGCAAGCCA CCTGACTCCC CAACACCAC ACTCTACCTC
 841  TCAAGCCCAG GTCTCTCCCT AGTGACCCAC CCAGCACATT TAGCTAGCTG AGCCCCACAG
 901  CCAGAGGTCC TCAGGCCCTG CTTTCAGGGC AGTTGCTCTG AAGTCGGCAA GGGGAGTGA
 961  CTGCCTGGCC ACTCCATGCC CTCCAAGAGC TCCTTCTGCA GGAGCGTACA GAACCCAGGG
1021  CCCTGGCACC CGTGCAGACC CTGGCCCACC CCACCTGGGC GCTCAGTGCC AAGAGATGT
1081  CCACACCTAG GATGTCCCGC GGTGGGTGGG GGGCCCGAGA GACGGGCAGG CCGGGGGCAG
1141  GCCTGGCCAT GCGGGGCCGA ACCGGGCACT GCCCAGCGTG GGGCGCGGGG GCCACGGCGC
1201  GCGCCCCCAG CCCCCGGGCC CAGCACCCCA AGGCGGCCAA CGCCAAAACT CTCCCTCCTC
1261  CTCTTCCTCA ATCTCGCTCT CGCTCTTTTT TTTTTTCGCA AAAGGAGGGG AGAGGGGTA
1321  AAAAAATGCT GCACTGTGCG GCGAAGCCGG TGAGTGAGCG CGCGGGGCC AATCAGCGTG
1381  CGCCGTTCCG AAAGTTGCCT TTTATGGCTC GAGCGGCCGC GGCGGCGCCC TATAAAACCC
1441  AGCGGCGCGA CGCGCCACCA CCGCCGAGAC CGCGTCCGCC CCGCGAGCAC AGAGCCTCGC
1501  CTTTGCCGAT CCGCCGCCCG TCCACACCCG CCGCCAGGTA AGCCCGGCCA GCCGACCGGG
```

```
1561  GCAGGCGGCT CACGGCCCGG CCGCAGGCGG CCGCGGCCCC TTCGCCCGTG CAGAGCCGCC

1621  GTCTGGGCCG CAGCGGGGGG CGCATGGGGG GGGAACCGGA CCGCCGTGGG GGGCGCGGGA

1681  GAAGCCCCTG GGCCTCCGGA GATGGGGGAC ACCCCACGCC AGTTCGGAGG CGCGAGGCCG

1741  CGCTCGGGAG GCGCGCTCCG GGGGTGCCGC TCTCGGGGCG GGGGCAACCG GCGGGGTCTT

1801  TGTCTGAGCC GGGCTCTTGC CAATGGGGAT CGCAGGGTGG GCGCGGCGGA GCCCCCGCCA

1861  GGCCCGGTGG GGGCTGGGGC GCCATTGCGC GTGCGCGCTG GTCCTTTGGG CGCTAACTGC

1921  GTGCGCGCTG GGAATTGGCG CTAATTGCGC GTGCGCGCTG GGACTCAAGG CGCTAACTGC

1981  GCGTGCGTTC TGGGGCCCGG GGTGCCGCGG CCTGGGCTGG GGCGAAGGCG GGCTCGGCCG

2041  GAAGGGGTGG GGTCGCCGCG GCTCCCGGGC GCTTGCGCGC ACTTCCTGCC CGAGCCGCTG

2101  GCCGCCCGAG GGTGTGGCCG CTGCGTGCGC GCGCGCCGAC CCGGCGCTGT TTGAACCGGG

2161  CGGAGGCGGG GCTGGCGCCC GGTTGGGAGG GGGTTGGGGC CTGGCTTCCT GCCGCGCGCC

2221  GCGGGACGC CTCCGACCAG TGTTTGCCTT TTATGGTAAT AACGCGGCCG GCCCGGCTTC

2281  CTTTGTCCCC AATCTGGGCG CGCGCCGGCG CCCCCTGGCG GCCTAAGGAC TCGGCGCGCC

2341  GGAAGTGGCC AGGGCGGGGG CGACCTCGGC TCACAGCGCG CCCGGCTATT CTCGCAGCTC

2401  ACC.
```

Further exemplary promoters include, but are not limited to, human Elongation Factor 1 alpha promoter (EFS), SV40 early promoter, mouse mammary tumor virus long terminal repeat (LTR) promoter; adenovirus major late promoter (Ad MLP); a herpes simplex virus (HSV) promoter, an endogenous cellular promoter that is heterologous to the gene of interest, a cytomegalovirus (CMV) promoter such as the CMV immediate early promoter region (CMVIE), a Rous sarcoma virus (RSV) promoter, synthetic promoters, hybrid promoters, and the like In some embodiments, the 3' UTR comprises a polynucleotide (WPRE element) that shares at least 75%, 80%, 85%, 90%, 95%, 96%, 97%, 98%, 99%, or 100% sequence identity with SEQ ID NO: 27:

```
                                                              (SEQ ID NO: 27)
  1  ATTCGAGCAT CTTACCGCCA TTTATTCCCA TATTTGTTCT GTTTTTCTTG ATTTGGGTAT

61  ACATTTAAAT GTTAATAAAA CAAAATGGTG GGGCAATCAT TTACATTTTT AGGGATATGT

121  AATTACTAGT TCAGGTGTAT TGCCACAAGA CAAACATGTT AAGAAACTTT CCCGTTATTT

181  ACGCTCTGTT CCTGTTAATC AACCTCTGGA TTACAAAATT TGTGAAAGAT TGACTGATAT

241  TCTTAACTAT GTTGCTCCTT TTACGCTGTG TGGATATGCT GCTTTAATGC CTCTGTATCA

301  TGCTATTGCT TCCCGTACGG CTTTCGTTTT CTCCTCCTTG TATAAATCCT GGTTGCTGTC

361  TCTTTATGAG GAGTTGTGGC CCGTTGTCCG TCAACGTGGC GTGGTGTGCT CTGTGTTTGC

421  TGACGCAACC CCCACTGGCT GGGGCATTGC CACCACCTGT CAACTCCTTT CTGGGACTTT

481  CGCTTTCCCC CTCCCGATCG CCACGGCAGA ACTCATCGCC GCCTGCCTTG CCCGCTGCTG

541  GACAGGGGCT AGGTTGCTGG GCACTGATAA TTCCGTGGTG TTGTCGGGGA AGGGCC.
```

In some embodiment, the expression cassette shares at least 95% identity to a sequence selected from SEQ ID NOs: 8-10. In an embodiment, the expression cassette shares complete identity to a sequence selected from SEQ ID NOs: 8-10, or shares at least 80%, at least 85%, at least 90%, at least 95%, at least 98%, or at least 99% identity to a sequence selected from SEQ ID NOs: 8-10:

(SEQ ID NO: 8)

```
   1  CTGCGCGCTC GCTCGCTCAC TGAGGCCGCC CGGGCAAAGC CCGGGCGTCG GGCGACCTTT
  61  GGTCGCCCGG CCTCAGTGAG CGAGCGAGCG CGCAGAGAGG GAGTGGCCAA CTCCATCACT
 121  AGGGGTTCCT TGTAGTTAAT GATTAACCCG CCATGCTACT TATCTACCAG GGTAATGGGG
 181  ATCCTCTAGA ACTATAGCTA GTCGACATTG ATTATTGACT AGTTATTAAT AGTAATCAAT
 241  TACGGGGTCA TTAGTTCATA GCCCATATAT GGAGTTCCGC GTTACATAAC TTACGGTAAA
 301  TGGCCCGCCT GGCTGACCGC CCAACGACCC CCGCCCATTG ACGTCAATAA TGACGTATGT
 361  TCCCATAGTA ACGCCAATAG GGACTTTCCA TTGACGTCAA TGGGTGGAGT ATTTACGGTA
 421  AACTGCCCAC TTGGCAGTAC ATCAAGTGTA TCATATGCCA AGTACGCCCC CTATTGACGT
 481  CAATGACGGT AAATGGCCCG CCTGGCATTA TGCCCAGTAC ATGACCTTAT GGGACTTTCC
 541  TACTTGGCAG TACATCTACG TATTAGTCAT CGCTATTACC ATGGTCGAGG TGAGCCCCAC
 601  GTTCTGCTTC ACTCTCCCCA TCTCCCCCCC CTCCCCACCC CCAATTTTGT ATTTATTTAT
 661  TTTTTAATTA TTTTGTGCAG CGATGGGGGC GGGGGGGGGG GGGGGCGCG  CGCCAGGCGG
 721  GGCGGGGCGG GGCGAGGGGC GGGGCGGGGC GAGGCGGAGA GGTGCGGCGG CAGCCAATCA
 781  GAGCGGCGCG CTCCGAAAGT TTCCTTTTAT GGCGAGGCGG CGGCGGCGGC GGCCCTATAA
 841  AAAGCGAAGC GCGCGGCGGG CGGGAGTCGC TGCGCGCTGC CTTCGCCCCG TGCCCCGCTC
 901  CGCCGCCGCC TCGCGCCGCC CGCCCCGGCT CTGACTGACC GCGTTACTCC CACAGGTGAG
 961  CGGGCGGGAC GGCCCTTCTC CTCCGGGCTG TAATTAGCGC TTGGTTTAAT GACGGCTTGT
1021  TTCTTTTCTG TGGCTGCGTG AAAGCCTTGA GGGGCTCCGG GAGGGCCCTT TGTGCGGGGG
1081  GAGCGGCTCG GGGGTGCGT  GCGTGTGTGT GTGCGTGGGG AGCGCCGCGT GCGGCTCCGC
1141  GCTGCCCGGC GGCTGTGAGC GCTGCGGGCG CGGCGCGGGG CTTTGTGCGC TCCGCAGTGT
1201  GCGCGAGGGG AGCGCGGCCG GGGGCGGTGC CCCGCGGTGC GGGGGGGGCT GCGAGGGGAA
1261  CAAAGGCTGC GTGCGGGGTG TGTGCGTGGG GGGGTGAGCA GGGGGTGTGG GCGCGTCGGT
1321  CGGGCTGCAA CCCCCCCTGC ACCCCCCTCC CCGAGTTGCT GAGCACGGCC CGGCTTCGGG
1381  TGCGGGGCTC CGTACGGGGC GTGGCGCGGG GCTCGCCGTG CCGGGCGGGG GGTGGCGGCA
1441  GGTGGGGGTG CCGGGCGGGG CGGGGCCGCC TCGGGCCGGG GAGGGCTCGG GGGAGGGGCG
1501  CGGCGGCCCC CGGAGCGCCG GCGGCTGTCG AGGCGCGGCG AGCCGCAGCC ATTGCCTTTT
1561  ATGGTAATCG TGCGAGAGGG CGCAGGGACT TCCTTTGTCC CAAATCTGTG CGGAGCCGAA
1621  ATCTGGGAGG CGCCGCCGCA CCCCCTCTAG CGGGCGCGGG GCGAAGCGGT GCGGCGCCGG
1681  CAGGAAGGAA ATGGGCGGGA GGGCCTTCG  TGCGTCGCCG CGCCGCCGTC CCCTTCTCCC
1741  TCTCCAGCCT CGGGGCTGTC CGCGGGGGGA CGGCTGCCTT CGGGGGGGAC GGGGCAGGGC
1801  GGGGTTCGGC TTCTGGCGTG TGACCGGCGG CTCTAGAGCC TCTGCTAACC ATGTTCATGC
1861  CTTCTTCTTT TTCCTACAGC TCCTGGGCAA CGTGCTGGTT ATTGTGCTGT CTCATCATTT
1921  TGGCAAAGAA TTCGAGCGGC CGCCAGCCGC CACCATGGTC TGCTTCAGAC TGTTCCCTGT
1981  CCCTGGATCT GGTCTGGTGC TTGTGTGCTT GGTGCTGGGT GCTGTGAGAT CCTATGCCCT
2041  TGAGCTGAAC CTGACTGACT CAGAAAATGC CACTTGCCTG TATGCCAAGT GGCAGATGAA
2101  CTTCACTGTG AGATATGAGA CTACCAACAA GACCTACAAG ACTGTGACCA TCTCAGACCA
2161  TGGCACTGTC ACCTACAATG GATCAATCTG TGGTGATGAT CAGAATGGCC CAAAGATAGC
2221  AGTGCAGTTT GGGCCCGGTT TTTCCTGGAT TGCTAACTTC ACCAAGGCAG CCTCCACCTA
2281  CAGCATTGAC TCAGTCAGCT TCAGCTACAA CACTGGGGAT AACACCACCT TCCCTGACGC
2341  AGAGGACAAG GGAATCCTTA CTGTGGACGA ACTCCTGGCA ATCAGAATCC CCCTTAACGA
```

-continued

```
2401  CCTGTTCAGA TGCAACTCCC TTTCAACCCT TGAAAAGAAT GATGTGGTGC AACACTATTG
2461  GGACGTCCTG GTGCAAGCCT TTGTGCAGAA TGGGACAGTG AGTACCAACG AGTTCCTCTG
2521  TGACAAGGAC AAGACCAGCA CTGTGGCCCC CACTATCCAC ACCACTGTGC CCAGCCCTAC
2581  CACTACCCCC ACCCCTAAAG AGAAGCCAGA AGCTGGAACC TACTCAGTCA ACAATGGAAA
2641  TGACACATGC CTCCTTGCCA CCATGGGACT GCAGCTGAAC ATCACTCAGG ACAAGGTGGC
2701  CTCAGTGATT AACATCAACC CTAACACCAC TCATAGCACT GGGAGCTGCA GATCACATAC
2761  AGCTCTGCTG AGGCTCAACT CCTCCACCAT CAAGTACCTG GACTTTGTGT TTGCTGTGAA
2821  GAATGAGAAC AGGTTCTACC TCAAGGAAGT GAACATTTCC ATGTACCTGG TCAATGGTTC
2881  AGTGTTCTCT ATTGCCAACA ACAATCTGAG CTACTGGGAT GCACCCCTGG GATCCTCCTA
2941  CATGTGCAAC AAGGAGCAGA CTGTGAGTGT GTCAGGTGCT TTTCAGATCA ACACTTTTGA
3001  CCTGAGGGTG CAGCCCTTCA ATGTGACTCA GGGAAAGTAC TCCACTGCAC AAGAGTGTTC
3061  CTTGGATGAT GACACTATCC TCATCCCCAT TATTGTGGGA GCTGGACTGT CAGGATTGAT
3121  TATAGTGATT GTGATTGCTT ATGTGATTGG AAGGAGAAAG AGCTATGCTG CTACCAGAC
3181  CCTGTAAAAG GGCGAATTCC AGCACACGCG TCCTAGGAGC TCGAGTACTA CTGGCGGCCG
3241  TTACTAGTGG ATCCGCGGTA CAAGTAAGCA TGCAAGCTTC GAGGACGGGG TGAACTACGC
3301  CTGAATCAAG CTTATCGATA AATTCGAGCA TCTTACCGCC ATTTATTCCC ATATTTGTTC
3361  TGTTTTTCTT GATTTGGGTA TACATTTAAA TGTTAATAAA ACAAAATGGT GGGGCAATCA
3421  TTTACATTTT TAGGGATATG TAATTACTAG TTCAGGTGTA TTGCCACAAG ACAAACATGT
3481  TAAGAAACTT TCCCGTTATT TACGCTCTGT TCCTGTTAAT CAACCTCTGG ATTACAAAAT
3541  TTGTGAAAGA TTGACTGATA TTCTTAACTA TGTTGCTCCT TTTACGCTGT GTGGATATGC
3601  TGCTTTAATG CCTCTGTATC ATGCTATTGC TTCCCGTACG GCTTTCGTTT TCTCCTCCTT
3661  GTATAAATCC TGGTTGCTGT CTCTTTATGA GGAGTTGTGG CCCGTTGTCC GTCAACGTGG
3721  CGTGGTGTGC TCTGTGTTTG CTGACGCAAC CCCCACTGGC TGGGGCATTG CCACCACCTG
3781  TCAACTCCTT TCTGGGACTT TCGCTTTCCC CCTCCCGATC GCCACGGCAG AACTCATCGC
3841  CGCCTGCCTT GCCCGCTGCT GGACAGGGGC TAGGTTGCTG GCACTGATA ATTCCGTGGT
3901  GTTGTCGGGG AAGGGCCTCG ATACCGTCGA TATCGATCCT GGCTAATAAA GGAAATTTAT
3961  TTTCATTGCA ATAGTGTGTT GGAATTTTTT GTGTCTCTCA CTCGGAAGGA CATATGGGAG
4021  GGCAAATCAT TTAAAACATC AGAATGAGTA TTTGGTTTAG AGTTTGGCAA CATATGCCCA
4081  TATGCTGGCT GCCATGAACA AAGGTTGGCT ATAAAGAGGT CATCAGTATA TGAAACAGCC
4141  CCCTGCTGTC CATTCCTTAT TCCATAGAAA AGCCTTGACT TGAGGTTAGA TTTTTTTTAT
4201  ATTTTGTTTT GTGTTATTTT TTTCTTTAAC ATCCCTAAAA TTTTCCTTAC ATGTTTTACT
4261  AGCCAGATTT TTCCTCCTCT CCTGACTACT CCCAGTCATA GCTGTCCCTC TTCTCTTATG
4321  GAGATCGAAG CAATTCGTTG ATCTGAATTT CGACCACCCA TAATAGATCT CCCATTACCC
4381  TGGTAGATAA GTAGCATGGC GGGTTAATCA TTAACTACAA GGAACCCCTA GTGATGGAGT
4441  TGGCCACTCC CTCTCTGCGC GCTCGCTCGC TCACTGAGGC CGGGCGACCA AAGGTCGCCC
4501  GACGCCCGGG CTTTGCCCGG GCGGCCTCAG TGAGCGAGCG AGCGCGCAG;
```
(SEQ ID NO: 9)
```
  1  CTGCGCGCTC GCTCGCTCAC TGAGGCCGCC CGGGCAAAGC CCGGGCGTCG GGCGACCTTT
 61  GGTCGCCCGG CCTCAGTGAG CGAGCGAGCG CGCAGAGAGG GAGTGGCCAA CTCCATCACT
121  AGGGGTTCCT TGTAGTTAAT GATTAACCCG CCATGCTACT TATCTACCAG GGTAATGGGG
181  ATCCTCTAGA ACTATAGCTA GTCGACATTG ATTATTGACT AGTTATTAAT AGTAATCAAT
```

```
241   TACGGGGTCA TTAGTTCATA GCCCATATAT GGAGTTCCGC GTTACATAAC TTACGGTAAA

301   TGGCCCGCCT GGCTGACCGC CCAACGACCC CCGCCCATTG ACGTCAATAA TGACGTATGT

361   TCCCATAGTA ACGCCAATAG GGACTTTCCA TTGACGTCAA TGGGTGGAGT ATTTACGGTA

421   AACTGCCCAC TTGGCAGTAC ATCAAGTGTA TCATATGCCA AGTACGCCCC CTATTGACGT

481   CAATGACGGT AAATGGCCCG CCTGGCATTA TGCCCAGTAC ATGACCTTAT GGGACTTTCC

541   TACTTGGCAG TACATCTACG TATTAGTCAT CGCTATTACC ATGGTCGAGG TGAGCCCCAC

601   GTTCTGCTTC ACTCTCCCCA TCTCCCCCCC CTCCCCACCC CCAATTTTGT ATTTATTTAT

661   TTTTTAATTA TTTTGTGCAG CGATGGGGGC GGGGGGGGGG GGGGGCGCG CGCCAGGCGG

721   GGCGGGGCGG GGCGAGGGGC GGGGCGGGGC GAGGCGGAGA GGTGCGGCGG CAGCCAATCA

781   GAGCGGCGCG CTCCGAAAGT TTCCTTTTAT GGCGAGGCGG CGGCGGCGGC GGCCCTATAA

841   AAAGCGAAGC GCGCGGCGGG CGGGAGTCGC TGCGCGCTGC CTTCGCCCCG TGCCCCGCTC

901   CGCCGCCGCC TCGCGCCGCC CGCCCCGGCT CTGACTGACC GCGTTACTCC CACAGGTGAG

961   CGGGCGGGAC GGCCCTTCTC CTCCGGGCTG TAATTAGCGC TTGGTTTAAT GACGGCTTGT

1021  TTCTTTTCTG TGGCTGCGTG AAAGCCTTGA GGGGCTCCGG GAGGGCCCTT TGTGCGGGGG

1081  GAGCGGCTCG GGGGGTGCGT GCGTGTGTGT GTGCGTGGGG AGCGCCGCGT GCGGCTCCGC

1141  GCTGCCCGGC GGCTGTGAGC GCTGCGGGCG CGGCGCGGGG CTTTGTGCGC TCCGCAGTGT

1201  GCGCGAGGGG AGCGCGGCCG GGGGCGGTGC CCCGCGGTGC GGGGGGGGCT GCGAGGGGAA

1261  CAAAGGCTGC GTGCGGGGTG TGTGCGTGGG GGGGTGAGCA GGGGGTGTGG GCGCGTCGGT

1321  CGGGCTGCAA CCCCCCCTGC ACCCCCCTCC CCGAGTTGCT GAGCACGGCC CGGCTTCGGG

1381  TGCGGGGCTC CGTACGGGGC GTGGCGCGGG GCTCGCCGTG CCGGGCGGGG GGTGGCGGCA

1441  GGTGGGGGTG CCGGGCGGGG CGGGGCCGCC TCGGGCCGGG GAGGGCTCGG GGGAGGGGCG

1501  CGGCGGCCCC CGGAGCGCCG GCGGCTGTCG AGGCGCGGCG AGCCGCAGCC ATTGCCTTTT

1561  ATGGTAATCG TGCGAGAGGG CGCAGGGACT TCCTTTGTCC CAAATCTGTG CGGAGCCGAA

1621  ATCTGGGAGG CGCCGCCGCA CCCCCTCTAG CGGGCGCGGG GCGAAGCGGT GCGGCGCCGG

1681  CAGGAAGGAA ATGGGCGGGA AGGGCCTTCG TGCGTCGCCG CGCCGCCGTC CCCTTCTCCC

1741  TCTCCAGCCT CGGGGCTGTC CGCGGGGGGA CGGCTGCCTT CGGGGGGGAC GGGGCAGGGC

1801  GGGGTTCGGC TTCTGGCGTG TGACCGGCGG CTCTAGAGCC TCTGCTAACC ATGTTCATGC

1861  CTTCTTCTTT TTCCTACAGC TCCTGGGCAA CGTGCTGGTT ATTGTGCTGT CTCATCATTT

1921  TGGCAAAGAA TTCGAGCGGC CGCCAGCCGC CACCATGGTG TGCTTTAGAC TGTTTCCTGT

1981  GCCTGGTTCA GGGCTGGTCC TGGTCTGTCT GGTGCTGGGG CTGTCAGAA GCTATGCCTT

2041  GGAGCTGAAC CTCACTGATA GTGAAAATGC CACTTGTCTG TATGCTAAGT GGCAGATGAA

2101  CTTCACTGTG AGATATGAAA CCACCAACAA GACTTACAAA ACAGTGACCA TCTCAGATCA

2161  TGGAACTGTG ACCTACAACG GCAGCATTTG TGGAGACGAC CAGAACGGAC CAAAAATCGC

2221  TGTCCAATTT GGGCCTGGAT TCTCCTGGAT TGCCAATTTC ACTAAAGCTG CCTCCACATA

2281  TTCAATTGAC TCAGTGTCCT TCTCCTACAA CACTGGGGAC AACACTACTT TCCCTGATGC

2341  TGAAGATAAG GGAATCTTGA CAGTGGATGA GCTGCTGGCT ATCAGGATCC CTTTGAATGA

2401  CCTGTTTAGG TGTAATTCAC TGAGCACTCT GGAGAAGAAC GACGTGGTGC AGCACTACTG

2461  GGACGTGCTG GTGCAGGCCT TTGTGCAGAA CGGCACTGTG TCCACCAACG AATTCCTGTG

2521  TGATAAGGAC AAAACTTCCA CTGTGGCACC TACAATTCAC ACTACTGTGC CTTCACCTAC

2581  CACCACTCCA ACTCCAAAGG AAAAGCCTGA AGCAGGAACC TACTCTGTGA ACAATGGCAA

2641  TGATACCTGT CTGTTGGCCA CCATGGGCCT CCAACTGAAC ATTACTCAGG ACAAGGTGGC
```

-continued

```
2701  CTCAGTGATT AACATTAACC CCAACACTAC CCACTCCACT GGCAGCTGTA GATCACACAC

2761  AGCCTTGCTC AGACTGAATA GCAGCACCAT CAAGTATTTG GATTTGTGT TTGCAGTGAA

2821  GAATGAAAAC AGGTTCTACC TGAAGGAAGT CAACATCTCA ATGTACCTGG TGAACGGCTC

2881  AGTGTTCAGC ATTGCCAACA CAACCTCTC CTATTGGGAC GCTCCACTGG GGAGCAGCTA

2941  CATGTGTAAC AAGGAACAGA CTGTGTCAGT GTCAGGAGCC TTCCAGATTA ACACCTTTGA

3001  TCTGAGGGTC CAACCCTTTA ATGTCACTCA AGGAAAGTAT AGCACTGCCC AGGAGTGCTC

3061  CCTGGATGAT GACACCATTC TGATTCCAAT CATTGTGGGT GCAGGACTTT CTGGGCTTAT

3121  TATTGTGATT GTGATTGCCT ATGTGATTGG CAGAAGGAAA TCCTATGCAG GGTACCAAAC

3181  TCTGTAAAAG GGCGAATTCC AGCACACGCG TCCTAGGAGC TCGAGTACTA CTGGCGGCCG

3241  TTACTAGTGG ATCCGCGGTA CAAGTAAGCA TGCAAGCTTC GAGGACGGGG TGAACTACGC

3301  CTGAATCAAG CTTATCGATA AATTCGAGCA TCTTACCGCC ATTTATTCCC ATATTTGTTC

3361  TGTTTTTCTT GATTTGGGTA TACATTTAAA TGTTAATAAA CAAAATGGT GGGGCAATCA

3421  TTTACATTTT TAGGGATATG TAATTACTAG TTCAGGTGTA TTGCCACAAG ACAAACATGT

3481  TAAGAAACTT TCCCGTTATT TACGCTCTGT TCCTGTTAAT CAACCTCTGG ATTACAAAAT

3541  TTGTGAAAGA TTGACTGATA TTCTTAACTA TGTTGCTCCT TTTACGCTGT GTGGATATGC

3601  TGCTTTAATG CCTCTGTATC ATGCTATTGC TTCCCGTACG GCTTTCGTTT TCTCCTCCTT

3661  GTATAAATCC TGGTTGCTGT CTCTTTATGA GGAGTTGTGG CCCGTTGTCC GTCAACGTGG

3721  CGTGGTGTGC TCTGTGTTTG CTGACGCAAC CCCCACTGGC TGGGGCATTG CCACCACCTG

3781  TCAACTCCTT TCTGGGACTT TCGCTTTCCC CCTCCCGATC GCCACGGCAG AACTCATCGC

3841  CGCCTGCCTT GCCCGCTGCT GGACAGGGGC TAGGTTGCTG GGCACTGATA ATTCCGTGGT

3901  GTTGTCGGGG AAGGGCCTCG ATACCGTCGA TATCGATCCT GGCTAATAAA GGAAATTTAT

3961  TTTCATTGCA ATAGTGTGTT GGAATTTTTT GTGTCTCTCA CTCGGAAGGA CATATGGGAG

4021  GGCAAATCAT TTAAAACATC AGAATGAGTA TTTGGTTTAG AGTTTGGCAA CATATGCCCA

4081  TATGCTGGCT GCCATGAACA AAGGTTGGCT ATAAAGAGGT CATCAGTATA TGAAACAGCC

4141  CCCTGCTGTC CATTCCTTAT TCCATAGAAA AGCCTTGACT TGAGGTTAGA TTTTTTTTAT

4201  ATTTTGTTTT GTGTTATTTT TTTCTTTAAC ATCCCTAAAA TTTTCCTTAC ATGTTTTACT

4261  AGCCAGATTT TTCCTCCTCT CCTGACTACT CCCAGTCATA GCTGTCCCTC TTCTCTTATG

4321  GAGATCGAAG CAATTCGTTG ATCTGAATTT CGACCACCCA TAATAGATCT CCCATTACCC

4381  TGGTAGATAA GTAGCATGGC GGGTTAATCA TTAACTACAA GGAACCCCTA GTGATGGAGT

4441  TGGCCACTCC CTCTCTGCGC GCTCGCTCGC TCACTGAGGC CGGGCGACCA AAGGTCGCCC

4501  GACGCCCGGG CTTTGCCCGG GCGGCCTCAG TGAGCGAGCG AGCGCGCAG;
and (SEQ ID NO: 10)
   1  CTGCGCGCTC GCTCGCTCAC TGAGGCCGCC CGGGCAAAGC CCGGGCGTCG GGCGACCTTT

61  GGTCGCCCGG CCTCAGTGAG CGAGCGAGCG CGCAGAGAGG GAGTGGCCAA CTCCATCACT

121  AGGGGTTCCT TGTAGTTAAT GATTAACCCG CCATGCTACT TATCTACCAG GGTAATGGGG

181  ATCCTCTAGA ACTATAGCTA GTCGACATTG ATTATTGACT AGTTATTAAT AGTAATCAAT

241  TACGGGGTCA TTAGTTCATA GCCCATATAT GGAGTTCCGC GTTACATAAC TTACGGTAAA

301  TGGCCCGCCT GGCTGACCGC CCAACGACCC CCGCCCATTG ACGTCAATAA TGACGTATGT

361  TCCCATAGTA ACGCCAATAG GGACTTTCCA TTGACGTCAA TGGGTGGAGT ATTTACGGTA

421  AACTGCCCAC TTGGCAGTAC ATCAAGTGTA TCATATGCCA AGTACGCCCC CTATTGACGT
```

-continued

```
 481  CAATGACGGT AAATGGCCCG CCTGGCATTA TGCCCAGTAC ATGACCTTAT GGGACTTTCC
 541  TACTTGGCAG TACATCTACG TATTAGTCAT CGCTATTACC ATGGTCGAGG TGAGCCCCAC
 601  GTTCTGCTTC ACTCTCCCCA TCTCCCCCCC CTCCCCACCC CCAATTTTGT ATTTATTTAT
 661  TTTTTAATTA TTTTGTGCAG CGATGGGGGC GGGGGGGGGG GGGGGCGCG  CGCCAGGCGG
 721  GGCGGGGCGG GGCGAGGGGC GGGGCGGGGC GAGGCGGAGA GGTGCGGCGG CAGCCAATCA
 781  GAGCGGCGCG CTCCGAAAGT TTCCTTTTAT GGCGAGGCGG CGGCGGCGGC GGCCCTATAA
 841  AAAGCGAAGC GCGCGGCGGG CGGGAGTCGC TGCGCGCTGC CTTCGCCCCG TGCCCCGCTC
 901  CGCCGCCGCC TCGCGCCGCC CGCCCCGGCT CTGACTGACC GCGTTACTCC CACAGGTGAG
 961  CGGGCGGGAC GGCCCTTCTC CTCCGGGCTG TAATTAGCGC TTGGTTTAAT GACGGCTTGT
1021  TTCTTTTCTG TGGCTGCGTG AAAGCCTTGA GGGGCTCCGG GAGGGCCCTT TGTGCGGGGG
1081  GAGCGGCTCG GGGGGTGCGT GCGTGTGTGT GTGCGTGGGG AGCGCCGCGT GCGGCTCCGC
1141  GCTGCCCGGC GGCTGTGAGC GCTGCGGGCG CGGCGCGGGG CTTTGTGCGC TCCGCAGTGT
1201  GCGCGAGGGG AGCGCGGCCG GGGGCGGTGC CCCGCGGTGC GGGGGGGGCT GCGAGGGGAA
1261  CAAAGGCTGC GTGCGGGGTG TGTGCGTGGG GGGGTGAGCA GGGGGTGTGG GCGCGTCGGT
1321  CGGGCTGCAA CCCCCCCTGC ACCCCCCTCC CCGAGTTGCT GAGCACGGCC CGGCTTCGGG
1381  TGCGGGGCTC CGTACGGGGC GTGGCGCGGG GCTCGCCGTG CCGGGCGGGG GGTGGCGGCA
1441  GGTGGGGGTG CCGGGCGGGG CGGGGCCGCC TCGGGCCGGG GAGGGCTCGG GGGAGGGGCG
1501  CGGCGGCCCC CGGAGCGCCG GCGGCTGTCG AGGCGCGGCG AGCCGCAGCC ATTGCCTTTT
1561  ATGGTAATCG TGCGAGAGGG CGCAGGGACT TCCTTTGTCC CAAATCTGTG CGGAGCCGAA
1621  ATCTGGGAGG CGCCGCCGCA CCCCCTCTAG CGGGCGCGGG GCGAAGCGGT GCGGCGCCGG
1681  CAGGAAGGAA ATGGGCGGGG AGGGCCTTCG TGCGTCGCCG CGCCGCCGTC CCCTTCTCCC
1741  TCTCCAGCCT CGGGGCTGTC CGCGGGGGGA CGGCTGCCTT CGGGGGGGAC GGGGCAGGGC
1801  GGGGTTCGGC TTCTGGCGTG TGACCGGCGG CTCTAGAGCC TCTGCTAACC ATGTTCATGC
1861  CTTCTTCTTT TTCCTACAGC TCCTGGGCAA CGTGCTGGTT ATTGTGCTGT CTCATCATTT
1921  TGGCAAAGAA TTCGAGCGGC CGCCAGCCGC CACCATGGTC TGTTTTAGGC TGTTCCCTGT
1981  CCCTGGTTCA GGACTGGTCT TAGTGTGTCT GGTGCTTGGA GCTGTCAGAA GCTATGCCCT
2041  GGAGCTGAAC CTGACTGACT CAGAAAATGC CACTTGCCTG TATGCCAAGT GGCAGATGAA
2101  CTTCACTGTC AGATATGAAA CCACCAACAA GACCTATAAG ACTGTGACCA TCTCAGACCA
2161  TGGCACTGTG ACTTACAATG GGTCAATTTG TGGAGATGAC CAGAATGGCC CTAAGATAGC
2221  TGTCCAGTTT GGTCCAGGAT TCAGCTGGAT TGCCAACTTC ACCAAGGCAG CCAGCACCTA
2281  CAGCATTGAC TCTGTGTCCT TCTCCTACAA CACAGGAGAC AACACCACTT TCCCTGATGC
2341  AGAGGACAAA GGTATCCTGA CTGTGGATGA GTTGCTGGCA ATCAGGATCC CACTGAACGA
2401  TCTGTTCAGG TGCAACTCAC TGTCCACTCT GGAAAAGAAT GATGTGGTGC AGCACTATTG
2461  GGATGTGCTA GTCCAGGCCT TTGTCCAGAA TGGGACTGTG TCAACTAATG AGTTCCTGTG
2521  TGACAAGGAC AAGACAAGCA CTGTAGCCCC CACTATCCAT ACCACAGTAC CTAGCCCCAC
2581  CACTACTCCA ACCCCCAAGG AGAAGCCTGA GGCTGGCACC TACTCAGTGA ACAATGGGAA
2641  TGACACCTGT TTGCTGGCCA CTATGGGACT CCAACTGAAC ATCACCCAGG ACAAAGTGGC
2701  CTCTGTGATC AATATCAATC CCAACACCAC CCACAGCACT GGGTCCTGCA GAAGCCACAC
2761  TGCCCTCCTG AGGCTCAACT CATCAACTAT CAAGTACTTG GATTTTGTGT TTGCAGTGAA
2821  GAATGAGAAC AGATTCTACC TCAAAGAGGT CAACATTTCA ATGTACCTGG TGAATGGGAG
2881  TGTGTTCTCC ATTGCTAACA ACAACCTGAG CTACTGGGAT GCCCCTCTGG GCTCCTCATA
```

```
2941  CATGTGCAAC AAGGAACAGA CTGTGAGTGT GTCAGGGGCC TTCCAGATCA ACACTTTTGA
3001  CCTGAGAGTG CAGCCCTTTA ATGTGACACA GGGAAAGTAC AGCACTGCTC AGGAGTGCAG
3061  CCTGGATGAT GACACTATCC TGATCCCTAT CATTGTGGGG GCAGGCCTGT CTGGACTCAT
3121  TATTGTGATT GTGATTGCCT ATGTGATAGG GAGAAGGAAG TCTTATGCTG GATACCAGAC
3181  CCTGTAAAAG GGCGAATTCC AGCACACGCG TCCTAGGAGC TCGAGTACTA CTGGCGGCCG
3241  TTACTAGTGG ATCCGCGGTA CAAGTAAGCA TGCAAGCTTC GAGGACGGGG TGAACTACGC
3301  CTGAATCAAG CTTATCGATA AATTCGAGCA TCTTACCGCC ATTTATTCCC ATATTTGTTC
3361  TGTTTTTCTT GATTTGGGTA TACATTTAAA TGTTAATAAA ACAAAATGGT GGGGCAATCA
3421  TTTACATTTT TAGGGATATG TAATTACTAG TTCAGGTGTA TTGCCACAAG ACAAACATGT
3481  TAAGAAACTT TCCCGTTATT TACGCTCTGT TCCTGTTAAT CAACCTCTGG ATTACAAAAT
3541  TTGTGAAAGA TTGACTGATA TTCTTAACTA TGTTGCTCCT TTTACGCTGT GTGGATATGC
3601  TGCTTTAATG CCTCTGTATC ATGCTATTGC TTCCCGTACG GCTTTCGTTT TCTCCTCCTT
3661  GTATAAATCC TGGTTGCTGT CTCTTTATGA GGAGTTGTGG CCCGTTGTCC GTCAACGTGG
3721  CGTGGTGTGC TCTGTGTTTG CTGACGCAAC CCCCACTGGC TGGGGCATTG CCACCACCTG
3781  TCAACTCCTT TCTGGGACTT TCGCTTTCCC CCTCCCGATC GCCACGGCAG AACTCATCGC
3841  CGCCTGCCTT GCCCGCTGCT GGACAGGGGC TAGGTTGCTG GGCACTGATA ATTCCGTGGT
3901  GTTGTCGGGG AAGGGCCTCG ATACCGTCGA TATCGATCCT GGCTAATAAA GGAAATTTAT
3961  TTTCATTGCA ATAGTGTGTT GGAATTTTTT GTGTCTCTCA CTCGGAAGGA CATATGGGAG
4021  GGCAAATCAT TTAAAACATC AGAATGAGTA TTTGGTTTAG AGTTTGGCAA CATATGCCCA
4081  TATGCTGGCT GCCATGAACA AAGGTTGGCT ATAAAGAGGT CATCAGTATA TGAAACAGCC
4141  CCCTGCTGTC CATTCCTTAT TCCATAGAAA AGCCTTGACT TGAGGTTAGA TTTTTTTTAT
4201  ATTTTGTTTT GTGTTATTTT TTTCTTTAAC ATCCCTAAAA TTTTCCTTAC ATGTTTTACT
4261  AGCCAGATTT TTCCTCCTCT CCTGACTACT CCCAGTCATA GCTGTCCCTC TTCTCTTATG
4321  GAGATCGAAG CAATTCGTTG ATCTGAATTT CGACCACCCA TAATAGATCT CCCATTACCC
4381  TGGTAGATAA GTAGCATGGC GGGTTAATCA TTAACTACAA GGAACCCCTA GTGATGGAGT
4441  TGGCCACTCC CTCTCTGCGC GCTCGCTCGC TCACTGAGGC CGGGCGACCA AAGGTCGCCC
4501  GACGCCCGGG CTTTGCCCGG GCGGCCTCAG TGAGCGAGCG AGCGCGCAG.
```

Figure 1B:
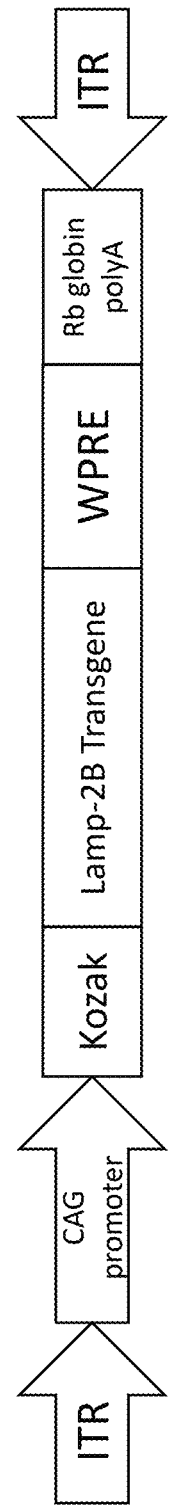
FIG. 1B provides a diagram of an illustrative embodiment of an expression cassette of an adeno-associated virus (AAV) gene therapy vector.

In certain embodiments, the expression cassette comprises one or more modifications as compared to a sequence selected from SEQ ID NOs: 8-10, including but not limited to any of the modifications disclosed herein. In particular embodiments, the one or more modifications comprise one or more of: removal of one or more (e.g., all) upstream ATG sequences, replacement of the Kozak sequence with an optimized consensus Kozak sequence or another Kozak sequence, including but not limited to any of those disclosed herein, and/or replacement of the polyadenylation sequence with a full-length polyadenylation sequence or another polyadenylation sequence, including but not limited to any of those disclosed herein. An illustrative configuration of genetic elements within these exemplary expression cassettes is depicted in FIG. 1B.

In an embodiment, the vector is an adeno-associated virus (AAV) vector. In an embodiment, the expression cassette comprises inverted terminal repeat (ITR) sequences selected from SEQ ID NOs: 11 and 12:

(SEQ ID NO: 11)
```
  1   CTGCGCGCTC GCTCGCTCAC TGAGGCCGCC CGGGCAAAGC CCGGGCGTCG GGCGACCTTT

61   GGTCGCCCGG CCTCAGTGAG CGAGCGAGCG CGCAGAGAGG GAGTGGCCAA CTCCATCACT

121   AGGGGTTCCT;
```

(SEQ ID NO: 12)
```
  1    AGGAACCCCT AGTGATGGAG TTGGCCACTC CCTCTCTGCG CGCTCGCTCG CTCACTGAGG

61    CCGGGCGACC AAAGGTCGCC CGACGCCCGG GCTTTGCCCG GGCGGCCTCA GTGAGCGAGC

121    GAGCGCGCAG.
```

In related embodiments, the disclosure provides gene therapy vectors comprising an expression cassette disclosed herein. Generally, the gene therapy vectors described herein comprise an expression cassette comprising a polynucleotide encoding one or more isoforms of lysosome-associated membrane protein 2 (LAMP-2), and allows for the expression of LAMP-2 to partially or wholly rectify deficient LAMP-2 protein expression levels and/or autophagic flux in a subject in need thereof (e.g., a subject having Danon disease or another disorder characterized by deficient autophagic flux at least in part due to deficient LAMP-2 expression). In particular embodiments, the expression cassette comprises a polynucleotide sequence encoding LAMP-2 disclosed herein, e.g., SEQ ID NOs: 3-5, or a functional variant thereof. In some embodiments, the variant sequence has at least 90%, at least 95%, at least 98%, or at least 99% identity to any of SEQ ID NOs: 3-5. In some embodiments, the variant is a fragment of any of SEQ ID NOs: 3-5, e.g., a fragment having at least 50%, at least 60%, at least 70%, at least 80%, at least 90%, or at least 95% of the sequence of any of SEQ ID Nos: 3-5. The gene therapy vectors can be viral or non-viral vectors. Illustrative non-viral vectors include, e.g., naked DNA, cationic liposome complexes, cationic polymer complexes, cationic liposome-polymer complexes, and exosomes. Examples of viral vectors include, but are not limited to, adenoviral, retroviral, lentiviral, herpesvirus and adeno-associated virus (AAV) vectors.

In certain embodiments, the viral vector is an AAV vector. AAV is a 4.7 kb, single stranded DNA virus. Recombinant vectors based on AAV are associated with excellent clinical safety, since wild-type AAV is nonpathogenic and has no etiologic association with any known diseases. In addition, AAV offers the capability for highly efficient gene delivery and sustained transgene expression in numerous tissues. By an "AAV vector" is meant a vector derived from an adeno-associated virus serotype, including without limitation, AAV1, AAV2, AAV3, AAV4, AAV5, AAV6, AAV7, AAV8, AAV9, AAV10, AAVrh.10, AAVrh.74, etc. AAV vectors can have one or more of the AAV wild-type genes deleted in whole or part, e.g., the rep and/or cap genes, but retain functional flanking inverted terminal repeat (ITR) sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g. by the insertion, deletion or substitution of nucleotides, as long as the sequences provide for functional rescue, replication and packaging. AAV vectors may comprise other modifications, including but not limited to one or more modified capsid protein (e.g., VP1, VP2 and/or VP3). For example, a capsid protein may be modified to alter tropism and/or reduce immunogenicity.

Recombinant vectors based on AAV are associated with excellent clinical safety, since wild-type AAV is nonpathogenic and has no etiologic association with any known diseases. In addition, AAV offers the capability for highly efficient gene delivery and sustained transgene expression in numerous tissues. Various serotypes of AAV are known, including, AAV1, AAV2, AAV3, AAV4, AAV5, AAV6, AAV7, AAV8, AAV9, AAV10, AAVrh.10, AAVrh.74, etc. AAV vectors can have one or more of the AAV wild-type genes deleted in whole or part, e.g., the rep and/or cap genes, but retain functional flanking inverted terminal repeat (ITR) sequences. The serotype of a recombinant AAV vector is determined by its capsid. International Patent Publication No. WO2003042397A2 discloses various capsid sequences including those of AAV1, AAV2, AAV3, AAV8, AAV9, and rh10. International Patent Publication No. WO2013078316A1 discloses the polypeptide sequence of the VP1 from AAVrh74. Numerous diverse naturally occurring or genetically modified AAV capsid sequences are known in the art.

An exemplary, non-limiting capsid is an AAV9 capsid, having the sequence of SEQ ID NO: 28 (or the VP1, VP2, or VP3 fragments thereof). In some embodiments, the AAV vectors of the disclosure comprise capsid proteins that share at least 93%, at least 94%, at least 95%, at least 96%, at least 97%, at least 98%, at least 99%, or at least 100% identity of the entire sequence of SEQ ID NO: 28, or over amino acids 138 to 736 of SEQ ID NO: 28, or over amino acids 203 to 736 of SEQ ID NO: 28.

(SEQ ID NO: 28)
```
  1    MAADGYLPDW  LEDNLSEGIR  EWWALKPGAP  QPKANQQHQD  NARGLVLPGY  KYLGPGNGLD

61    KGEPVNAADA  AALEHDKAYD  QQLKAGDNPY  LKYNHADAEF  QERLKEDTSF  GGNLGRAVFQ

121    AKKRLLEPLG  LVEEAAKTAP  GKKRPVEQSP  QEPDSSAGIG  KSGAQPAKKR  LNFGQTGDTE

181    SVPDPQPIGE  PPAAPSGVGS  LTMASGGGAP  VADNNEGADG  VGSSSGNWHC  DSQWLGDRVI

241    TTSTRTWALP  TYNNHLYKQI  SNSTSGGSSN  DNAYFGYSTP  WGYFDFNRFH  CHFSPRDWQR

301    LINNNWGFRP  KRLNFKLFNI  QVKEVTDNNG  VKTIANNLTS  TVQVFTDSDY  QLPYVLGSAH

361    EGCLPPFPAD  VFMIPQYGYL  TLNDGSQAVG  RSSFYCLEYF  PSQMLRTGNN  FQFSYEFENV

421    PFHSSYAHSQ  SLDRLMNPLI  DQYLYYLSKT  INGSGQNQQT  LKFSVAGPSN  MAVQGRNYIP
```

```
-continued
481  GPSYRQQRVS TTVTQNNNSE FAWPGASSWA LNGRNSLMNP GPAMASHKEG EDRFFPLSGS

541  LIFGKQGTGR DNVDADKVMI TNEEEIKTTN PVATESYGQV ATNHQSAQAQ AQTGWVQNQG

601  ILPGMVWQDR DVYLQGPIWA KIPHTDGNFH PSPLMGGFGM KHPPPQILIK NTPVPADPPT

661  AFNKDKLNSF ITQYSTGQVS VEIEWELQKE NSKRWNPEIQ YTSNYYKSNN VEFAVNTEGV

721  YSEPRPIGTR YLTRNL.
```

AAV expression vectors are constructed using known techniques to at least provide as operatively linked components in the direction of transcription, control elements including a transcriptional initiation region, the DNA of interest (i.e. the LAMP-2 gene) and a transcriptional termination region.

In some embodiments, the viral vector is an AAV9 vector. In some embodiments, the expression cassette of the viral vector is flanked by AAV2 inverted terminal repeats (ITRs). ITRs used in alternative embodiments of the disclosed vectors include, but are not limited to, AAV2, AAV3, AAV4, AAV5, AAV6, AAV7, AAV8, and AAV9. In some embodiments, the viral vector is an AAV2/9 vector. The notation AAV2/9 refers to an AAV vector have the ITRs of AAV2 and the capsid of AAV9. Other embodiments of the disclosure include without limitation AAV2/9, AAV5/9, AAVrh74, AAV2/rh74, AAV5/9, and AAV5/rh74 vectors. Other ITRs known in the art may be used. Exemplary ITRs (and other AAV components) useful in the vectors of the present disclosure include, without limitation, those described in U.S. Pat. No. 6,936,466B2, U.S. Pat. No. 9,169,494B2, US20050220766A1, US20190022249A1, and U.S. Pat. No. 7,282,199B2, which are each incorporated by reference herein in their entireties.

In some embodiments, the vector is a retroviral vector, or more specifically, a lentiviral vector. As used herein, the term "retrovirus" or "retroviral" refers an RNA virus that reverse transcribes its genomic RNA into a linear double-stranded DNA copy and subsequently covalently integrates its genomic DNA into a host genome. Retrovirus vectors are a common tool for gene delivery (Miller, 2000, Nature. 357: 455-460). Once the virus is integrated into the host genome, it is referred to as a "provirus." The provirus serves as a template for RNA polymerase II and directs the expression of RNA molecules encoded by the virus.

Illustrative retroviruses (family Retroviridae) include, but are not limited to: (1) genus gammaretrovirus, such as, Moloney murine leukemia virus (M-MuLV), Moloney murine sarcoma virus (MoMSV), murine mammary tumor virus (MuMTV), gibbon ape leukemia virus (GaLV), and feline leukemia virus (FLV), (2) genus spumavirus, such as, simian foamy virus, (3) genus lentivirus, such as, human immunodeficiency virus-1 and simian immunodeficiency virus.

As used herein, the term "lentiviral" or "lentivirus" refers to a group (or genus) of complex retroviruses. Illustrative lentiviruses include, but are not limited to: HIV (human immunodeficiency virus; including HIV type 1, and HIV type 2; visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV-based vector backbones (i.e., HIV cis-acting sequence elements) are preferred.

Retroviral vectors, and more particularly, lentiviral vectors, may be used in practicing the present invention. Accordingly, the term "retroviral vector," as used herein is meant to include "lentiviral vector"; and the term "retrovirus" as used herein is meant to include "lentivirus."

The term viral vector may refer either to a vector or viral particle capable of transferring a nucleic acid into a cell or to the transferred nucleic acid itself. Viral vectors contain structural and/or functional genetic elements that are primarily derived from a virus. The term "retroviral vector" refers to a viral vector containing structural and functional genetic elements, or portions thereof, that are primarily derived from a retrovirus. The term "lentiviral vector" refers to a viral vector containing structural and functional genetic elements, or portions thereof, including LTRs that are primarily derived from a lentivirus. The term "hybrid" refers to a vector, LTR or other nucleic acid containing both retroviral, e.g., lentiviral, sequences and non-lentiviral viral sequences. In one embodiment, a hybrid vector refers to a vector or transfer plasmid comprising retroviral, e.g., lentiviral, sequences for reverse transcription, replication, integration and/or packaging.

In particular embodiments, the terms "lentiviral vector" and "lentiviral expression vector" may be used to refer to lentiviral transfer plasmids and/or infectious lentiviral particles. Where reference is made herein to elements such as cloning sites, promoters, regulatory elements, heterologous nucleic acids, etc., it is to be understood that the sequences of these elements are present in RNA form in the lentiviral particles of the invention and are present in DNA form in the DNA plasmids of the invention.

According to certain specific embodiments, most or all of the viral vector backbone sequences are derived from a lentivirus, e.g., HIV-1. However, it is to be understood that many different sources of lentiviral sequences can be used, and numerous substitutions and alterations in certain of the lentiviral sequences may be accommodated without impairing the ability of a transfer vector to perform the functions described herein. Moreover, a variety of lentiviral vectors are known in the art, see Naldini et al., (1996a, 1996b, and 1998); Zufferey et al., (1997); Dull et al., 1998, U.S. Pat. Nos. 6,013,516; and 5,994,136, many of which may be adapted to produce a viral vector or transfer plasmid of the present invention.

The LAMP-2B transgene sequences disclosed herein are, in various embodiments, used in any vector system known in the art or prospectively discovered. The invention is not limited to any particular viral vector described herein, as it is within the skill of those in the art to use a transgene sequence in other vector systems without undue experimentation and with a reasonable expectation of success.

Gene delivery viral vectors useful in the practice of the present invention can be constructed utilizing methodologies well known in the art of molecular biology. Typically, viral vectors carrying transgenes are assembled from polynucleotides encoding the transgene, suitable regulatory elements and elements necessary for production of viral proteins, which mediate cell transduction. Such recombinant viruses may be produced by techniques known in the art, e.g., by transfecting packaging cells or by transient transfection with helper plasmids or viruses. Typical examples of virus packaging cells include but are not limited to HeLa cells, SF9 cells (optionally with a baculovirus helper vector), 293 cells, etc. A Herpesvirus-based system can be used to produce AAV vectors, as described in US20170218395A1. Detailed protocols for producing such replication-defective recombinant viruses may be found for instance in WO95/14785, WO96/22378, U.S. Pat. Nos. 5,882,877, 6,013,516, 4,861,719, 5,278,056 and WO94/19478, the complete contents of each of which is hereby incorporated by reference.

The present disclosure also provides pharmaceutical compositions comprising an expression cassette or vector (e.g., gene therapy vector) disclosed herein and one or more pharmaceutically acceptable carriers, diluents or excipients. In particular embodiments, the pharmaceutical composition comprises an AAV vector comprising an expression cassette disclosed herein, e.g., wherein the expression cassette comprises a codon-optimized transgene encoding LAMP-2B, e.g., any of SEQ ID NOs: 3-5 and variants thereof. Provided are pharmaceutical compositions, e.g., for use in preventing or treating a disorder characterized by deficient autophagic flux (e.g., Danon disease) which comprises a therapeutically effective amount of an expression cassette or vector disclosed herein that comprises a nucleic acid sequence of a polynucleotide that encodes one or more isoforms of LAMP-2.

AAV vectors useful in the practice of the present invention can be packaged into AAV virions (viral particles) using various systems including adenovirus-based and helper-free systems. Standard methods in AAV biology include those described in Kwon and Schaffer. *Pharm Res*. (2008) 25(3):489-99; Wu et al. *Mol. Ther*. (2006) 14(3):316-27. Burger et al. *Mol. Ther*. (2004) 10(2):302-17; Grimm et al. *Curr Gene Ther*. (2003) 3(4):281-304; Deyle D R, Russell D W. *Curr Opin Mol Ther*. (2009) 11(4):442-447; McCarty et al. *Gene Ther*. (2001) 8(16):1248-54; and Duan et al. *Mol Ther*. (2001) 4(4):383-91. Helper-free systems included those described in U.S. Pat. Nos. 6,004,797; 7,588,772; and 7,094,604;

The pharmaceutical compositions that contain the expression cassette or vector may be in any form that is suitable for the selected mode of administration, for example, for intraventricular, intramyocardial, intracoronary, intravenous, intra-arterial, intra-renal, intraurethral, epidural or intramuscular administration. The gene therapy vector comprising a polynucleotide encoding one or more LAMP-2 isoforms can be administered, as sole active agent, or in combination with other active agents, in a unit administration form, as a mixture with conventional pharmaceutical supports, to animals and human beings. In some embodiments, the pharmaceutical composition comprises cells transduced ex vivo with any of the gene therapy vectors of the disclosure.

In some embodiments, the viral vector (e.g. AAV vector), or a pharmaceutical composition comprising that vector, is effective when administered systemically. For example, the viral vectors of the disclosure, in some cases, demonstrate efficacy when administered intravenously to subject (e.g., a primate, such as a non-human primate or a human). In some embodiments, the viral vectors of the disclosure are capable of inducing expression of LAMP-2B in various tissues when administered systemically (e.g., in heart, muscle, and/or lung). In particular embodiments, administration of an AAV9 vector comprising a transgene substantially identical to, or identical to, SEQ ID NO: 3 to a subject intravenously results in detectable expression of LAMP-2B in heart tissue. In some embodiments, expression of LAMP-2B is detectable in one or more, or all, of the left ventricle, the right ventricle, the left atrium, and the right atrium of the heart of the subject. In some embodiments, expression of LAMP-2B is detectable in sub-region 1 and/or sub-region 2 of the left ventricle of the heart of the subject.

"Detectable expression" typically refers to transgene expression at least 5%, 10%, 15%, 20% or more compared to a control subject or tissue not treated with the viral vector. In some embodiments, detectable expression means expression at least 1.5-fold, at least 2-fold, at least 2.5-fold, at least 3-fold, at least 5-fold, at least 10-fold, at least 20-fold, at least 50-fold, or at least 100-fold greater than a no-vector control. Transgene expression can be determined as the increase over expression of the wild-type or endogenous gene in the cell (accounting for the potential that expression of the transgene may influence expression of the endogenous gene). Transgene expression can also be determined by RT-PCR detection of sequences that are present on the transgene mRNA transcript but not on the mRNA transcript of the endogenous gene. For example, the 3' UTR of the transcript may be used to determine the expression of the transgene independent of the expression of the endogenous gene (which may have a different 3' UTR). Expression of the polypeptide encoded by the transgene can be assessed by western blot or enzyme-linked immunosorbent assay (ELISA), as described in the examples that follow, or other methods known in the art. Antibodies cross-reactive to the wild-type and exogenous copies of the protein may be used. In some cases, an antibody specific to the exogenous protein can be identified and used to determine transgene expression. Those of skill in the art can design appropriate detection methodologies taking into account the target cell or tissue. In some cases, expression is measured quantitatively using a standard curve. Standard curves can be generated using purified LAMP-2 protein, by methods described in the examples or known in the art. Alternatively, expression of the transgene can be assessed by quantification of the corresponding mRNA.

In some embodiments, detectable expression of LAMP-2B in heart tissue occurs at doses, in vector genomes (vg) per kilogram weight of subject (kg), of $5\times10^{14}$ vg/kg or less, $3\times10^{14}$ vg/kg or less, $2\times10^{14}$ vg/kg or less, $1\times10^{14}$ vg/kg or less, $9\times10^{13}$ vg/kg or less, $8\times10^{13}$ vg/kg or less, $7\times10^{13}$ vg/kg or less, $6\times10^{13}$ vg/kg or less, $5\times10^{13}$ vg/kg or less, $4\times10^{13}$ vg/kg or less, $3\times10^{13}$ vg/kg or less, $2\times10^{13}$ vg/kg or less, or $1\times10^{13}$ vg/kg or less.

In some embodiments, detectable expression of LAMP-2B in heart tissue occurs at doses, in vector genomes (vg) per kilogram weight of subject (kg), of $1\times10^{13}$ vg/kg to $2\times10^{13}$ vg/kg, $2\times10^{13}$ vg/kg to $3\times10^{13}$ vg/kg, $3\times10^{13}$ vg/kg to $4\times10^{13}$ vg/kg, $4\times10^{13}$ vg/kg to $5\times10^{13}$ vg/kg, $5\times10^{13}$ vg/kg to $6\times10^{13}$ vg/kg, $6\times10^{13}$ vg/kg to $7\times10^{13}$ vg/kg, $7\times10^{13}$ vg/kg to $8\times10^{13}$ vg/kg, $8\times10^{13}$ vg/kg to $9\times10^{13}$ vg/kg, $9\times10^{13}$ vg/kg to $1\times10^{14}$ vg/kg, $1\times10^{14}$ vg/kg to $2\times10^{14}$ vg/kg, $2\times10^{14}$ vg/kg to $3\times10^{14}$ vg/kg, or $3\times10^{14}$ vg/kg to $5\times10^{14}$ vg/kg.

In some embodiments, detectable expression of LAMP-2B in heart tissue occurs at doses, in vector genomes (vg) per kilogram weight of subject (kg), of $1\times10^{13}$ vg/kg to $3\times10^{13}$ vg/kg, $3\times10^{13}$ vg/kg to $5\times10^{13}$ vg/kg, $5\times10^{13}$ vg/kg to $7\times10^{13}$ vg/kg, $7\times10^{13}$ vg/kg to $9\times10^{13}$ vg/kg, $9\times10^{13}$ vg/kg to $2\times10^{14}$ vg/kg, or $2\times10^{14}$ vg/kg to $5\times10^{14}$ vg/kg. In some embodiments, detectable expression of LAMP-2B in heart tissue occurs at doses, in vector genomes (vg) per kilogram weight of subject (kg), of $1\times10^{13}$ vg/kg to $5\times10^{13}$ vg/kg, $5\times10^{13}$ vg/kg to $9\times10^{13}$ vg/kg, $9\times10^{13}$ vg/kg or to $5\times10^{14}$ vg/kg. In some embodiments, detectable expression of LAMP-2B in heart tissue occurs at doses, in vector genomes (vg) per kilogram weight of subject (kg), of $1\times10^{13}$ vg/kg to $9\times10^{13}$ vg/kg, or $9\times10^{13}$ vg/kg or to $5\times10^{14}$ vg/kg.

In some embodiments, detectable expression of LAMP-2B in heart tissue occurs at doses, in vector genomes (vg) per kilogram weight of subject (kg), of $1\times10^{13}$ vg/kg to $5\times10^{13}$ vg/kg, $5\times10^{13}$ vg/kg to $1\times10^{14}$ vg/kg, or $1\times10^{14}$ vg/kg to $5\times10^{14}$ vg/kg.

In some embodiments, detectable expression of LAMP-2B in heart tissue occurs at doses, in vector genomes (vg) per kilogram weight of subject (kg), of $1\times10^{13}$ vg/kg to $5\times10^{14}$ vg/kg. In some embodiments, detectable expression of LAMP-2B in heart tissue occurs at doses, in vector genomes (vg) per kilogram weight of subject (kg), of $1\times10^{13}$ vg/kg to $1\times10^{14}$.

In various embodiments, the pharmaceutical compositions contain vehicles (e.g., carriers, diluents and excipients) that are pharmaceutically acceptable for a formulation capable of being injected. Exemplary excipients include a poloxamer. Formulation buffers for viral vectors (including AAV) general contains salts to prevent aggregation and other excipients (e.g. poloxamer) to reduce stickiness of the vector. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. Advantageously, the formulation is stable for storage and use when frozen (e.g. at less than 0° C., about −60° C., or about −72° C.).

Exemplary methods of treating lysosomal disorders and/or Danon disease are provided in WO 2018/170239 A1, which is incorporated herein in its entirety. The transgenes, expression cassettes, and vectors of the disclosure are useful for both in vivo (e.g. systemic, particularly intravenous use) and also ex vivo use. LAMP-2B transgene and a functional promoter can be used to ex vivo gene-correct patients' autologous hematopoietic stem and progenitor cells (HSPCs), which can then be re-transplanted in the patients to repopulate their bone marrow, which is a reservoir of "healthy" cells for the rest of the life of the patients. In some embodiments, lentiviral vectors are used for ex vivo gene corrected, but other non-viral or viral vectors may be used in place of a lentiviral vector. The disclosure envisions allogeneic transplant using donor HSPCs. In some embodiments, the lentiviral vector is a self-inactivating (SIN) lentivirus vector. In some embodiments, the HSPCs are derived from peripheral blood mobilized using, e.g., granulocyte-colony stimulating factor (G-CSF) and/or plerixafor.

In another aspect, the disclosure provides methods of preventing, mitigating, ameliorating, reducing, inhibiting, eliminating and/or reversing one or more symptoms of Danon disease or another autophagy disorder in a subject in need thereof, comprising administering to the subject a gene therapy vector of the disclosure. The term "Danon disease" refers to an X-linked dominant skeletal and cardiac muscle disorder with multisystem clinical manifestations. Danon disease mutations lead to an absence of lysosome-associated membrane protein 2 (LAMP-2) protein expression. Major clinical features include skeletal and cardiac myopathy, cardiac conduction abnormalities, cognitive difficulties, and retinal disease. Men are typically affected earlier and more severely than women.

In an embodiment, the vector is administered via a route selected from the group consisting of parenteral, intravenous, intra-arterial, intracardiac, intracoronary, intramyocardial, intrarenal, intraurethral, epidural, and intramuscular. In an embodiment, the vector is administered multiple times. In an embodiment, the vector is administered by intramuscular injection of the vector. In an embodiment, the vector is administered by injection of the vector into skeletal muscle. In an embodiment, the expression cassette comprises a muscle-specific promoter, optionally a muscle creatine kinase (MCK) promoter or a MCK/SV40 hybrid promoter as described in Takeshita et al. Muscle creatine kinase/SV40 hybrid promoter for muscle-targeted long-term transgene expression. *Int J Mol Med.* 2007 February; 19(2):309-15. In an embodiment, the vector is administered by intracardiac injection.

In an embodiment, the vector, e.g., AAV vector, is administered systemically, and more particularly, intravenously. Advantageously, the vector is administered at a dose (in vg per mL, vg/kg body mass, or vg/min/kg) less than the dose required to observe the same response when an original or wild-type LAMP-2B sequence is used. In particular embodiments, the vector is an AAV2/9 vector comprising an expression cassette comprising a polynucleotide encoding LAMP-2B disclosed herein.

In some embodiments, the disclosure provides a method of expressing LAMP-2B in a subject, comprising systemically administering an adeno-associated viral (AAV) vector to the subject, wherein the AAV vector comprises an expression cassette comprising a transgene sharing at least 95% identity with SEQ ID NO: 3 or is identical to SEQ ID NO: 3, the transgene operatively linked to an enhancer/promoter region, wherein systemic administration of the AAV vector to the subject results in increased expression of LAMP-2B compared to expression of LAMP-2B prior to administration of the AAV vector or expression of LAMP-2B in an untreated control subject. In some embodiments, the AAV vector is an AAV2/9 vector. In particular embodiments, the expression cassette comprises any of the elements disclosed herein. In some embodiment, systemic administration comprises intravenous administration. In some embodiments, the subject is exhibiting symptoms of Danon disease. In some embodiments, the subject suffers from, or is at risk for, Danon disease.

In some embodiments, the AAV vector is administered at a dose of between about $1\times10^{12}$ and $5\times10^{14}$ vector genomes (vg) of the AAV vector per kilogram (vg) of total body mass of the subject (vg/kg). In some embodiments, the AAV vector is administered at a dose of between about $1\times10^{13}$ and $5\times10^{14}$ vg/kg. In some embodiments, the AAV vector is administered at a dose of between about $5\times10^{13}$ and $3\times10^{14}$ vg/kg. In some embodiments, the AAV vector is administered at a dose of between about $5\times10^{13}$ and $1\times10^{14}$ vg/kg. In some embodiments, the AAV vector is administered at a dose of less than about $1\times10^{12}$ vg/kg, less than about $3\times10^{12}$ vg/kg, less than about $5\times10^{12}$ vg/kg, less than about $7\times10^{12}$ vg/kg, less than about $1\times10^{13}$ vg/kg, less than about $3\times10^{13}$ vg/kg, less than about $5\times10^{13}$ vg/kg, less than about $7\times10^{13}$ vg/kg, less than about $1\times10^{14}$ vg/kg, less than about $3\times10^{14}$ vg/kg, less than about $5\times10^{14}$ vg/kg, less than about $7\times10^{14}$ vg/kg, less than about $1\times10^{15}$ vg/kg, less than about $3\times10^{15}$ vg/kg, less than about $5\times10^{15}$ vg/kg, or less than about $7\times10^{15}$ vg/kg.

In some embodiments, the AAV vector is administered at a dose of about $1\times10^{12}$ vg/kg, about $3\times10^{12}$ vg/kg, about $5\times10^{12}$ vg/kg, about $7\times10^{12}$ vg/kg, about $1\times10^{13}$ vg/kg, about $3\times10^{13}$ vg/kg, about $5\times10^{13}$ vg/kg, about $7\times10^{13}$ vg/kg, about $1\times10^{14}$ vg/kg, about $3\times10^{14}$ vg/kg, about $5 \times 10^{14}$ vg/kg, about $7 \times 10^{14}$ vg/kg, about $1 \times 10^{15}$ vg/kg, about $3 \times 10^{15}$ vg/kg, about $5 \times 10^{15}$ vg/kg, or about $7 \times 10^{15}$ vg/kg.

In some embodiments, the AAV vector is administered at a dose of $1 \times 10^{12}$ vg/kg, $3 \times 10^{12}$ vg/kg, $5 \times 10^{12}$ vg/kg, $7 \times 10^{12}$ vg/kg $1 \times 10^{13}$ vg/kg $3 \times 10^{13}$ vg/kg $5 \times 10^{13}$ vg/kg $7 \times 10^{13}$ vg/kg, $1 \times 10^{14}$ vg/kg, $3 \times 10^{14}$ vg/kg, $5 \times 10^{14}$ vg/kg, $7 \times 10^{14}$ vg/kg, $1 \times 10^{15}$ vg/kg, $3 \times 10^{15}$ vg/kg, $5 \times 10^{15}$ vg/kg, or $7 \times 10^{15}$ vg/kg.

In some embodiments, the lentiviral vector is administered at a dose of between about $1 \times 10^{12}$ and $5 \times 10^{14}$ vector genomes (vg) of the lentiviral vector per kilogram (vg) of total body mass of the subject (vg/kg). In some embodiments, the lentiviral vector is administered at a dose of between about $1 \times 10^{13}$ and $5 \times 10^{14}$ vg/kg. In some embodiments, the lentiviral vector is administered at a dose of between about $5 \times 10^{13}$ and $3 \times 10^{14}$ vg/kg. In some embodiments, the lentiviral vector is administered at a dose of between about $5 \times 10^{13}$ and $1 \times 10^{14}$ vg/kg. In some embodiments, the lentiviral vector is administered at a dose of less than about $1 \times 10^{12}$ vg/kg, less than about $3 \times 10^{12}$ vg/kg, less than about $5 \times 10^{12}$ vg/kg, less than about $7 \times 10^{12}$ vg/kg, less than about $1 \times 10^{13}$ vg/kg, less than about $3 \times 10^{13}$ vg/kg, less than about $5 \times 10^{13}$ vg/kg, less than about $7 \times 10^{13}$ vg/kg, less than about $1 \times 10^{14}$ vg/kg, less than about $3 \times 10^{14}$ vg/kg, less than about $5 \times 10^{14}$ vg/kg, less than about $7 \times 10^{14}$ vg/kg, less than about $1 \times 10^{15}$ vg/kg, less than about $3 \times 10^{15}$ vg/kg, less than about $5 \times 10^{15}$ vg/kg, or less than about $7 \times 10^{15}$ vg/kg.

In some embodiments, the lentiviral vector is administered at a dose of about $1 \times 10^{12}$ vg/kg, about $3 \times 10^{12}$ vg/kg, about $5 \times 10^{12}$ vg/kg, about $7 \times 10^{12}$ vg/kg, about $1 \times 10^{13}$ vg/kg, about $3 \times 10^{13}$ vg/kg, about $5 \times 10^{13}$ vg/kg, about $7 \times 10^{13}$ vg/kg, about $1 \times 10^{14}$ vg/kg, about $3 \times 10^{14}$ vg/kg, about $5 \times 10^{14}$ vg/kg, about $7 \times 10^{14}$ vg/kg, about $1 \times 10^{15}$ vg/kg, about $3 \times 10^{15}$ vg/kg, about $5 \times 10^{15}$ vg/kg, or about $7 \times 10^{15}$ vg/kg.

In some embodiments, the lentiviral vector is administered at a dose of $1 \times 10^{12}$ vg/kg, $3 \times 10^{12}$ vg/kg, $5 \times 10^{12}$ vg/kg, $7 \times 10^{12}$ vg/kg, $1 \times 10^{13}$ vg/kg, $3 \times 10^{13}$ vg/kg, $5 \times 10^{13}$ vg/kg, $7 \times 10^{13}$ vg/kg, $1 \times 10^{14}$ vg/kg, $3 \times 10^{14}$ vg/kg, $5 \times 10^{14}$ vg/kg, $7 \times 10^{14}$ vg/kg, $1 \times 10^{15}$ vg/kg, $3 \times 10^{15}$ vg/kg, $5 \times 10^{15}$ vg/kg, or $7 \times 10^{15}$ vg/kg.

In some embodiments, the viral vector is administered at a dose of between about $1 \times 10^{12}$ and $5 \times 10^{14}$ vector genomes (vg) of the viral vector per kilogram (vg) of total body mass of the subject (vg/kg). In some embodiments, the viral vector is administered at a dose of between about $1 \times 10^{13}$ and $5 \times 10^{14}$ vg/kg. In some embodiments, the viral vector is administered at a dose of between about $5 \times 10^{13}$ and $3 \times 10^{14}$ vg/kg. In some embodiments, the viral vector is administered at a dose of between about $5 \times 10^{13}$ and $1 \times 10^{14}$ vg/kg. In some embodiments, the viral vector is administered at a dose of less than about $1 \times 10^{12}$ vg/kg, less than about $3 \times 10^{12}$ vg/kg, less than about $5 \times 10^{12}$ vg/kg, less than about $7 \times 10^{12}$ vg/kg, less than about $1 \times 10^{13}$ vg/kg, less than about $3 \times 10^{13}$ vg/kg, less than about $5 \times 10^{13}$ vg/kg, less than about $7 \times 10^{13}$ vg/kg, less than about $1 \times 10^{14}$ vg/kg, less than about $3 \times 10^{14}$ vg/kg, less than about $5 \times 10^{14}$ vg/kg, less than about $7 \times 10^{14}$ vg/kg, less than about $1 \times 10^{15}$ vg/kg, less than about $3 \times 10^{15}$ vg/kg, less than about $5 \times 10^{15}$ vg/kg, or less than about $7 \times 10^{15}$ vg/kg.

In some embodiments, the viral vector is administered at a dose of about $1 \times 10^{12}$ vg/kg, about $3 \times 10^{12}$ vg/kg, about $5 \times 10^{12}$ vg/kg, about $7 \times 10^{12}$ vg/kg, about $1 \times 10^{13}$ vg/kg, about $3 \times 10^{13}$ vg/kg, about $5 \times 10^{13}$ vg/kg, about $7 \times 10^{13}$ vg/kg, about $1 \times 10^{14}$ vg/kg, about $3 \times 10^{14}$ vg/kg, about $5 \times 10^{14}$ vg/kg, about $7 \times 10^{14}$ vg/kg, about $1 \times 10^{15}$ vg/kg, about $3 \times 10^{15}$ vg/kg, about $5 \times 10^{15}$ vg/kg, or about $7 \times 10^{15}$ vg/kg.

In some embodiments, the viral vector is administered at a dose of $1 \times 10^{12}$ vg/kg, $3 \times 10^{12}$ vg/kg, $5 \times 10^{12}$ vg/kg, $7 \times 10^{12}$ vg/kg, $1 \times 10^{13}$ vg/kg, $3 \times 10^{13}$ vg/kg, $5 \times 10^{13}$ vg/kg, $7 \times 10^{13}$ vg/kg, $1 \times 10^{14}$ vg/kg, $3 \times 10^{14}$ vg/kg, $5 \times 10^{14}$ vg/kg, $7 \times 10^{14}$ vg/kg, $1 \times 10^{15}$ vg/kg, $3 \times 10^{15}$ vg/kg, $5 \times 10^{15}$ vg/kg, or $7 \times 10^{15}$ vg/kg.

In some embodiments, the AAV vector is administered systemically at a dose of between about $1 \times 10^{12}$ and $5 \times 10^{14}$ vector genomes (vg) of the AAV vector per kilogram (vg) of total body mass of the subject (vg/kg). In some embodiments, the AAV vector is administered systemically at a dose of between about $1 \times 10^{13}$ and $5 \times 10^{14}$ vg/kg. In some embodiments, the AAV vector is administered systemically at a dose of between about $5 \times 10^{13}$ and $3 \times 10^{14}$ vg/kg. In some embodiments, the AAV vector is administered systemically at a dose of between about $5 \times 10^{13}$ and $1 \times 10^{14}$ vg/kg. In some embodiments, the AAV vector is administered systemically at a dose of less than about $1 \times 10^{12}$ vg/kg, less than about $3 \times 10^{12}$ vg/kg, less than about $5 \times 10^{12}$ vg/kg, less than about $7 \times 10^{12}$ vg/kg, less than about $1 \times 10^{13}$ vg/kg, less than about $3 \times 10^{13}$ vg/kg, less than about $5 \times 10^{13}$ vg/kg, less than about $7 \times 10^{13}$ vg/kg, less than about $1 \times 10^{14}$ vg/kg, less than about $3 \times 10^{14}$ vg/kg, less than about $5 \times 10^{14}$ vg/kg, less than about $7 \times 10^{14}$ vg/kg, less than about $1 \times 10^{15}$ vg/kg, less than about $3 \times 10^{15}$ vg/kg, less than about $5 \times 10^{15}$ vg/kg, or less than about $7 \times 10^{15}$ vg/kg.

In some embodiments, the AAV vector is administered systemically at a dose of about $1 \times 10^{12}$ vg/kg, about $3 \times 10^{12}$ vg/kg, about $5 \times 10^{12}$ vg/kg, about $7 \times 10^{12}$ vg/kg, about $1 \times 10^{13}$ vg/kg, about $3 \times 10^{13}$ vg/kg, about $5 \times 10^{13}$ vg/kg, about $7 \times 10^{13}$ vg/kg, about $1 \times 10^{14}$ vg/kg, about $3 \times 10^{14}$ vg/kg, about $5 \times 10^{14}$ vg/kg, about $7 \times 10^{14}$ vg/kg, about $1 \times 10^{15}$ vg/kg, about $3 \times 10^{15}$ vg/kg, about $5 \times 10^{15}$ vg/kg, or about $7 \times 10^{15}$ vg/kg.

In some embodiments, the AAV vector is administered systemically at a dose of $1 \times 10^{12}$ vg/kg, $3 \times 10^{12}$ vg/kg, $5 \times 10^{12}$ vg/kg, $7 \times 10^{12}$ vg/kg, $1 \times 10^{13}$ vg/kg, $3 \times 10^{13}$ vg/kg, $5 \times 10^{13}$ vg/kg, $7 \times 10^{13}$ vg/kg, $1 \times 10^{14}$ vg/kg, $3 \times 10^{14}$ vg/kg, $5 \times 10^{14}$ vg/kg, $7 \times 10^{14}$ vg/kg, $1 \times 10^{15}$ vg/kg, $3 \times 10^{15}$ vg/kg, $5 \times 10^{15}$ vg/kg, or $7 \times 10^{15}$ vg/kg.

In some embodiments, the lentiviral vector is administered systemically at a dose of between about $1 \times 10^{12}$ and $5 \times 10^{14}$ vector genomes (vg) of the lentiviral vector per kilogram (vg) of total body mass of the subject (vg/kg). In some embodiments, the lentiviral vector is administered systemically at a dose of between about $1 \times 10^{13}$ and $5 \times 10^{14}$ vg/kg. In some embodiments, the lentiviral vector is administered systemically at a dose of between about $5 \times 10^{13}$ and $3 \times 10^{14}$ vg/kg. In some embodiments, the lentiviral vector is administered systemically at a dose of between about $5 \times 10^{13}$ and $1 \times 10^{14}$ vg/kg. In some embodiments, the lentiviral vector is administered systemically at a dose of less than about $1 \times 10^{12}$ vg/kg, less than about $3 \times 10^{12}$ vg/kg, less than about $5 \times 10^{12}$ vg/kg, less than about $7 \times 10^{12}$ vg/kg, less than about $1 \times 10^{13}$ vg/kg, less than about $3 \times 10^{13}$ vg/kg, less than about $5 \times 10^{13}$ vg/kg, less than about $7 \times 10^{13}$ vg/kg, less than about $1 \times 10^{14}$ vg/kg, less than about $3 \times 10^{14}$ vg/kg, less than about $5 \times 10^{14}$ vg/kg, less than about $7 \times 10^{14}$ vg/kg, less than about $1 \times 10^{15}$ vg/kg, less than about $3 \times 10^{15}$ vg/kg, less than about $5 \times 10^{15}$ vg/kg, or less than about $7 \times 10^{15}$ vg/kg.

In some embodiments, the lentiviral vector is administered systemically at a dose of about $1 \times 10^{12}$ vg/kg, about $3 \times 10^{12}$ vg/kg, about $5 \times 10^{12}$ vg/kg, about $7 \times 10^{12}$ vg/kg, about $1 \times 10^{13}$ vg/kg, about $3 \times 10^{13}$ vg/kg, about $5 \times 10^{13}$ vg/kg, about $7\times10^{13}$ vg/kg, about $1\times10^{14}$ vg/kg, about $3\times10^{14}$ vg/kg, about $5\times10^{14}$ vg/kg, about $7\times10^{14}$ vg/kg, about $1\times10^{15}$ vg/kg, about $3\times10^{15}$ vg/kg, about $5\times10^{15}$ vg/kg, or about $7\times10^{15}$ vg/kg.

In some embodiments, the lentiviral vector is administered systemically at a dose of $1\times10^{12}$ vg/kg, $3\times10^{12}$ vg/kg, $5\times10^{12}$ vg/kg, $7\times10^{12}$ vg/kg, $1\times10^{13}$ vg/kg, $3\times10^{13}$ vg/kg, $5\times10^{13}$ vg/kg, $7\times10^{13}$ vg/kg, $1\times10^{14}$ vg/kg, $3\times10^{14}$ vg/kg, $5\times10^{14}$ vg/kg, $7\times10^{14}$ vg/kg, $1\times10^{15}$ vg/kg, $3\times10^{15}$ vg/kg, $5\times10^{15}$ vg/kg, or $7\times10^{15}$ vg/kg.

In some embodiments, the viral vector is administered systemically at a dose of between about $1\times10^{12}$ and $5\times10^{14}$ vector genomes (vg) of the viral vector per kilogram (vg) of total body mass of the subject (vg/kg). In some embodiments, the viral vector is administered systemically at a dose of between about $1\times10^{13}$ and $5\times10^{14}$ vg/kg. In some embodiments, the viral vector is administered systemically at a dose of between about $5\times10^{13}$ and $3\times10^{14}$ vg/kg. In some embodiments, the viral vector is administered systemically at a dose of between about $5\times10^{13}$ and $1\times10^{14}$ vg/kg. In some embodiments, the viral vector is administered systemically at a dose of less than about $1\times10^{12}$ vg/kg, less than about $3\times10^{12}$ vg/kg, less than about $5\times10^{12}$ vg/kg, less than about $7\times10^{12}$ vg/kg, less than about $1\times10^{13}$ vg/kg, less than about $3\times10^{13}$ vg/kg, less than about $5\times10^{13}$ vg/kg, less than about $7\times10^{13}$ vg/kg, less than about $1\times10^{14}$ vg/kg, less than about $3\times10^{14}$ vg/kg, less than about $5\times10^{14}$ vg/kg, less than about $7\times10^{14}$ vg/kg, less than about $1\times10^{15}$ vg/kg, less than about $3\times10^{15}$ vg/kg, less than about $5\times10^{15}$ vg/kg, or less than about $7\times10^{15}$ vg/kg.

In some embodiments, the viral vector is administered systemically at a dose of about $1\times10^{12}$ vg/kg, about $3\times10^{12}$ vg/kg, about $5\times10^{12}$ vg/kg, about $7\times10^{12}$ vg/kg, about $1\times10^{13}$ vg/kg, about $3\times10^{13}$ vg/kg, about $5\times10^{13}$ vg/kg, about $7\times10^{13}$ vg/kg, about $1\times10^{14}$ vg/kg, about $3\times10^{14}$ vg/kg, about $5\times10^{14}$ vg/kg, about $7\times10^{14}$ vg/kg, about $1\times10^{15}$ vg/kg, about $3\times10^{15}$ vg/kg, about $5\times10^{15}$ vg/kg, or about $7\times10^{15}$ vg/kg.

In some embodiments, the viral vector is administered systemically at a dose of $1\times10^{12}$ vg/kg, $3\times10^{12}$ vg/kg, $5\times10^{12}$ vg/kg, $7\times10^{12}$ vg/kg, $1\times10^{13}$ vg/kg, $3\times10^{13}$ vg/kg, $5\times10^{13}$ vg/kg, $7\times10^{13}$ vg/kg, $1\times10^{14}$ vg/kg, $3\times10^{14}$ vg/kg, $5\times10^{14}$ vg/kg, $7\times10^{14}$ vg/kg, $1\times10^{15}$ vg/kg, $3\times10^{15}$ vg/kg, $5\times10^{15}$ vg/kg, or $7\times10^{15}$ vg/kg.

In some embodiments, the AAV vector is administered intravenously at a dose of between about $1\times10^{12}$ and $5\times10^{14}$ vector genomes (vg) of the AAV vector per kilogram (vg) of total body mass of the subject (vg/kg). In some embodiments, the AAV vector is administered intravenously at a dose of between about $1\times10^{13}$ and $5\times10^{14}$ vg/kg. In some embodiments, the AAV vector is administered intravenously at a dose of between about $5\times10^{13}$ and $3\times10^{14}$ vg/kg. In some embodiments, the AAV vector is administered intravenously at a dose of between about $5\times10^{13}$ and $1\times10^{14}$ vg/kg. In some embodiments, the AAV vector is administered intravenously at a dose of less than about $1\times10^{12}$ vg/kg, less than about $3\times10^{12}$ vg/kg, less than about $5\times10^{12}$ vg/kg, less than about $7\times10^{12}$ vg/kg, less than about $1\times10^{13}$ vg/kg, less than about $3\times10^{13}$ vg/kg, less than about $5\times10^{13}$ vg/kg, less than about $7\times10^{13}$ vg/kg, less than about $1\times10^{14}$ vg/kg, less than about $3\times10^{14}$ vg/kg, less than about $5\times10^{14}$ vg/kg, less than about $7\times10^{14}$ vg/kg, less than about $1\times10^{15}$ vg/kg, less than about $3\times10^{15}$ vg/kg, less than about $5\times10^{15}$ vg/kg, or less than about $7\times10^{15}$ vg/kg.

In some embodiments, the AAV vector is administered intravenously at a dose of about $1\times10^{12}$ vg/kg, about $3\times10^{12}$ vg/kg, about $5\times10^{12}$ vg/kg, about $7\times10^{12}$ vg/kg, about $1\times10^{13}$ vg/kg, about $3\times10^{13}$ vg/kg, about $5\times10^{13}$ vg/kg, about $7\times10^{13}$ vg/kg, about $1\times10^{14}$ vg/kg, about $3\times10^{14}$ vg/kg, about $5\times10^{14}$ vg/kg, about $7\times10^{14}$ vg/kg, about $1\times10^{15}$ vg/kg, about $3\times10^{15}$ vg/kg, about $5\times10^{15}$ vg/kg, or about $7\times10^{15}$ vg/kg.

In some embodiments, the AAV vector is administered intravenously at a dose of $1\times10^{12}$ vg/kg, $3\times10^{12}$ vg/kg, $5\times10^{12}$ vg/kg, $7\times10^{12}$ vg/kg, $1\times10^{13}$ vg/kg, $3\times10^{13}$ vg/kg, $5\times10^{13}$ vg/kg, $7\times10^{13}$ vg/kg, $1\times10^{14}$ vg/kg, $3\times10^{14}$ vg/kg, $5\times10^{14}$ vg/kg, $7\times10^{14}$ vg/kg, $1\times10^{15}$ vg/kg, $3\times10^{15}$ vg/kg, $5\times10^{15}$ vg/kg, or $7\times10^{15}$ vg/kg.

In some embodiments, the lentiviral vector is administered intravenously at a dose of between about $1\times10^{12}$ and $5\times10^{14}$ vector genomes (vg) of the lentiviral vector per kilogram (vg) of total body mass of the subject (vg/kg). In some embodiments, the lentiviral vector is administered intravenously at a dose of between about $1\times10^{13}$ and $5\times10^{14}$ vg/kg. In some embodiments, the lentiviral vector is administered intravenously at a dose of between about $5\times10^{13}$ and $3\times10^{14}$ vg/kg. In some embodiments, the lentiviral vector is administered intravenously at a dose of between about $5\times10^{13}$ and $1\times10^{14}$ vg/kg. In some embodiments, the lentiviral vector is administered intravenously at a dose of less than about $1\times10^{12}$ vg/kg, less than about $3\times10^{12}$ vg/kg, less than about $5\times10^{12}$ vg/kg, less than about $7\times10^{12}$ vg/kg, less than about $1\times10^{13}$ vg/kg, less than about $3\times10^{13}$ vg/kg, less than about $5\times10^{13}$ vg/kg, less than about $7\times10^{13}$ vg/kg, less than about $1\times10^{14}$ vg/kg, less than about $3\times10^{14}$ vg/kg, less than about $5\times10^{14}$ vg/kg, less than about $7\times10^{14}$ vg/kg, less than about $1\times10^{15}$ vg/kg, less than about $3\times10^{15}$ vg/kg, less than about $5\times10^{15}$ vg/kg, or less than about $7\times10^{15}$ vg/kg.

In some embodiments, the lentiviral vector is administered intravenously at a dose of about $1\times10^{12}$ vg/kg, about $3\times10^{12}$ vg/kg, about $5\times10^{12}$ vg/kg, about $7\times10^{12}$ vg/kg, about $1\times10^{13}$ vg/kg, about $3\times10^{13}$ vg/kg, about $5\times10^{13}$ vg/kg, about $7\times10^{13}$ vg/kg, about $1\times10^{14}$ vg/kg, about $3\times10^{14}$ vg/kg, about $5\times10^{14}$ vg/kg, about $7\times10^{14}$ vg/kg, about $1\times10^{15}$ vg/kg, about $3\times10^{15}$ vg/kg, about $5\times10^{15}$ vg/kg, or about $7\times10^{15}$ vg/kg.

In some embodiments, the lentiviral vector is administered intravenously at a dose of $1\times10^{12}$ vg/kg, $3\times10^{12}$ vg/kg, $5\times10^{12}$ vg/kg, $7\times10^{12}$ vg/kg, $1\times10^{13}$ vg/kg, $3\times10^{13}$ vg/kg, $5\times10^{13}$ vg/kg, $7\times10^{13}$ vg/kg, $1\times10^{14}$ vg/kg, $3\times10^{14}$ vg/kg, $5\times10^{14}$ vg/kg, $7\times10^{14}$ vg/kg, $1\times10^{15}$ vg/kg, $3\times10^{15}$ vg/kg, $5\times10^{15}$ vg/kg, or $7\times10^{15}$ vg/kg.

In some embodiments, the viral vector is administered intravenously at a dose of between about $1\times10^{12}$ and $5\times10^{14}$ vector genomes (vg) of the viral vector per kilogram (vg) of total body mass of the subject (vg/kg). In some embodiments, the viral vector is administered intravenously at a dose of between about $1\times10^{13}$ and $5\times10^{14}$ vg/kg. In some embodiments, the viral vector is administered intravenously at a dose of between about $5\times10^{13}$ and $3\times10^{14}$ vg/kg. In some embodiments, the viral vector is administered intravenously at a dose of between about $5\times10^{13}$ and $1\times10^{14}$ vg/kg. In some embodiments, the viral vector is administered intravenously at a dose of less than about $1\times10^{12}$ vg/kg, less than about $3\times10^{12}$ vg/kg, less than about $5\times10^{12}$ vg/kg, less than about $7\times10^{12}$ vg/kg, less than about $1\times10^{13}$ vg/kg, less than about $3\times10^{13}$ vg/kg, less than about $5\times10^{13}$ vg/kg, less than about $7\times10^{13}$ vg/kg, less than about $1\times10^{14}$ vg/kg, less than about $3\times10^{14}$ vg/kg, less than about $5\times10^{14}$ vg/kg, less than about $7\times10^{14}$ vg/kg, less than about $1\times10^{15}$ vg/kg, less than about $3\times10^{15}$ vg/kg, less than about $5\times10^{15}$ vg/kg, or less than about $7\times10^{15}$ vg/kg.

In some embodiments, the viral vector is administered intravenously at a dose of about $1\times10^{12}$ vg/kg, about $3\times10^{12}$ vg/kg, about $5\times10^{12}$ vg/kg, about $7\times10^{12}$ vg/kg, about $1\times10^{13}$ vg/kg, about $3\times10^{13}$ vg/kg, about $5\times10^{13}$ vg/kg, about $7\times10^{13}$ vg/kg, about $1\times10^{14}$ vg/kg, about $3\times10^{14}$ vg/kg, about $5\times10^{14}$ vg/kg, about $7\times10^{14}$ vg/kg, about $1\times10^{15}$ vg/kg, about $3\times10^{15}$ vg/kg, about $5\times10^{15}$ vg/kg, or about $7\times10^{15}$ vg/kg.

In some embodiments, the viral vector is administered intravenously at a dose of $1\times10^{12}$ vg/kg, $3\times10^{12}$ vg/kg, $5\times10^{12}$ vg/kg, $7\times10^{12}$ vg/kg, $1\times10^{13}$ vg/kg, $3\times10^{13}$ vg/kg, $5\times10^{13}$ vg/kg, $7\times10^{13}$ vg/kg, $1\times10^{14}$ vg/kg, $3\times10^{14}$ vg/kg, $5\times10^{14}$ vg/kg, $7\times10^{14}$ vg/kg, $1\times10^{15}$ vg/kg, $3\times10^{15}$ vg/kg, $5\times10^{15}$ vg/kg, or $7\times10^{15}$ vg/kg.

Systemic (or more particularly intravenous) administration in some embodiments results in expression of LAMP-2B polynucleotide as mRNA, in the form of an mRNA expressed from the transgene, in one or more tissues (e.g. heart, muscle, and/or liver) of the subject. In some embodiments, expression of the LAMP-2B polynucleotide as mRNA is increased at least about 1.2-fold, at least about 1.3-fold, at least about 1.4-fold, at least about 1.5-fold, at least about 1.6-fold, at least about 1.7-fold, at least about 1.8-fold, at least about 1.9-fold, at least about 2.0-fold, at least about 2.2-fold, at least about 2.3-fold, at least about 2.4-fold, at least about 2.5-fold, at least about 3-fold, or at least about 4-fold in the heart compared to expression in an untreated subject or a subject treated with a control vector. In some embodiments, expression of LAMP-2B polynucleotide as mRNA is increased at least 1.2-fold, at least 1.3-fold, at least 1.4-fold, at least 1.5-fold, at least 1.6-fold, at least 1.7-fold, at least 1.8-fold, at least 1.9-fold, at least 2.0-fold, at least 2.2-fold, at least 2.3-fold, at least 2.4-fold, at least 2.5-fold, at least 3-fold, or at least 4-fold in the heart compared to expression in an untreated subject or a subject treated with a control vector. In some embodiments, expression of LAMP-2B polynucleotide as mRNA is increased 1.2-fold, 1.3-fold, 1.4-fold, 1.5-fold, 1.6-fold, 1.7-fold, 1.8-fold, 1.9-fold, 2.0-fold, 2.2-fold, 2.3-fold, 2.4-fold, 2.5-fold, 3-fold, or 4-fold in the heart compared to expression in an untreated subject or a subject treated with a control vector.

In some embodiments, expression of LAMP-2B polynucleotide as mRNA is increased at least about 1.2-fold, at least about 1.3-fold, at least about 1.4-fold, at least about 1.5-fold, at least about 1.6-fold, at least about 1.7-fold, at least about 1.8-fold, at least about 1.9-fold, at least about 2.0-fold, at least about 2.2-fold, at least about 2.3-fold, at least about 2.4-fold, at least about 2.5-fold, at least about 3-fold, or at least about 4-fold in the muscle compared to expression in an untreated subject or a subject treated with a control vector. In some embodiments, expression of LAMP-2B polynucleotide as mRNA is increased at least 1.2-fold, at least 1.3-fold, at least 1.4-fold, at least 1.5-fold, at least 1.6-fold, at least 1.7-fold, at least 1.8-fold, at least 1.9-fold, at least 2.0-fold, at least 2.2-fold, at least 2.3-fold, at least 2.4-fold, at least 2.5-fold, at least 3-fold, or at least 4-fold in the muscle compared to expression in an untreated subject or a subject treated with a control vector. In some embodiments, expression of LAMP-2B polynucleotide as mRNA is increased 1.2-fold, 1.3-fold, 1.4-fold, 1.5-fold, 1.6-fold, 1.7-fold, 1.8-fold, 1.9-fold, 2.0-fold, 2.2-fold, 2.3-fold, 2.4-fold, 2.5-fold, 3-fold, or 4-fold in the muscle compared to expression in an untreated subject or a subject treated with a control vector.

In some embodiments, the LAMP-2B transgene is expressed in the heart and not expressed in the liver of the subject. In some embodiments, expression of LAMP-2B polynucleotide as mRNA is observed to be at least about 1.2-fold, at least about 1.3-fold, at least about 1.4-fold, at least about 1.5-fold, at least about 1.6-fold, at least about 1.7-fold, at least about 1.8-fold, at least about 1.9-fold, at least about 2.0-fold, at least about 2.2-fold, at least about 2.3-fold, at least about 2.4-fold, at least about 2.5-fold, at least about 3-fold, or at least about 4-fold in the heart compared to the liver. In some embodiments, expression of LAMP-2B polynucleotide as mRNA is observed to be at least 1.2-fold, at least 1.3-fold, at least 1.4-fold, at least 1.5-fold, at least 1.6-fold, at least 1.7-fold, at least 1.8-fold, at least 1.9-fold, at least 2.0-fold, at least 2.2-fold, at least 2.3-fold, at least 2.4-fold, at least 2.5-fold, at least 3-fold, or at least 4-fold in the heart compared to the liver. In some embodiments, expression of LAMP-2B polynucleotide as mRNA is observed to be 1.2-fold, 1.3-fold, 1.4-fold, 1.5-fold, 1.6-fold, 1.7-fold, 1.8-fold, 1.9-fold, 2.0-fold, 2.2-fold, 2.3-fold, 2.4-fold, 2.5-fold, 3-fold, or 4-fold in the heart compared to the liver.

In some embodiments, expression of wild-type or functional LAMP-2B protein is increased at least about 1.2-fold, at least about 1.3-fold, at least about 1.4-fold, at least about 1.5-fold, at least about 1.6-fold, at least about 1.7-fold, at least about 1.8-fold, at least about 1.9-fold, at least about 2.0-fold, at least about 2.2-fold, at least about 2.3-fold, at least about 2.4-fold, at least about 2.5-fold, at least about 3-fold, or at least about 4-fold in the heart compared to expression in an untreated subject or a subject treated with a control vector. In some embodiments, expression of wild-type or functional LAMP-2B protein is increased at least 1.2-fold, at least 1.3-fold, at least 1.4-fold, at least 1.5-fold, at least 1.6-fold, at least 1.7-fold, at least 1.8-fold, at least 1.9-fold, at least 2.0-fold, at least 2.2-fold, at least 2.3-fold, at least 2.4-fold, at least 2.5-fold, at least 3-fold, or at least 4-fold in the heart compared to expression in an untreated subject or a subject treated with a control vector. In some embodiments, expression of wild-type or functional LAMP-2B protein is increased 1.2-fold, 1.3-fold, 1.4-fold, 1.5-fold, 1.6-fold, 1.7-fold, 1.8-fold, 1.9-fold, 2.0-fold, 2.2-fold, 2.3-fold, 2.4-fold, 2.5-fold, 3-fold, or 4-fold in the heart compared to expression in an untreated subject or a subject treated with a control vector.

In some embodiments, expression of wild-type or functional LAMP-2B protein is observed to be at least about 1.2-fold, at least about 1.3-fold, at least about 1.4-fold, at least about 1.5-fold, at least about 1.6-fold, at least about 1.7-fold, at least about 1.8-fold, at least about 1.9-fold, at least about 2.0-fold, at least about 2.2-fold, at least about 2.3-fold, or at least 5-fold, in the heart compared to the liver. In some embodiments, expression of wild-type or functional LAMP-2B protein is observed to be at least 1.2-fold, at least 1.3-fold, at least 1.4-fold, at least 1.5-fold, at least 1.6-fold, at least 1.7-fold, at least 1.8-fold, at least 1.9-fold, at least 2.0-fold, at least 2.2-fold, at least 2.3-fold, at least 2.4-fold, at least 2.5-fold, at least 3-fold, or at least 4-fold in the heart compared to the liver. In some embodiments, expression of wild-type or functional LAMP-2B protein is observed to be 1.2-fold, 1.3-fold, 1.4-fold, 1.5-fold, 1.6-fold, 1.7-fold, 1.8-fold, 1.9-fold, 2.0-fold, 2.2-fold, 2.3-fold, 2.4-fold, 2.5-fold, 3-fold, or 4-fold in the heart compared to the liver.

In some embodiments, administration of the gene therapy vector results in expression of wild-type or functional LAMP-2B protein in the liver of at most about 1.1-fold, at most about 1.2-fold, at most about 1.3-fold, at most about 1.4-fold, at most about 1.5-fold, at most about 1.6-fold, at most about 1.7-fold, at most about 1.8-fold, at most about 1.9-fold, or at most about 2-fold increased compared to expression in the liver of an untreated subject. In some embodiments, administration of the gene therapy vector results in expression of wild-type or functional LAMP-2B protein in the liver of at most 1.1-fold, at most 1.2-fold, at most 1.3-fold, at most 1.4-fold, at most 1.5-fold, at most 1.6-fold, at most 1.7-fold, at most 1.8-fold, at most 1.9-fold, or at most 2-fold increased compared to expression in the liver of an untreated subject. In some embodiments, administration of the gene therapy vector results in expression of wild-type or functional LAMP-2B protein in the liver of 1.1-fold, 1.2-fold, 1.3-fold, 1.4-fold, 1.5-fold, 1.6-fold, 1.7-fold, 1.8-fold, 1.9-fold, or 2-fold increased compared to expression in the liver of an untreated subject.

In an embodiment, the disclosure provides a method of treating a disease or disorder, optionally Danon disease, in a subject in need thereof, comprising contacting cells with a gene therapy vector according to the present disclosure and administering the cells to the subject. In an embodiment, the cells are stem cells, optionally pluripotent stem cells. In an embodiment, the stem cells are capable of differentiation into cardiac tissue. In an embodiment, the stem cells are capable of differentiation into muscle tissue, e.g., cardiac muscle tissue and/or skeletal muscle tissue. In an embodiment, the stem cells are autologous. In an embodiment, the stem cells are induced pluripotent stem cells (iPSCs).

In an embodiment, the disease or disorder is an autophagy disorder. In some embodiments, the autophagy disorder is selected from the group consisting of, but not limited to, end-stage heart failure, myocardial infarction, drug toxicities, diabetes, end-stage renal failure, and aging. In an embodiment, the subject is a mammal, e.g., a human. In an embodiment, the subject is exhibiting symptoms of Danon disease or another autophagy disorder. In an embodiment, the subject has been identified as having reduced or non-detectable LAMP-2 expression. In an embodiment, the subject has been identified as having a mutated LAMP-2 gene.

Subjects/patients amenable to treatment using the methods described herein include, but are not limited to, individuals at risk of a disease or disorder characterized by insufficient autophagic flux (e.g., Danon disease as well as other known disorders of autophagy including, but not limited to, systolic and diastolic heart failure, myocardial infarction, drug toxicities (for example, anthracyclines chloroquine and its derivatives), diabetes, end-stage renal disease, and aging) but not showing symptoms, as well as subjects presently showing symptoms. Such subject may have been identified as having a mutated LAMP-2 gene or as having reduced or non-detectable levels of LAMP-2 expression.

In some embodiments, the patient is a human. In some embodiments, the patient is a pediatric, adolescent, or adult human. In some embodiments, the patient is 1, 2, 3, 4, 5, 6, 7, 8, 9, 10, 11, 12, 13, 14, 15, 16, 17, 18, 19, or 20 years old, or more than 20 years old. In some embodiments, the patient is 20 to 50 years old. In some embodiments, the patient is 50 to 65 years old. In some embodiments, the patient is 1 to 5, 2 to 6, 3 to 7, 4 to 8, 5 to 9, 6 to 10, 7 to 11, 8 to 12, 9 to 13, 10 to 14, 11 to 15, 12 to 16, 13 to 17, 14 to 18, 15 to 19, or 16 to 20 years old. In some embodiments, the patient is 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, 18 to 19, 19 to 20, or 20 to 21 years old. In a particular embodiment, the patient is 15 to 16 years old.

In some embodiments, the patient is a human male. In some embodiments, the patient is a pediatric, adolescent, or adult human male. In some embodiments, the patient is a 1, 2, 3, 4, 5, 6, 7, 8, 9, 10, 11, 12, 13, 14, 15, 16, 17, 18, 19, or 20 years old male, or a more than 20 years old male. In some embodiments, the patient is a 20 to 50 years old male. In some embodiments, the patient is a 50 to 65 years old male. In some embodiments, the patient is a 1 to 5, 2 to 6, 3 to 7, 4 to 8, 5 to 9, 6 to 10, 7 to 11, 8 to 12, 9 to 13, 10 to 14, 11 to 15, 12 to 16, 13 to 17, 14 to 18, 15 to 19, or 16 to 20 years old male. In some embodiments, the patient is a 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, 18 to 19, 19 to 20, or 20 to 21 year old male. In a particular embodiment, the patient is 15 to 16 years old.

In some embodiments, the patient is a human female. In some embodiments, the patient is a pediatric, adolescent, or adult human female. In some embodiments, the patient is a 1, 2, 3, 4, 5, 6, 7, 8, 9, 10, 11, 12, 13, 14, 15, 16, 17, 18, 19, or 20 years old female, or a more than 20 years old female. In some embodiments, the patient is a 20 to 50 years old female. In some embodiments, the patient is a 50 to 65 years old female.

In some embodiments, the subject is exhibiting symptoms of a disease or disorder characterized by insufficient autophagic flux (e.g., Danon disease as well as other known disorders of autophagy including, but not limited to, systolic and diastolic heart failure, myocardial infarction, drug toxicities, diabetes, end-stage renal disease, and aging). The symptoms may be actively manifesting, or may be suppressed or controlled (e.g., by medication) or in remission. The subject may or may not have been diagnosed with the disorder, e.g., by a qualified physician.

Definitions

The terms "lysosome-associated membrane protein 2" and "LAMP-2" interchangeably refer to nucleic acids and polypeptide polymorphic variants, alleles, mutants, and interspecies homologs that: (1) have an amino acid sequence that has greater than about 90% amino acid sequence identity, for example, 91%, 92%, 93%, 94%, 95%, 96%, 97%, 98% or 99% or greater amino acid sequence identity, preferably over a region of at least about 25, 50, 100, 200, 300, 400, or more amino acids, or over the full-length, to an amino acid sequence encoded by a LAMP-2 nucleic acid (see, e.g., GenBank Accession Nos. NM_002294.2 (isoform A). NM_013995.2 (isoform B), NM_001122606.1 (isoform C)) or to an amino acid sequence of a LAMP-2 polypeptide (see e.g., GenBank Accession Nos. NP_002285.1 (isoform A), NP_054701.1 (isoform B), NP_001116078.1 (isoform C)); (2) bind to antibodies, e.g., polyclonal antibodies, raised against an immunogen comprising an amino acid sequence of a LAMP-2 polypeptide (e.g., LAMP-2 polypeptides described herein); or an amino acid sequence encoded by a LAMP-2 nucleic acid (e.g., LAMP-2 polynucleotides described herein), and conservatively modified variants thereof; (3) specifically hybridize under stringent hybridization conditions to an anti-sense strand corresponding to a nucleic acid sequence encoding a LAMP-2 protein, and conservatively modified variants thereof; (4) have a nucleic acid sequence that has greater than about 90%, preferably greater than about 91%, 92%, 93%, 94%, 95%, 96%, 97%, 98%, 99%, or higher nucleotide sequence identity, preferably over a region of at least about 25, 50, 100, 200, 500, 1000, 2000 or more nucleotides, or over the full-length, to a LAMP-2 nucleic acid (e.g., LAMP-2 polynucleotides, as described herein, and LAMP-2 polynucleotides that encode LAMP-2 polypeptides, as described herein).

The terms "lysosome-associated membrane protein 2B" and "LAMP-2B" interchangeably refer to nucleic acids and polypeptide polymorphic variants, alleles, mutants, and interspecies homologs that: (1) have an amino acid sequence that has greater than about 90% amino acid sequence identity, for example, 91%, 92%, 93%, 94%, 95%, 96%, 97%, 98% or 99% or greater amino acid sequence identity, preferably over a region of at least about 25, 50, 100, 200, 300, 400, or more amino acids, or over the full-length, to an amino acid sequence encoded by a LAMP-2B nucleic acid (see e.g., NM_013995.2) or to an amino acid sequence of a LAMP-2B polypeptide (see e.g., NP_054701.1); (2) bind to antibodies, e.g., polyclonal antibodies, raised against an immunogen comprising an amino acid sequence of a LAMP-2B polypeptide (e.g., LAMP-2B polypeptides described herein); or an amino acid sequence encoded by a LAMP-2B nucleic acid (e.g., LAMP-2B polynucleotides described herein), and conservatively modified variants thereof; (3) specifically hybridize under stringent hybridization conditions to an anti-sense strand corresponding to a nucleic acid sequence encoding a LAMP-2B protein, and conservatively modified variants thereof; (4) have a nucleic acid sequence that has greater than about 90%, preferably greater than about 91%, 92%, 93%, 94%, 95%, 96%, 97%, 98%, 99%, or higher nucleotide sequence identity, preferably over a region of at least about 25, 50, 100, 200, 500, 1000, 2000 or more nucleotides, or over the full-length, to a LAMP-2B nucleic acid (e.g., LAMP-2B polynucleotides, as described herein, and LAMP-2B polynucleotides that encode LAMP-2B polypeptides, as described herein).

The term "functional variant" in respect to a protein (e.g. a LAMP-2B) refers to a polypeptide sequence, or a fragment of a polypeptide sequence having at least about 30, at least about 40, at least about 50, at least about 60, at least about 70, or at least about 80 amino acid resides, that retains one or more functional attributes of the protein. For example, a functional variant of LAMP-2B is a LAMP-2B (as defined herein) that retains one or more functions such as: (1) regulating human cardiomyocyte function (Chi et al. (2019) PNAS USA 116 (2) 556-565); (2) improving metabolic and physiological function in Danon disease (Adler et al. (2019) *J Am. College Cardiology* S0735-1097(19)31295-1); and/or (3) autophagy (Rowland et al. (2016) *J. Cell Sci.* (2016) 129, 2135-2143).

LAMP-2B has a lumenal domain (residues 29-375), a transmembrane domain (residues 376-399), and a cytoplasmic domain (residues 400-410), see UniProt Accession No. P13473. LAMP-2B functions in include chaperone-mediated autophagy, a process that mediates lysosomal degradation of proteins in response to various stresses and as part of the normal turnover of proteins with a long biological half-live (Cuervo et al. *Science* 273:501-503 (1996), Cuervo et al. *J. Cell Sci.* 113:4441-4450 (2000), Bandyopadhyay et al. *Mol. Cell. Biol.* 28:5747-5763 (2008), Li et al. *Exp. Cell Res.* 327:48-56 (2014), Hubert et al. *Biol. Open* 5:1516-1529 (2016)). LAMP-2B may target GAPDH and MLLT11 for lysosomal degradation. LAMP-2B may be required for the fusion of autophagosomes with lysosomes during autophagy. It has been suggested that cells that lack LAMP2 express normal levels of VAMPS, but fail to accumulate STX17 on autophagosomes, which is the most likely explanation for the lack of fusion between autophagosomes and lysosomes. LAMP-2B may be required for normal degradation of the contents of autophagosomes. LAMP-2B may be required for efficient MHCII-mediated presentation of exogenous antigens via its function in lysosomal protein degradation; antigenic peptides generated by proteases in the endosomal/lysosomal compartment are captured by nascent MHCII subunits (Crotzer et al. *Immunology* 131:318-330 (2010)).

Functional variants of LAMP-2B therefore include fragments of LAMP-2B that are capable of mediating any of the foregoing functions. In some embodiments, the function fragment of LAMP-2B includes one or more of the lumenal, transmembrane, and cytoplasmic domains. In some embodiments, the functional variant of LAMP-2B comprises one or more C-terminal or N-terminal deletions with respect to native LAMP-2B. In some embodiments, the functional variant of LAMP-2B comprises one or more internal deletions with respect to native LAMP-2B.

The terms "identical" or percent "identity," in the context of two or more nucleic acids or polypeptide sequences, refer to two or more sequences or subsequences that are the same or have a specified percentage of amino acid residues or nucleotides that are the same (i.e., share at least about 80% identity, for example, at least about 85%, 90%, 91%, 92%, 93%, 94%, 95%, 96%, 97%, 98%, 99% identity over a specified region to a reference sequence, e.g., LAMP-2 polynucleotide or polypeptide sequence as described herein, when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, for example, over a region that is 50, 100, 200, 300, 400 amino acids or nucleotides in length, or over the full-length of a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to LAMP-2 nucleic acids and proteins, the BLAST and BLAST 2.0 algorithms and the default parameters are used.

A "comparison window," as used herein, includes reference to a segment of any one of the number of contiguous positions selected from the group consisting of 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., eds., Current Protocols in Molecular Biology (1995 supplement)). Examples of algorithms that are suitable for determining percent sequence identity and sequence similarity are the BLAST and BLAST 2.0 algorithms, which are described in Altschul et al., J. Mol. Biol. 215:403-410 (1990) and Altschul et al., Nucleic Acids Res. 25:3389-3402 (1977), respectively. Software for performing BLAST analyses is publicly available through the National Center for Biotechnology Information (on the worldwide web at ncbi.nlm.nih.gov/).

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions. Yet another indication that two nucleic acid sequences are substantially identical is that the same primers can be used to amplify the sequence.

As used herein, "administering" refers to local and systemic administration, e.g., including enteral, parenteral, pulmonary, and topical/transdermal administration. Routes of administration for compounds (e.g., polynucleotide encoding one or more LAMP-2 isoforms) that find use in the methods described herein include, e.g., oral (per os (P.O.)) administration, nasal or inhalation administration, administration as a suppository, topical contact, transdermal delivery (e.g., via a transdermal patch), intrathecal (IT) administration, intravenous ("iv") administration, intraperitoneal ("ip") administration, intramuscular ("im") administration, intralesional administration, or subcutaneous ("sc") administration, or the implantation of a slow-release device e.g., a mini-osmotic pump, a depot formulation, etc., to a subject. Administration can be by any route including parenteral and transmucosal (e.g., oral, nasal, vaginal, rectal, or transdermal). Parenteral administration includes, e.g., intravenous, intramuscular, intraarterial, intrarenal, intraurethral, intracardiac, intracoronary, intramyocardial, intradermal, epidural, subcutaneous, intraperitoneal, intraventricular, iontophoretic and intracranial. Other modes of delivery include, but are not limited to, the use of liposomal formulations, intravenous infusion, transdermal patches, etc.

The terms "systemic administration" and "systemically administered" refer to a method of administering a compound or composition to a mammal so that the compound or composition is delivered to sites in the body, including the targeted site of pharmaceutical action, via the circulatory system. Systemic administration includes, but is not limited to, oral, intranasal, rectal and parenteral (e.g., other than through the alimentary tract, such as intramuscular, intravenous, intra-arterial, transdermal and subcutaneous) administration.

The term "co-administering" or "concurrent administration", when used, for example with respect to the compounds (e.g., LAMP-2 polynucleotides) and/or analogs thereof and another active agent, refers to administration of the compound and/or analogs and the active agent such that both can simultaneously achieve a physiological effect. The two agents, however, need not be administered together. In certain embodiments, administration of one agent can precede administration of the other. Simultaneous physiological effect need not necessarily require presence of both agents in the circulation at the same time. However, in certain embodiments, co-administering typically results in both agents being simultaneously present in the body (e.g., in the plasma) at a significant fraction (e.g., 20% or greater, e.g., 30% or 40% or greater, e.g., 50% or 60% or greater, e.g., 70% or 80% or 90% or greater) of their maximum serum concentration for any given dose.

The term "effective amount" or "pharmaceutically effective amount" refer to the amount and/or dosage, and/or dosage regime of one or more compounds (e.g., gene therapy vectors) necessary to bring about the desired result e.g., increased expression of one or more LAMP-2 isoforms in an amount sufficient to reduce the ultimate severity of a disease characterized by impaired or deficient autophagy (e.g., Danon disease).

The phrase "cause to be administered" refers to the actions taken by a medical professional (e.g., a physician), or a person controlling medical care of a subject, that control and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like.

As used herein, the terms "treating" and "treatment" refer to delaying the onset of, retarding or reversing the progress of, reducing the severity of, or alleviating or preventing either the disease or condition to which the term applies, or one or more symptoms of such disease or condition. The terms "treating" and "treatment" also include preventing, mitigating, ameliorating, reducing, inhibiting, eliminating and/or reversing one or more symptoms of the disease or condition.

The term "mitigating" refers to reduction or elimination of one or more symptoms of that pathology or disease, and/or a reduction in the rate or delay of onset or severity of one or more symptoms of that pathology or disease, and/or the prevention of that pathology or disease. In certain embodiments, the reduction or elimination of one or more symptoms of pathology or disease can include, e.g., measurable and sustained increase in the expression levels of one or more isoforms of LAMP-2.

As used herein, the phrase "consisting essentially of refers to the genera or species of active pharmaceutical agents recited in a method or composition, and further can include other agents that, on their own do not have substantial activity for the recited indication or purpose.

The terms "subject," "individual," and "patient" interchangeably refer to a mammal, preferably a human or a non-human primate, but also domesticated mammals (e.g., canine or feline), laboratory mammals (e.g., mouse, rat, rabbit, hamster, guinea pig) and agricultural mammals (e.g., equine, bovine, porcine, ovine). In various embodiments, the subject can be a human (e.g., adult male, adult female, adolescent male, adolescent female, male child, female child).

The terms "gene transfer" or "gene delivery" refer to methods or systems for reliably inserting foreign DNA into host cells. Such methods can result in transient expression of non-integrated transferred DNA, extrachromosomal replication and expression of transferred replicons (e.g. episomes), or integration of transferred genetic material into the genomic DNA of host cells.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication or reverse transcription in a cell, or may include sequences sufficient to allow integration into host cell DNA. "vectors" include gene therapy vectors. As used herein, the term "gene therapy vector" refers to a vector capable of use in performing gene therapy, e.g., delivering a polynucleotide sequence encoding a therapeutic polypeptide to a subject. Gene therapy vectors may comprise a nucleic acid molecule ("transgene") encoding a therapeutically active polypeptide, e.g., a LAMP-2B or other gene useful for replacement gene therapy when introduced into a subject. Useful vectors include, but are not limited to, viral vectors.

As used herein, the term "expression cassette" refers to a DNA segment that is capable in an appropriate setting of driving the expression of a polynucleotide (a "transgene") encoding a therapeutically active polypeptide (e.g., LAMP-2B) that is incorporated in said expression cassette. When introduced into a host cell, an expression cassette inter alia is capable of directing the cell's machinery to transcribe the transgene into RNA, which is then usually further processed and finally translated into the therapeutically active polypeptide. The expression cassette can be comprised in a gene therapy vector. Generally, the term expression cassette excludes polynucleotide sequences 5' to the 5' ITR and 3' to the 3' ITR.

All patents, patent publications, and other publications referenced and identified in the present specification are individually and expressly incorporated herein by reference in their entirety for all purposes.

EXAMPLES

Example 1: Enhanced Gene Expression Using Lamp-2B Transgene Variants

Figure 2:
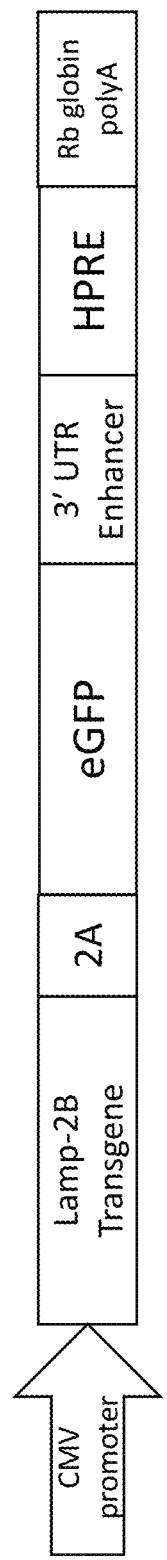
FIG. 2 shows the expression cassette of plasmid-based green fluorescence protein (GFP) reporter system used to test and compare wildtype verses codon-optimized LAMP-2B constructs.

A gene expression cassette depicted in FIG. 2 was constructed in a plasmid-based green fluorescence protein (GFP) reporter system for LAMP-2B transgene expression. The plasmid included a single open reading frame encoding the LAMP-2B transgene, a 2A peptide, and an enhanced green fluorescence protein (eGFP). Post-translational self-cleavage of the 2A peptide resulted in co-expression of LAMP-2B and eGFP in equimolar amounts. A wild-type LAMP-2B coding sequence (SEQ ID NO: 2) and three codon variants of the LAMP-2B coding sequence (codon variants 1, 2 and 3; SEQ ID NOs: 3-5, respectively) were tested as the transgenes. The three codon variants contained a reduced number of CpGs, removal of cryptic sites, and a reduced number of open reading frames as compared to the wild-type LAMP-2B coding sequence.

Forty wells of a CellBIND 96-well plate (NUNC #3300) were coated with 0.1% gelatin in water (Millipore ES-006-B) for 1 hour at room temperature. Approximately 88,000 induced pluripotent stem cell (iPSC)-derived cardiomyocytes (VWR MSPP-CMC10001) were plated into each well in plating media (VWR # M1001) at 37° C. and 5% carbon dioxide ($CO_2$). After 4 hours, the media was changed to maintenance media (VWR # M1003) that was pre-equilibrated to 37° C. and 5% $CO_2$. A transfection mixture was prepared by adding 6 μL of transfection reagent (ViaFect Promega # E4982) to 128 μL of 0.015 μg/μL plasmid (wildtype or codon variants 1, 2, or 3) in OptiMEM or OptiMEM+ViaFect only (negative control) and incubated for 10-20 min. 100 μL of this transfection mixture was added to 1 mL of maintenance media that was pre-equilibrated to 37° C. and 5% $CO_2$.

Figure 4:
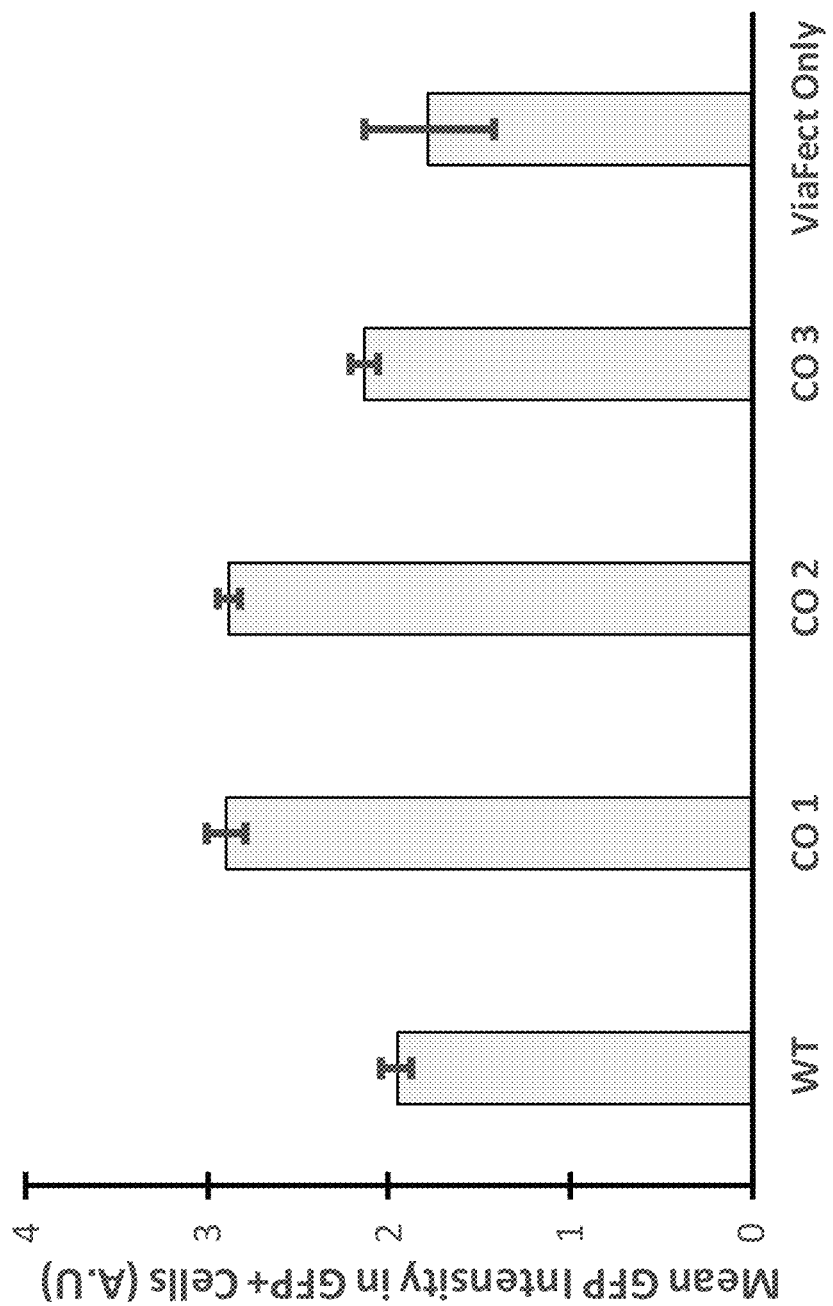
FIG. 4 is a graph showing the gene expression level in cells transfected with plasmid-based GFP reporting systems used to test LAMP-2B constructs, which is measured as mean GFP intensity of GFP+ cells in absorbance units (A.U.). GFP expression by cells transfected with a wild-type LAMP-2B construct (WT) is compared to GFP expression by three codon-optimized ("CO") constructs, CO 1, CO 2, and CO 3, or a no-vector control (labeled "ViaFect Only").
Figure 5:
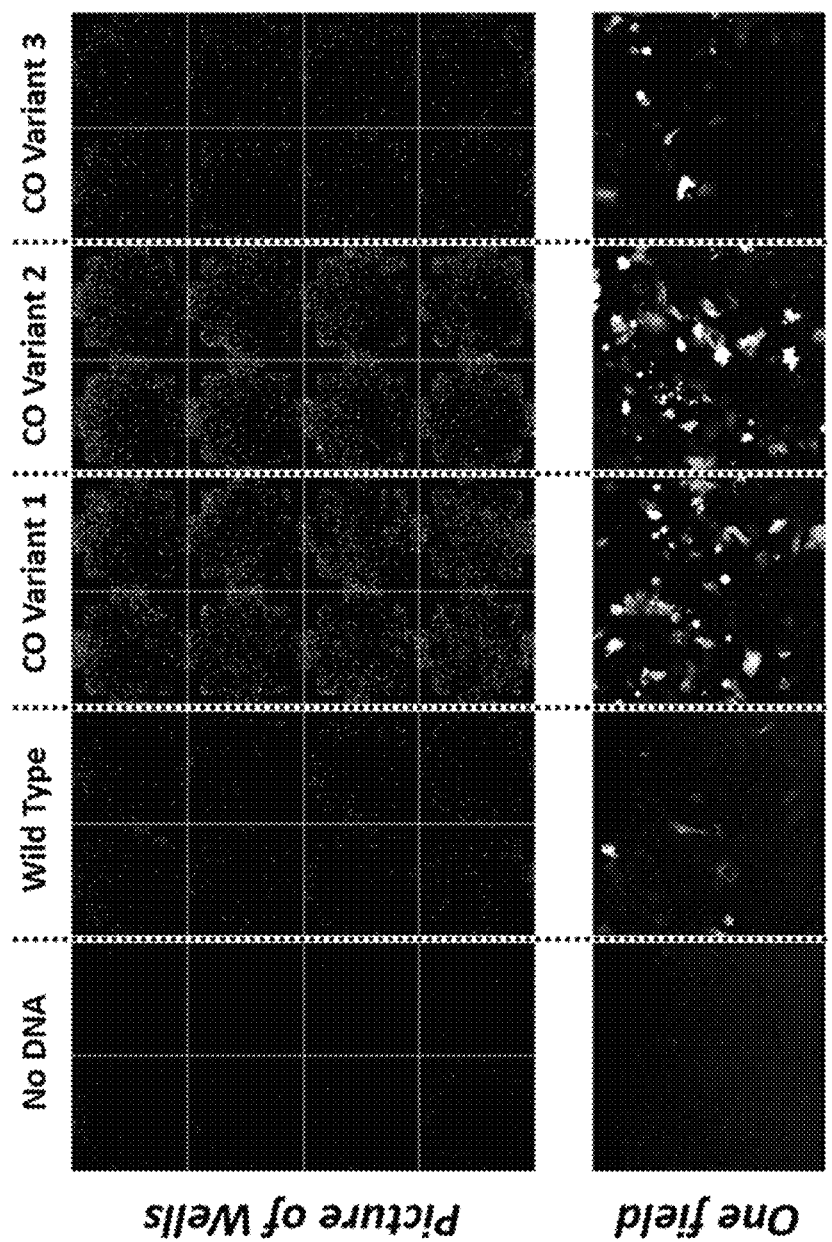
FIG. 5 shows immunofluorescence images of induced pluripotent stem cell (iPSC)-derived cardiomyocytes two days after transfection with a plasmid-based GFP reporter system. Cells were transfected with no DNA, or LAMP-2B constructs expressing wild-type LAMP-2B, the CO 1 variant, the CO 2 variant, or the CO 3 variant.
Figure 6:
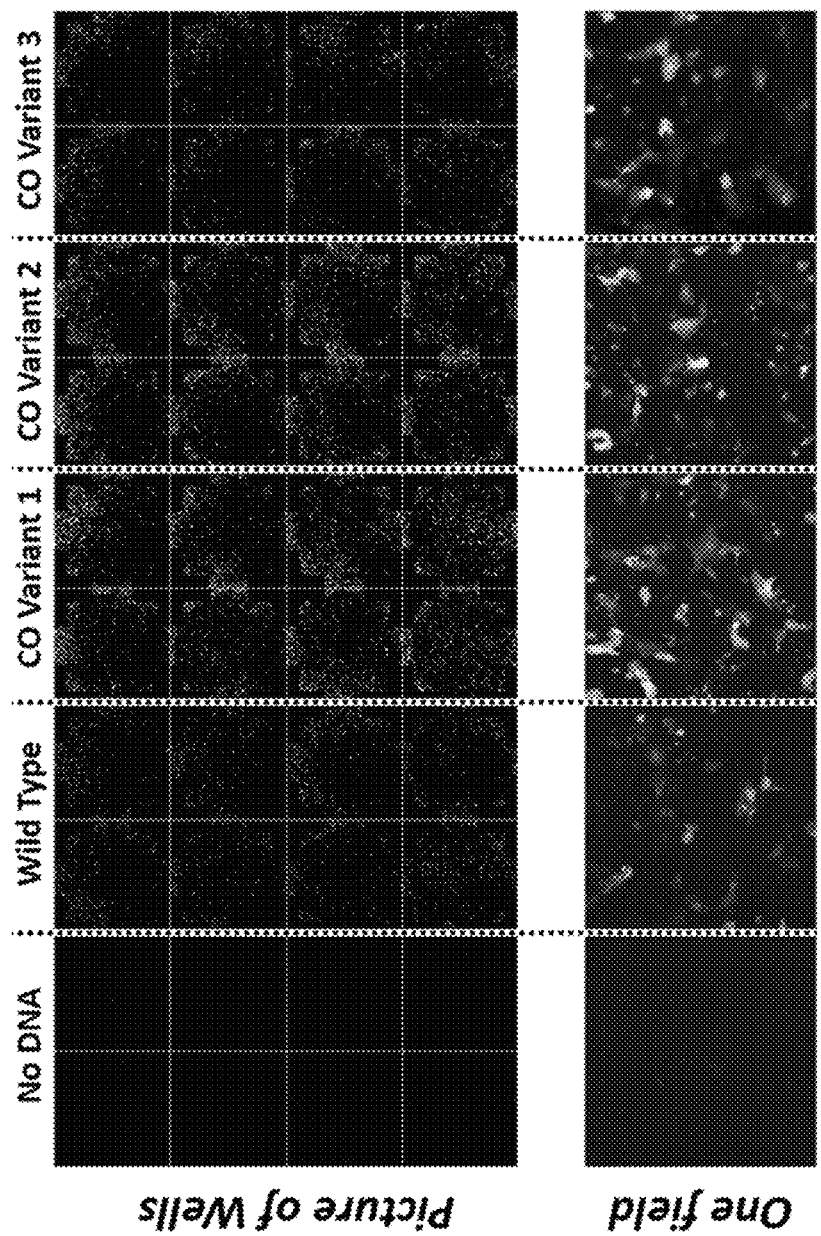
FIG. 6 shows immunofluorescence images of iPSC-derived cardiomyocytes seven days after transfection with a plasmid-based GFP reporter system. Cells were transfected with no DNA, or LAMP-2B constructs expressing wild-type LAMP-2B, the CO 1 variant, the CO 2 variant, or the CO 3 variant.

Approximately 28 hours after initial plating, 100 μL of this transfection mixture in maintenance media was added to each well. Approximately 48 hours after adding media with transfection mixture, the cells were imaged and analyzed on an automated confocal microscope (Perkin Elmer Operetta CLS, Harmony version 4.5 software) for GFP positive cells (FIG. 3) and their average fluorescent intensity (FIG. 4). Immunofluorescence images of the cells two or seven days after transfection are shown in FIG. 5 and FIG. 6, respectively.

Figure 3:
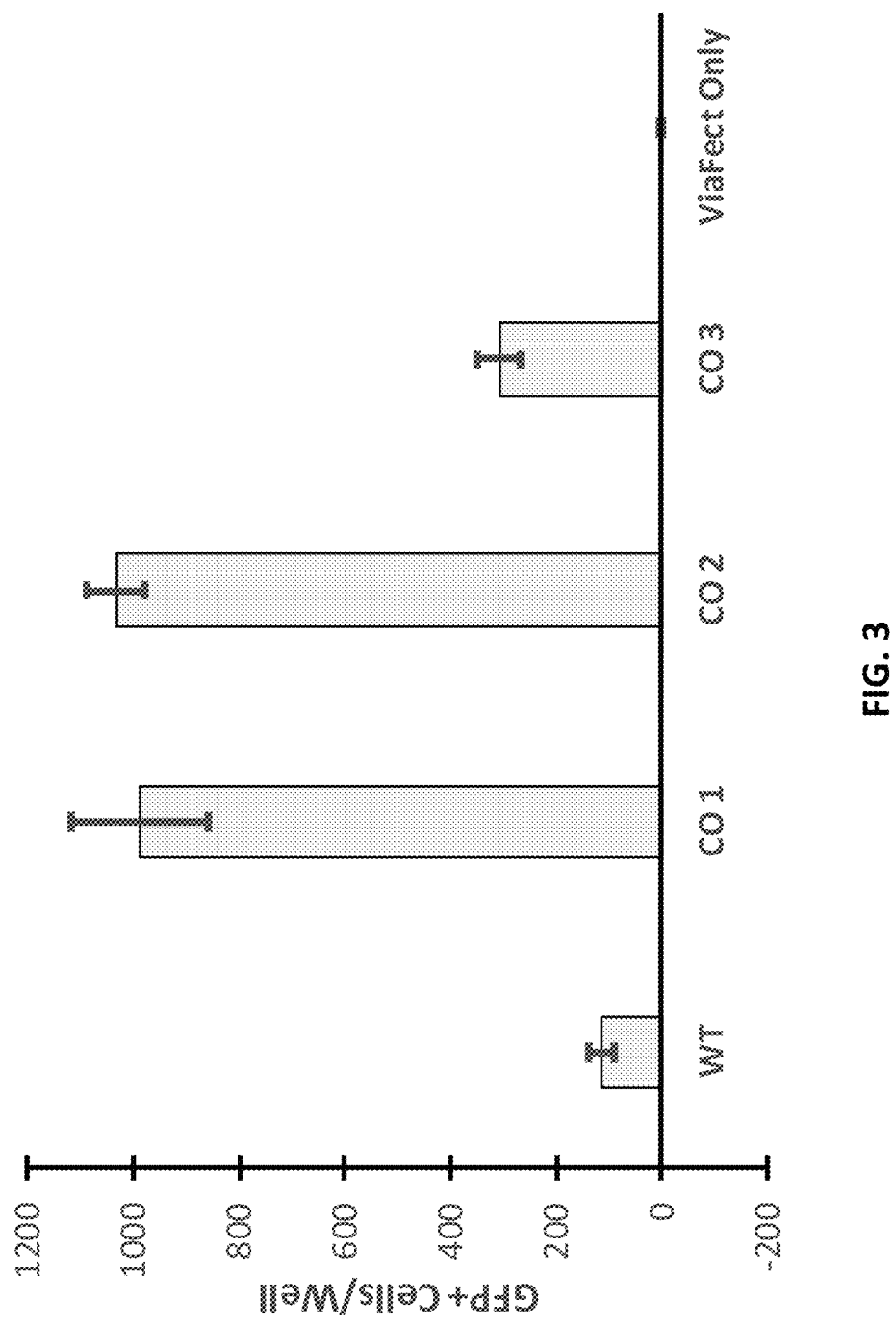
FIG. 3 is a graph showing transfection expression efficiency of LAMP-2B constructs tested using transfection of a plasmid-based GFP reporter system and measured as GFP+ cells per well. A wild-type LAMP-2B construct (WT) is compared to three codon-optimized ("CO") constructs, CO 1, CO 2, and CO 3, and a no-vector control (labeled "ViaFect Only").

FIG. 3 shows that the use of codon variants 1 ("CO 1") or 2 ("CO 2") resulted in expression of GFP in a significantly higher number of cells (~9-fold higher) as compared to the wild-type transgene. Similarly, FIG. 4 showed mean GFP intensity in cells transfected with codon variants 1 ("CO 1") and 2 ("CO 2") to be 1.5-fold higher than wild-type.

Example 2: Optimized LAMP-2B Gene Therapy Vectors

Optimized AAV gene therapy vectors are produced by inserting the LAMP-2B optimized variant, CO1 sequence described in Example 1 into the expression cassette of a recombinant AAV vector. The AAV regulatory cassette is modified by removal of upstream cryptic ATG sequence, use of an optimized consensus Kozak sequence, and/or a full-length polyadenylation sequence. The vectors are tested in comparison to control recombinant AAV vectors containing one or more additional ATG sites upstream of the transgene, a non-optimal Kozak sequence, and/or a non-full-length polyadenylation sequence. Vectors are tested in vitro in Danon patient iPSC-derived cardiomyocytes and in a LAMP-2$^{-/-}$ knockout mouse model of Danon disease. The optimized AAV gene therapy cassettes and vectors are expected to result in a higher level of expression and/or expression in a higher percentage of cells as compared to the control recombinant AAV vectors.

Example 3: In Vitro Evaluation of AAV9-LAMP-2B.v1.2

AAV gene therapy cassette and vector were produced by inserting the LAMP-2B variant sequence CO1 (SEQ ID NO: 3) into a recombinant AAV plasmid vector having no cryptic start sites upstream of the transgene, an optimized consensus Kozak sequence, and a full-length polyadenylation (polyA) sequence from rabbit globin ("LAMP-2B.v.1.2"; expression cassette: SEQ ID NO: 8). LAMP-2B.v1.2 was compared to LAMP-2B v1.0, which is the regulatory cassette having a wild-type LAMP-2B transgene (transgene sequence: SEQ ID NO: 2) without an optimal Kozak sequence and a mini-polyA.

HEK293 cells were used to generate viral particles with three-plasmid, helper virus-free system was used to generate recombinant AAV particles containing serotype 9 capsid proteins and viral genomes that have AAV2 ITRs flanking the LAMP-2B expression cassette. The expression cassette contains the human codon-optimized LAMP-2B coding sequence (v1.2 or v1.0) driven by an upstream chimeric "CAG" promoter containing the CMV IE enhancer (CMV IE), the chicken (β-actin (CBA) promoter, and a CBA intron splice donor (FIG. 1A). The expression cassette also includes a downstream WPRE element and is terminated by the rabbit beta-globin polyadenylation signal (RGpA). The HEK293 cells were transiently transfected with the LAMP-2B.v1.2 plasmid vector or the LAMP-2B.v1.0 plasmid vector, a pAAV2/9 packaging plasmid, and pAd-Helper adenovirus helper plasmid.

Figure 7B:
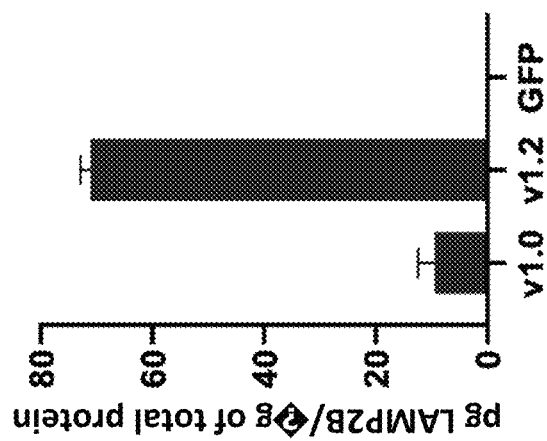
FIG. 7B shows quantification of LAMP-2B protein by ELISA in CHO-Lec2 cells transduced with AAV9-wild-type LAMP-2B (v1.0), AAV9-optimized LAMP-2B (v1.2) or AAV9-GFP (GFP) vectors.
Figure 7A:
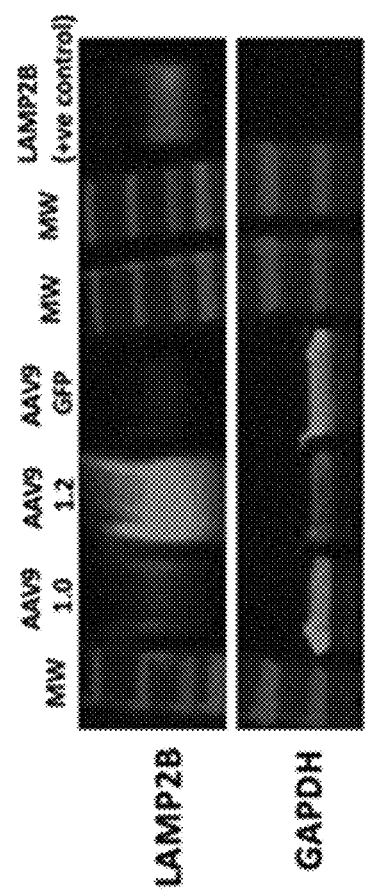
FIG. 7A shows an immunoblot of human LAMP-2B protein in CHO-Lec2 cells transduced with AAV9 viral vectors comprising the wild-type LAMP-2B v1.0 transgene (AAV9 1.0), the optimized variant LAMP-2B v1.2 transgene (AAV9 1.2) or a GFP transgene (AAV9 GFP). Molecular weight markers (MW) and a control LAMP-2B recombinant protein sample (LAMP2B (+ve control)) were also included.

CHO-Lec2 cells were seeded in a 24 well plate at $1.2 \times 10^5$ cells/mL in MEM-α containing 10% FBS and 1% Normocin. The following day, CHO-Lec2 cells were transduced in serum-free MEMα medium with either AAV9-LAMP- 2B.v1.0, AAV9-LAMP-2B.v1.2, or the same vector having GFP in place of the LAMP-2B transgene (at MOI of $3\times10^5$). Seven days post-transduction, lysates were harvested using the Mammalian Cell Lysis kit (Sigma) and total protein was quantified using the MicroBCA kit per manufacturer's instructions. Proteins were separated by SDS-PAGE, transferred onto nitrocellulose membranes and immunoblotted for LAMP-2B (1:500) and GAPDH (1:10,000). CHO-Lec2 cells transduced with AAV9-optimized LAMP-2B.v1.2 showed increased expression compared to CHO-Lec2 cells transduced with the original AAV9-wild-type LAMP-2B.v1.0 (FIG. 7A). LAMP-2B was not detected in cells transduced with AAV9-GFP vector alone (FIG. 7A).

LAMP-2B expression was also quantitated in cell lysates by ELISA. Briefly, a 96 well plate was coated with anti-LAMP-2B antibody (clone: H4B4), lysates were added to the wells, and detection was performed using anti-LAMP-2B polyclonal antibody (1:500, Thermo Fisher PA; 5-24575) followed by incubation with HRP-conjugated anti-rabbit antibody (1:3000, Sigma). Transduction with AAV9-optimized LAMP-2B.v1.2 vector resulted in an approximately 7-fold increase in LAMP-2B expression compared to cells transduced with the AAV9-wild-type LAMP-2B.v1.0 (FIG. 7B).

Figure 8A:
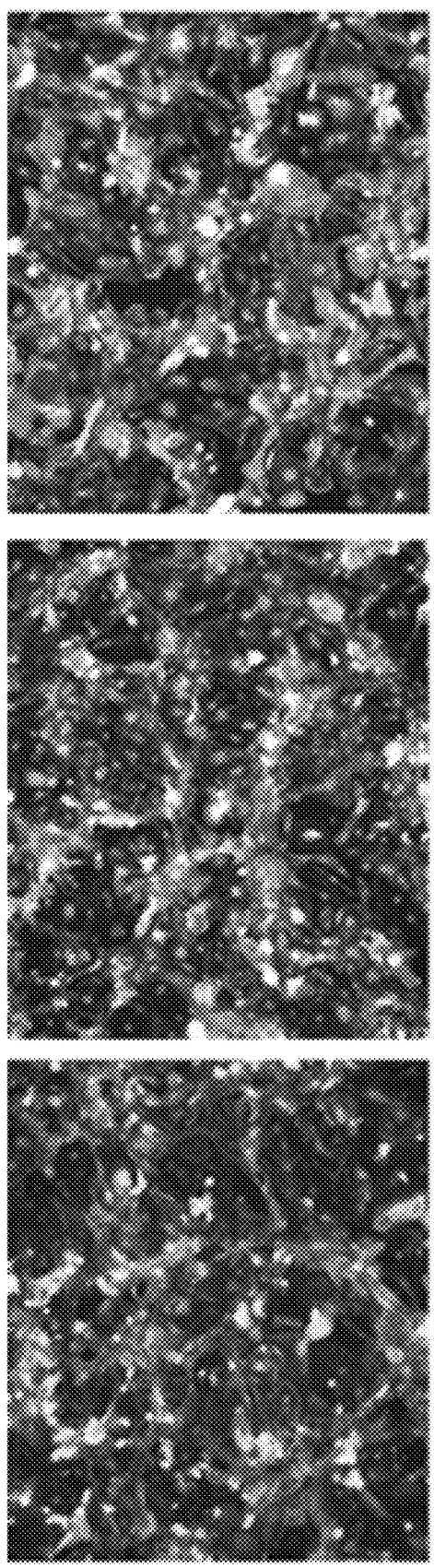
FIG. 8A shows immunofluorescence images of Danon patient iPSC-derived cardiomyocytes transduced with the indicated amounts of AAV9-Luc (Luc), AAV9-wild-type LAMP-2B (LAMP2B v1.0) or AAV9-optimized LAMP-2B (LAMP2B v1.2) vectors.
Figure 8B:
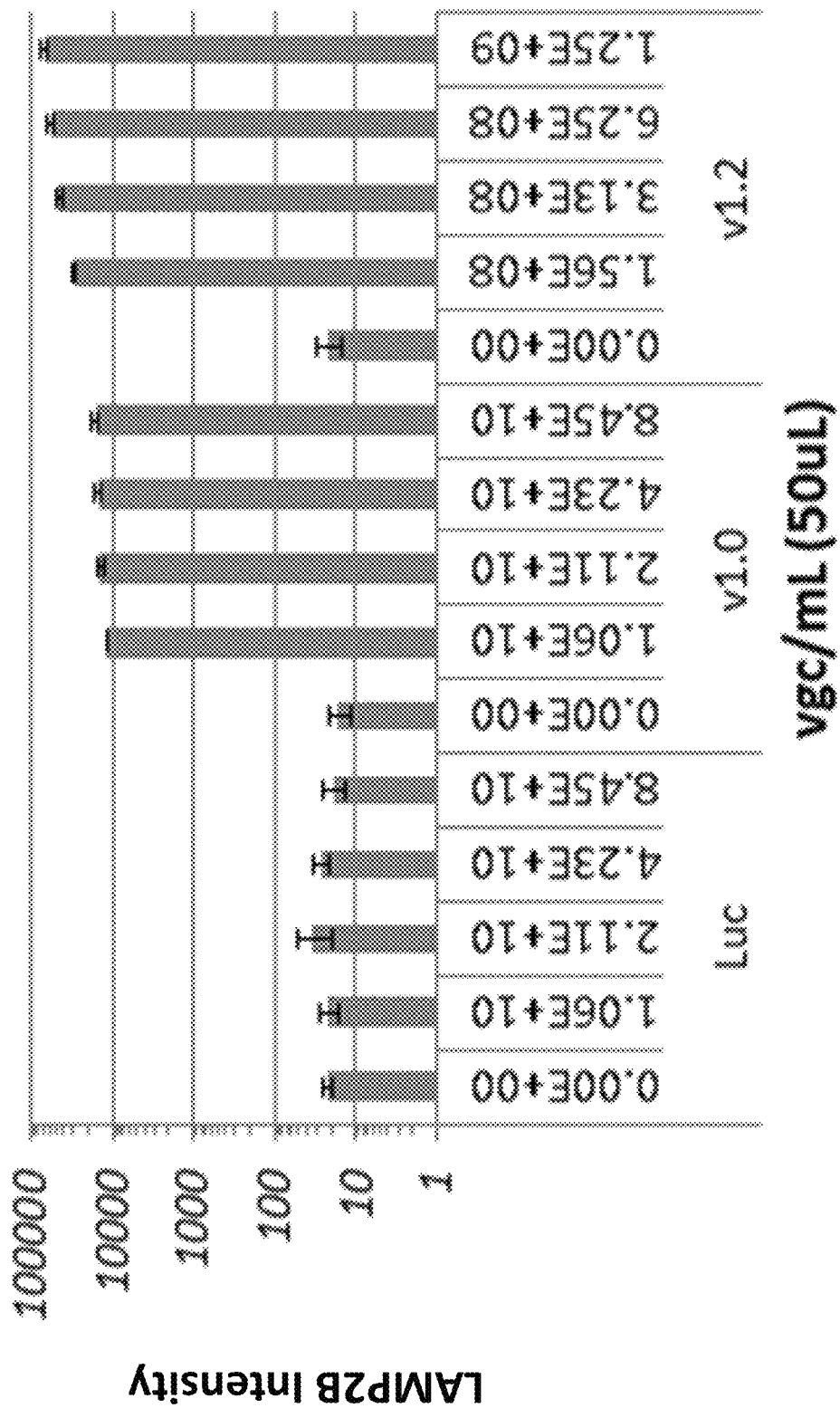
FIG. 8B shows quantification of immunofluorescence of human LAMP-2B protein in Danon patient iPSC-derived cardiomyocytes transduced with AAV9-Luc, AAV9-wild-type LAMP-2B (v1.0) or AAV9-optimized LAMP-2B (v1.2) vectors.

Cardiomyocytes were derived from iPSCs generated from individuals with Danon disease. Following rhythmic contraction and selection for purity, Danon disease cardiomyocytes were transduced with various viral genome copies (vg) of AAV9-Luc (negative control), AAV9-wild-type LAMP-2B.v1.0 or AAV9-optimized LAMP-2B.v1.2. Ten days post-transduction, transduced cardiomyocytes were fixed with 4% paraformaldehyde, permeabilized, blocked for 30 min in 5% IgG-free BSA and incubated for 1 hour with either mouse anti-human LAMP-2B antibody (1:25, clone: H4B4) or rabbit anti-α-actinin antibody (1:200, # A7811, Sigma). Cells were washed with 1×PBS to remove residual unbound primary antibody and then subjected to the appropriate anti-mouse AlexaFluor tagged secondary antibody and 200 ng/mL DAPI for 60 minutes at room temperature. The wells were then washed with PBS prior to imaging. Human LAMP-2B expression was expressed at a higher level in cardiomyocytes transduced with low titer ($1.56\times10^8$ vg/well) AAV9-optimized LAMP-2B.v1.2 vector compared to cardiomyocytes transduced with the highest titer ($8.45\times10^{10}$ vg/well) of AAV9-wild-type LAMP-2B.v1.0 (FIG. 8A and FIG. 8B).

Figure 8C:
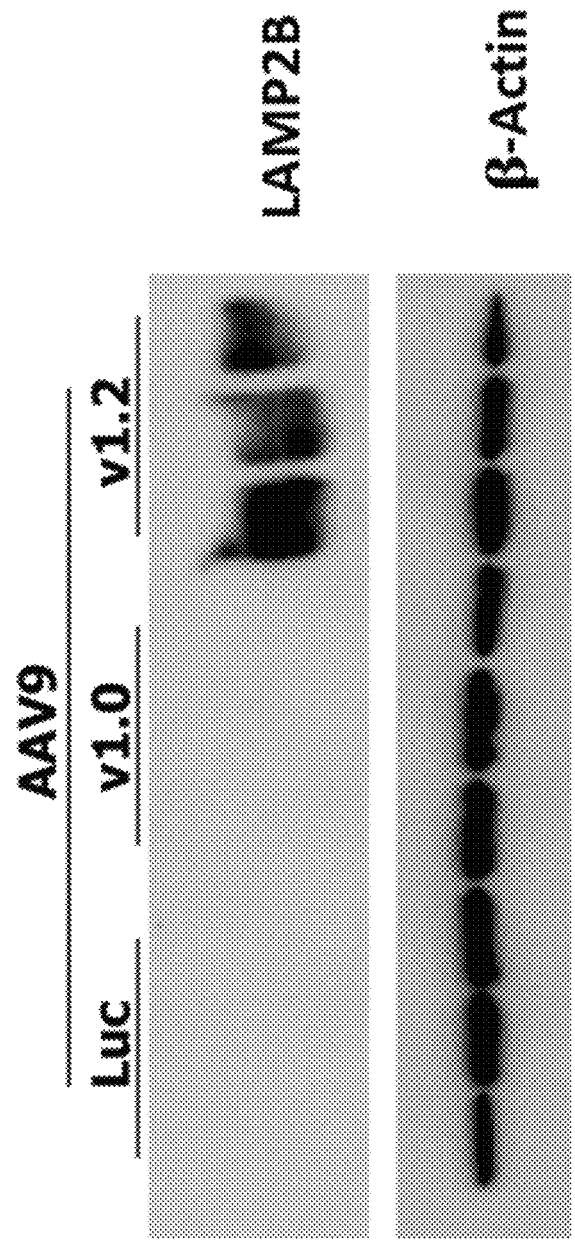
FIG. 8C shows an immunoblot of human LAMP-2B protein in Danon patient iPSC-derived cardiomyocytes transduced with AAV9-Luc, AAV9-wild-type LAMP-2B (v1.0) or AAV9-optimized LAMP-2B (v1.2) vectors.

Western blot analyses were performed on the transduced Danon disease cardiomyocytes. AAV9-optimized LAMP-2B.v1.2 at $0.983\times10^9$ vg/well showed significant expression of LAMP-2B protein compared to no detection of LAMP-2B protein in cells transduced with either AAV9-wild-type LAM2B.v1.0 ($1.347\times10^9$ vg/well) or AAV9-Luc ($1.167\times10^9$ vg/well) vectors (FIG. 8C). Collectively, these results demonstrate that the optimized AAV9-LAMP-2B.v1.2 vector mediates human LAMP-2B expression in Danon disease cardiomyocytes at a significantly higher level than the original AAV9-wild-type LAMP-2B.v1.0 vector.

Example 4: In Vivo Evaluation of AAV9-LAMP-2B.v1.2 in Mouse Model of Danon Disease LAMP-2-deficient mice were intravenously injected with $1\times10^{13}$ vg/kg of AAV9 viral vectors containing original human LAMP-2B (AAV9-LAMP-2B.v1.0), optimized human LAMP-2B (AAV9-LAMP-2B.v1.2, codon variant 1—SEQ ID NO: 3) or vehicle alone. Six weeks post-treatment, mice were sacrificed and heart tissue was collected for analysis of LAMP-2B expression.

Methods

For quantitative analyses of vector copy number, total DNA was isolated from frozen tissues using the DNeasy Blood and Tissue kit according to manufacturer's guidelines. DNA concentration and integrity was assessed spectrophotometrically. qPCR was performed to calculate viral genome copies per μg of DNA using TaqPath ProAmp Master Mix (Applied Biosystems) with forward (5'-ATCATGCTATTGCTTCCCGTA-3; SEQ ID NO: 36) and reverse (5'-GGGCCACAACTCCTCATAAA-3; SEQ ID NO: 37) primers and a probe (5'-CCTCCTTGTATAAATCCTGGTTGCTGTCT-3'; SEQ ID NO: 38) for the WPRE gene. RNase P was used as an endogenous control (Thermofisher, #4403328). A standard curve was generated using a linearized plasmid that contained the vector genome (WPRE) used for virus production. Quantification of DNA per sample was calculated using TaqMan copy number reference assay and was represented as vector copy number per diploid nucleus (VCN/Diploid Nucleus).

RNA was extracted and purified from heart using RNeasy Fibrous Tissue Mini kit according to the manufacturer's protocol. RNA concentration and integrity were assessed spectrophotometrically. RNA was reverse-transcribed using iScript cDNA Synthesis kit and cDNA was used as a template for quantitative real-time (qRT)-PCR. qRT-PCR was performed on cDNA using TaqPath ProAmp Master Mix with forward (5'-ATCATGCTATTGCTTCCCGTA-3'; SEQ ID NO: 36) and reverse (5'-GGGCCACAACTCCTCATAAA-3'; SEQ ID NO: 37) primers and a probe (5'-CCTCCTTGTATAAATCCTGGTTGCTGTCT-3'; SEQ ID NO: 38) for the WPRE gene.

For protein extraction, tissues were flash-frozen and pulverized, and the subsequent tissue powder was digested in protein lysis buffer (100 mM Tris, 300 mM NaCl, 20 mM EDTA, 2% NP-40, 0.2% SDS) containing protease and phosphatase inhibitor cocktails. Partial protein lysates were passed through a glass tissue grinder and sonicated with 3 bursts of 5 second on ice, with 10 seconds intervals in between at 30 amplitude microns power. Samples were centrifuged for 15 min at 12000 rpm and then the supernatant was collected. Concentration of protein in samples was determined by Lowry assay. Proteins (20 μg/sample) were separated using 10-20% SDS-PAGE and transferred to PVDF membranes by rapid dry transfer technique. Membranes were then blocked in 5% milk (non-fat dry milk solubilized in PBS containing 0.1% Tween-20) for 1 h, and incubated with anti-human LAMP-2B (1:100, H4B4), anti-mouse LAMP-2B (1:100) or anti-GAPDH (1:1000, #32233, Santa Cruz) antibodies overnight at 4° C. Membranes were washed and then incubated with the appropriate HRP-conjugated secondary antibodies (1:10,000) for 1 hour at room temperature. The blots were developed using WesternBright™ Sirius substrates followed by imaging on a BioRad gel imager.

For immunofluorescence analyses, tissues were cryoprotected in 30% sucrose/PBS at 4° C., embedded in optimal cutting temperature (OCT) mounting media and then tissue was cut to 8-10 μm thickness on a standard cryotome. Cryosections were then fixed with 4% PFA for 5 min, permeabilized with 0.2% Triton-X for 5 min and blocked with 1% BSA, 3% serum, 1% cold water fish gelatin in PBS for 30 minutes. The sections were incubated with mouse anti-human LAMP-2B antibody (1:50, H4B4) directly conjugated to Alexa Fluor 647 and rabbit anti-dystrophin antibody overnight at 4° C. The slides were then incubated with anti-rabbit Alexa Fluor 488 secondary antibody and DAPI (1:2000, # D9542, Sigma) for 30 min at room temperature. Slides were then imaged using an Olympus FluoView FV1000 confocal microscope. Scan speed, off set, voltage, and gain were kept constant during the acquisition of all images on a given day.

Results

Figure 9B:
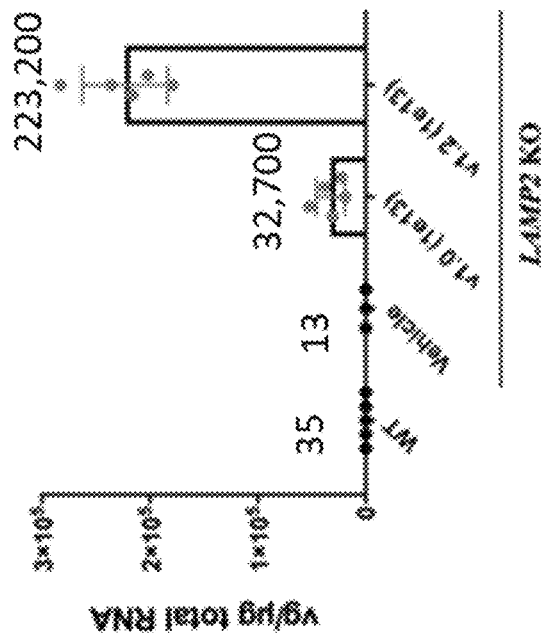
FIG. 9B shows quantitative RT-PCR analyses of transgene mRNA, measured by RT-PCR using probes specific for the WPRE element, in cardiac tissue isolated from LAMP-2-deficient mice treated with AAV9-wild-type LAMP-2B (v1.0), AAV9-optimized LAMP-2B (v1.2) or an AAV9 vehicle control (Vehicle). Expression of mRNA was quantified as vector genomes (vg) per μg total cellular RNA using a standard curve to convert copy number to vector genomes.
Figure 9A:
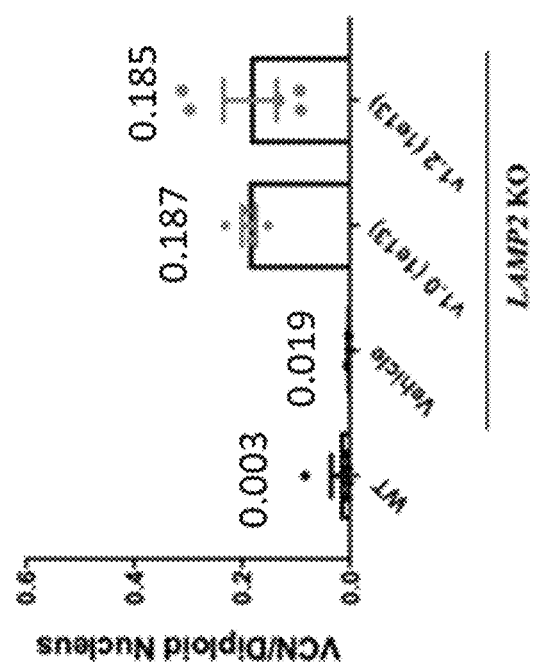
FIG. 9A shows PCR quantification of viral vector DNA in cardiac tissue isolated from LAMP-2-deficient mice treated with AAV9-wild-type LAMP-2B (v1.0), AAV9-optimized LAMP-2B (v1.2) or an AAV9 vehicle control. Vector copy number was quantified as VCN/Diploid Nucleus in the cardiac tissue. Control wild-type mice not injected with vector were included as controls (WT).

Quantitative PCR was performed on cardiac tissue of AAV9-treated LAMP-2-deficient mice. Although similar viral copy numbers were observed in cardiac tissue of mice treated with wild-type and optimized LAMP-2B containing vector (FIG. 9A), transcription of AAV9-optimized LAMP-2B.v1.2 was increased nearly 7-fold compared to the AAV9-wild-type LAMP-2B.v1.0 (FIG. 9B). Despite similar transduction of v1.0 and v1.2 viral vectors in cardiac tissue, induction of human LAMP-2B mRNA expression was significantly enhanced using v1.2.

Figure 9C:
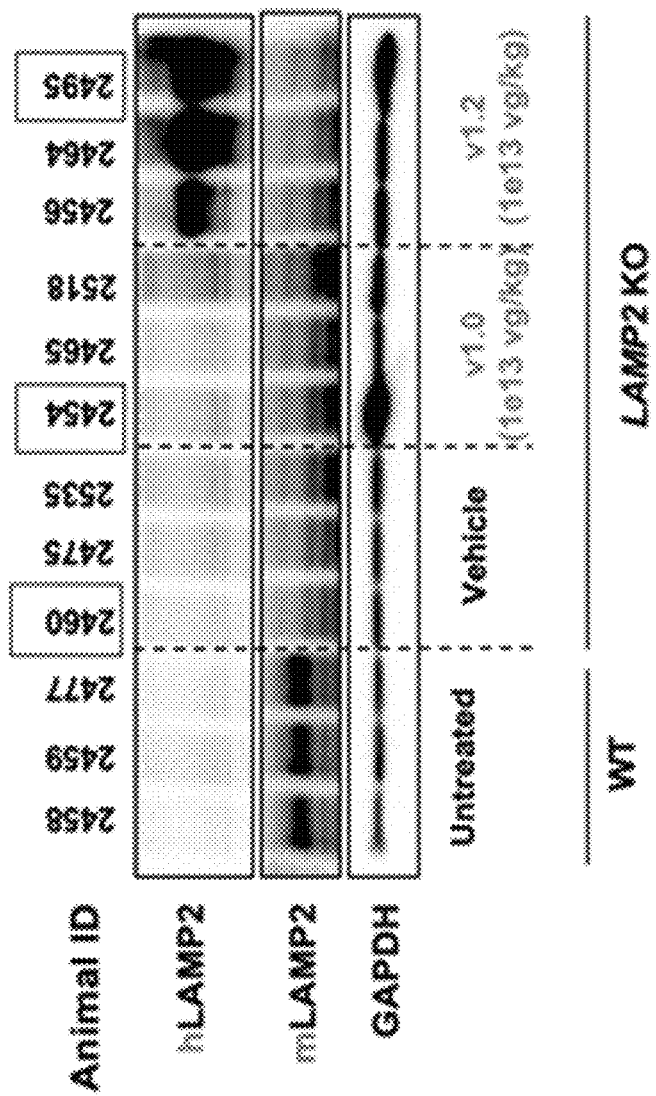
FIG. 9C shows an immunoblot of LAMP-2B protein in cardiac tissue isolated from LAMP-2-deficient mice treated with AA9-wild-type LAMP-2B (v1.0), AAV9-optimized LAMP-2B (v1.2) or the AAV9 vehicle control (Vehicle) compared to untreated wild-type mice (Untreated).
Figure 9D:
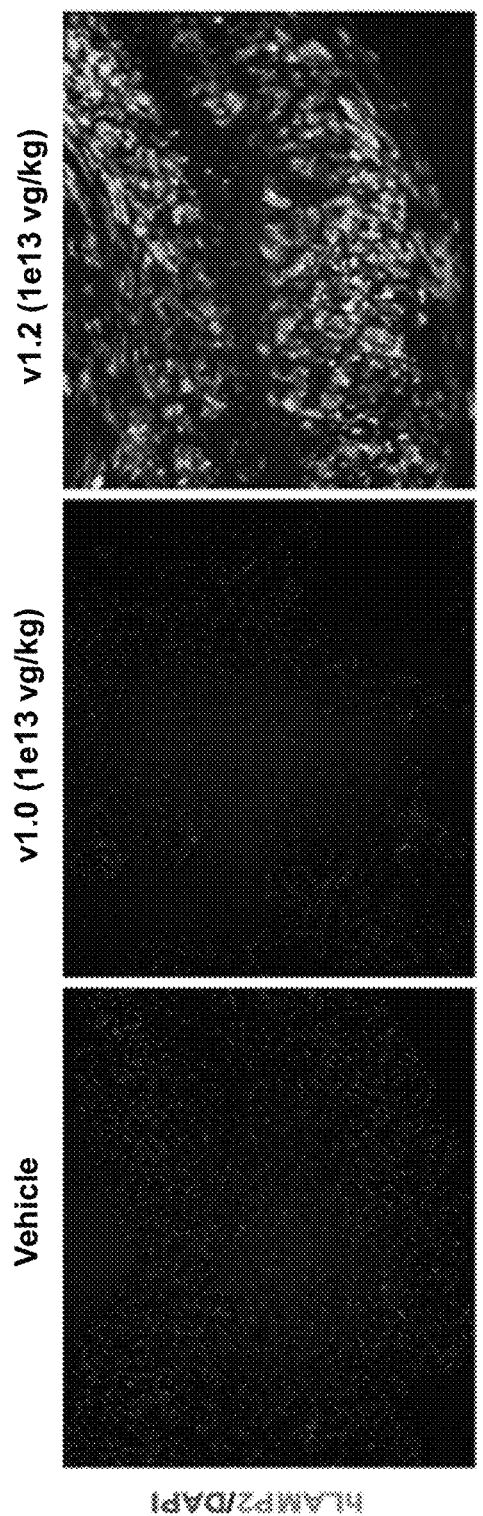
FIG. 9D shows immunofluorescence images of human LAMP-2B protein in cardiac tissue isolated from LAMP-2-deficient mice treated with AAV9-wild-type LAMP-2B (v1.0), AAV9-optimized LAMP-2B (v1.2) or the AAV9 vehicle control.

LAMP-2-deficient mice intravenously injected with AAV9-optimized LAMP-2B.v1.2 vector also showed significantly higher levels of human LAMP-2B protein in cardiac tissue compared to LAMP2-deficient mice treated with AAV9-wild-type LAMP-2B.v1.0 or the vehicle control (FIG. 9C). Similar results were achieved with immunofluorescence staining: human LAMP-2B was highly induced in cardiac tissue of LAMP-2-deficient mice treated with AAV9-optimized LAMP-2B.v1.2 (FIG. 9D). Collectively, these data show that viral transduction using the AAV9-optimized LAMP-2B.v1.2 vector leads to increased expression of human LAMP-2B protein in cardiac tissue in vivo compared to AAV9-wild-type LAMP-2B.v1.0 at the same dose.

Example 4: In Vivo Evaluation of AAV9-LAMP-2B.v1.2 in Non-Human Primates

Non-human primates were intravenously injected with $1 \times 10^{13}$ vg/kg of either the AAV9 viral vector containing codon variant LAMP-2B (v1.2, codon variant 1—SEQ ID NO: 3) described in Example 2, or vehicle control. Eight weeks post-treatment, the non-human primates were humanely sacrificed, and heart, muscle, liver and brain tissue was collected for analysis of LAMP-2B expression.

Methods

For quantitative analyses of vector copy number, total DNA was isolated from frozen tissues using the Qiagen DNeasy kit according to manufacturer's guidelines. DNA concentration and integrity were assessed spectrophotometrically. Quantitative PCR on isolated DNA was performed using TaqMan Universal Master Mix II (Applied Biosystems) with forward (5'-ATCATGCTATTGCTTC-CCGTA-3; SEQ ID NO: 36) and reverse (5'-GGGCCA-CAACTCCTCATAAA-3'; SEQ ID NO: 37) primers and a probe (5'-CCTCCTTGTATAAATCCTGGTTGCTGTCT-3'; SEQ ID NO: 38) for the WPRE gene. RNaseP was used as an endogenous control (#4403328, ThermoFisher). A standard curve was generated using a linearized plasmid that contained the vector genome used for virus production. Quantification of DNA per sample was calculated using the TaqMan copy number reference assay and was represented as vector copy number per diploid nucleus (VCN/Diploid Nucleus).

RNA was extracted and purified from heart and skeletal muscle using the RNeasy Fibrous Tissue Mini kit (Qiagen) and from liver and brain using the RNeasy Lipid Tissue kit (Qiagen) according to manufacturer's protocol. RNA concentration and integrity was assessed using the NanoDrop spectrophotometer. RNA was reverse-transcribed using SuperScript IV VILO master mix (ThermoFisher) and cDNA was used as a template for quantitative real-time (qRT)-PCR. qRT-PCR was performed on cDNA using Taq-Man Universal Master Mix II with forward (5'-ATCATGC-TATTGCTTCCCGTA-3; SEQ ID NO: 36) and reverse (5'-GGGCCACAACTCCTCATAAA-3; SEQ ID NO: 37) and a probe (5'-CCTCCTTGTATAAATCCTGGTTGCTGTCT-3; SEQ ID NO: 38) of the WPRE gene. Human HPRT-1 was used as an endogenous control. A standard curve was generated using a linearized plasmid that contained the vector genome used for virus production.

For semi-quantitative analysis of mRNA using RNAS-cope technology, cardiac tissue was fixed in 10% neutral buffered formalin, embedded in paraffin and sectioned. Transgene mRNA was detected using WPRE-03 probe (#518628, ACD) with RNAscope 2.5 LS RED. Cells with greater than 1 dot were considered positive and the percentage of positive cells were binned into five categories: 0%, 1-25%, 26-50%, 51-75% or 100%.

For western blot analyses, 125 mg of cardiac tissue was homogenized in 500 μL of lysis buffer using the Next Advance Bullet System. Protein concentration was determined using the BCA kit (ThermoFisher) and proteins (50 μg/sample) were separated using SDS-PAGE and then transferred to nitrocellulose membranes. Membranes were then probed with mouse anti-human LAMP2 (1:100), washed and then incubated with HRP-conjugated anti-mouse antibody. The blots were developed using ECL substrate and the BioRad ChemiDoc MP system.

For the LAMP-2B ELISA, protein extraction was performed as described above. A plate was coated with mouse anti-LAMP2 antibody (clone: H4B4, # NBP2-22217, Novus Biologicals), 100 μg of tissue lysate was added to each well, and detection was performed using anti-LAMP2 polyclonal antibody (# AF6228, R&D Systems) followed by incubation with HRP-conjugated donkey anti-goat antibody (# AP180P, Millipore).

Results

Figure 10B:
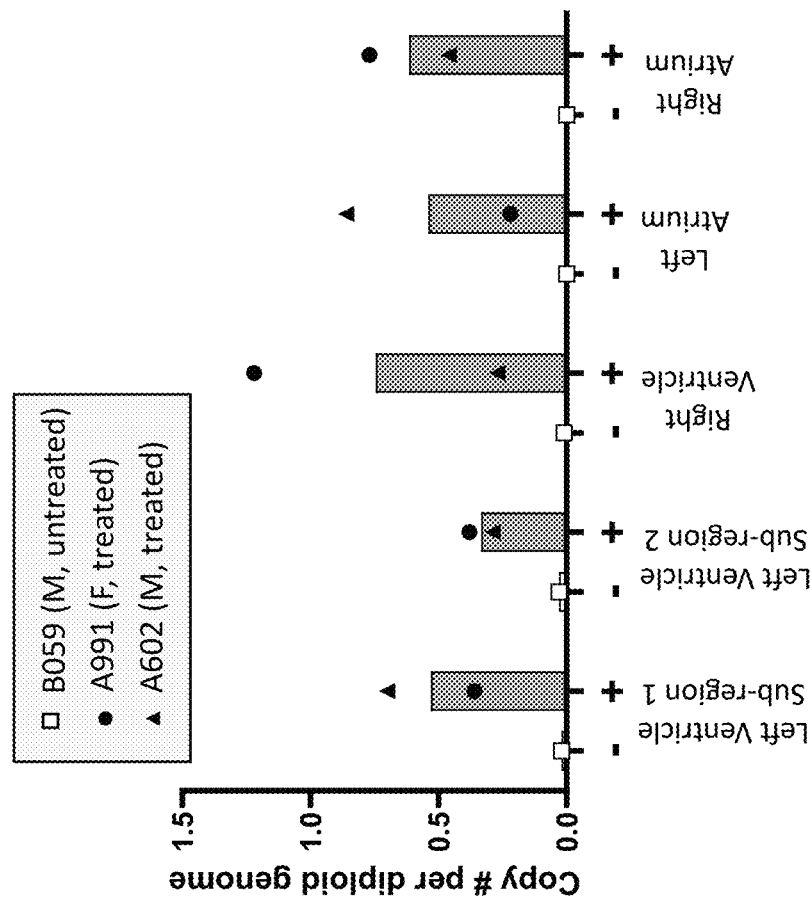
FIG. 10B shows PCR quantification of viral vector DNA in cardiac chambers isolated from primates treated with AAV9-optimized human LAMP-2B vector (treated) or no vector vehicle control (untreated). Individuals are denoted as B059 (male, M), A991 (female, F), and A602 (male, M).
Figure 10A:
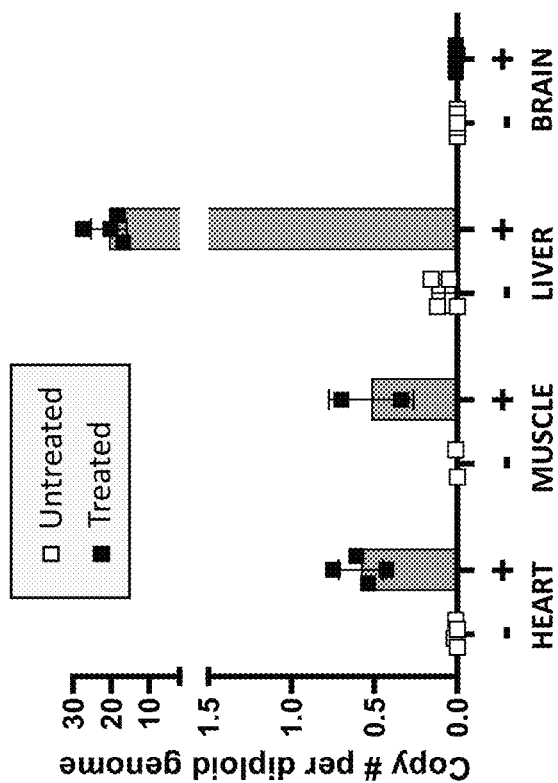
FIG. 10A shows PCR quantification of viral vector DNA in heart, muscle, liver and brain tissue isolated from primates treated with the AAV9-optimized human LAMP-2B (treated) vector or no vector vehicle control (untreated). Individuals are denoted as black or white squares.
Figure 10C:
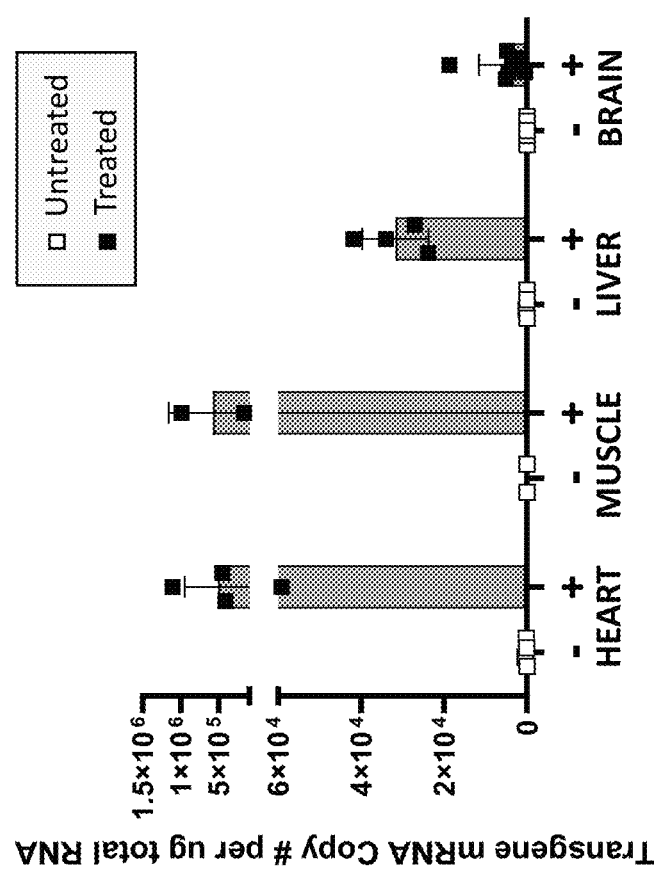
FIG. 10C shows quantitative RT-PCR analyses of transgene mRNA, measured by RT-PCR using probes specific for the WPRE element, in heart, muscle, liver and brain tissue isolated from primates treated with the AAV9-optimized human LAMP-2B vector (treated) or no vector vehicle control (untreated).
Figure 10D:
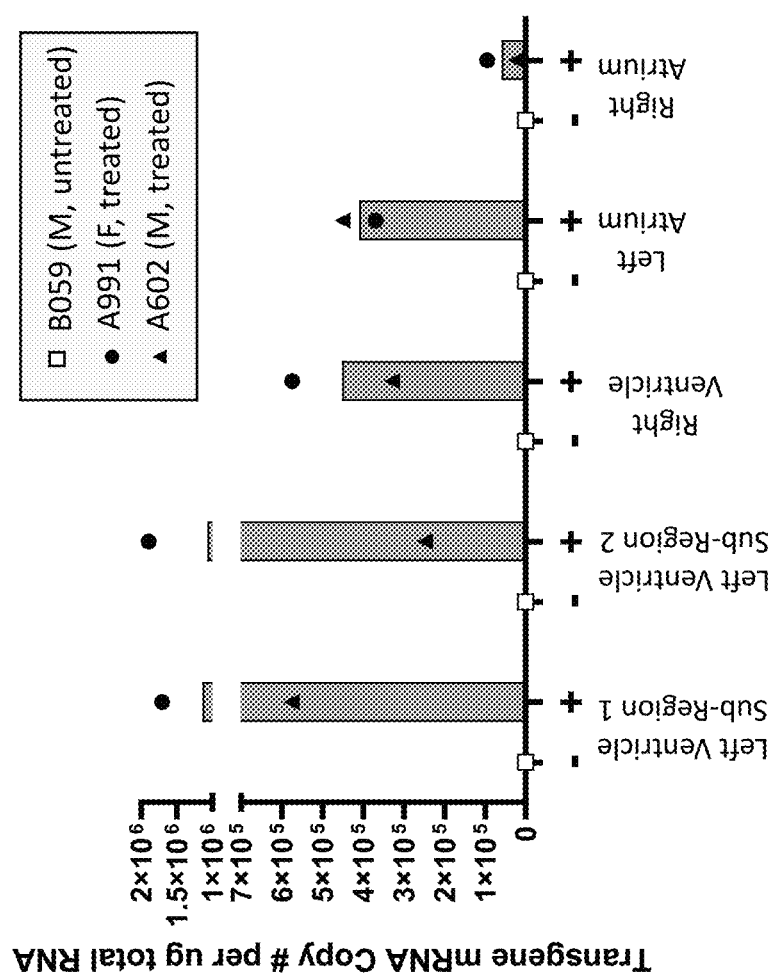
FIG. 10D shows quantitative RT-PCR analyses of transgene mRNA in cardiac chambers isolated from primates injected with the AAV9-optimized human LAMP-2B vector (treated) or no vector vehicle control (untreated).

Quantitative PCR was performed on various tissues of AAV9-treated primates. Viral copy numbers were increased in heart, muscle and liver tissue of primates injected with AAV9-LAMP-2B.v1.2 vector at $1 \times 10^{13}$ vg/kg compared to vehicle control (FIG. 10A). Vector genomes were detected in all cardiac chambers examined, including the left and right ventricles and left and right atriums (FIG. 10B). Vector mRNA was detected at significant levels in the heart, skeletal muscle and liver tissue of treated primates compared to the untreated vehicle control (FIG. 10C and FIG. 10D). In situ RNA analysis showed approximately 25-75% of heart and liver tissue expressing vector mRNA (FIG. 10E and FIG. 10F). These data demonstrate that systemic administration of $1 \times 10^{13}$ vg/kg AAV9-optimized LAMP-2B.v1.2 to a primate results in efficient transduction and expression in heart tissue in vivo.

Figure 10H:
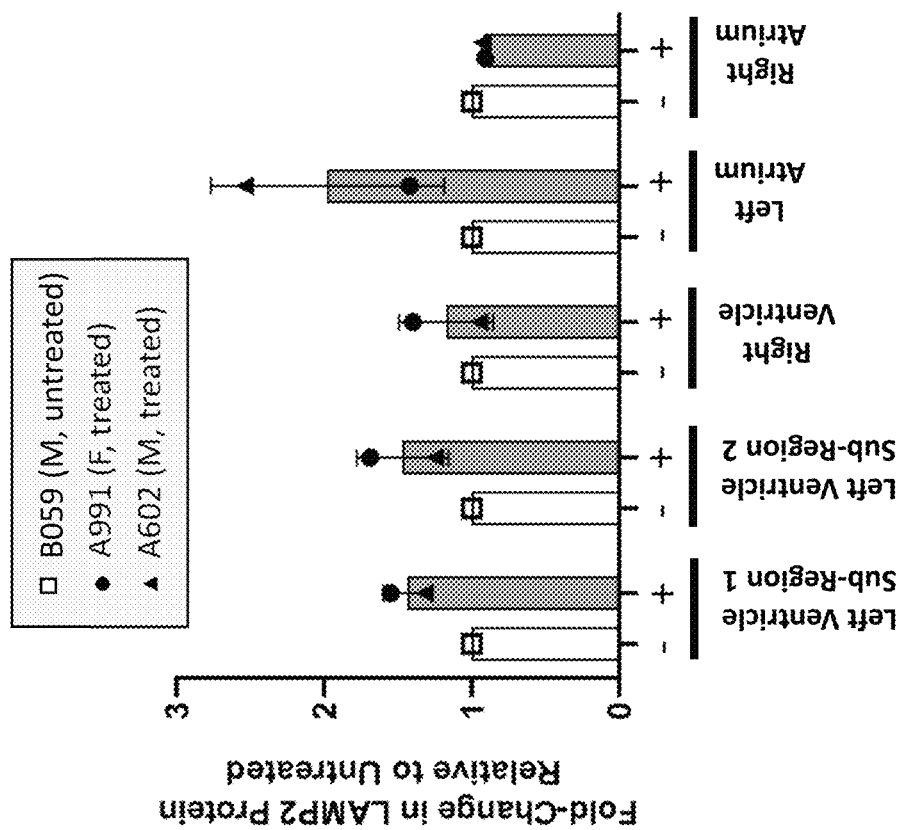
FIG. 10H shows fold change of LAMP-2B protein assessed by western blot in cardiac chambers isolated from primates treated with the AAV9-optimized human LAMP-2B vector relative to no vector (untreated).
Figure 10G:
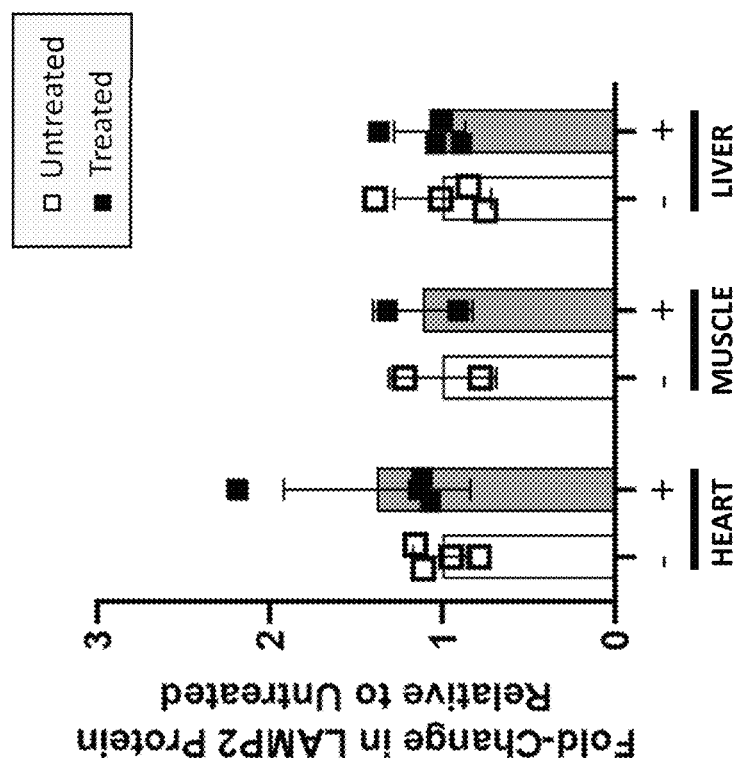
FIG. 10G shows fold change of LAMP-2B protein assessed by western blot in heart, muscle and liver tissue isolated from primates treated with the AAV9-optimized human LAMP-2B vector relative to no vector (untreated).
Figure 10J:
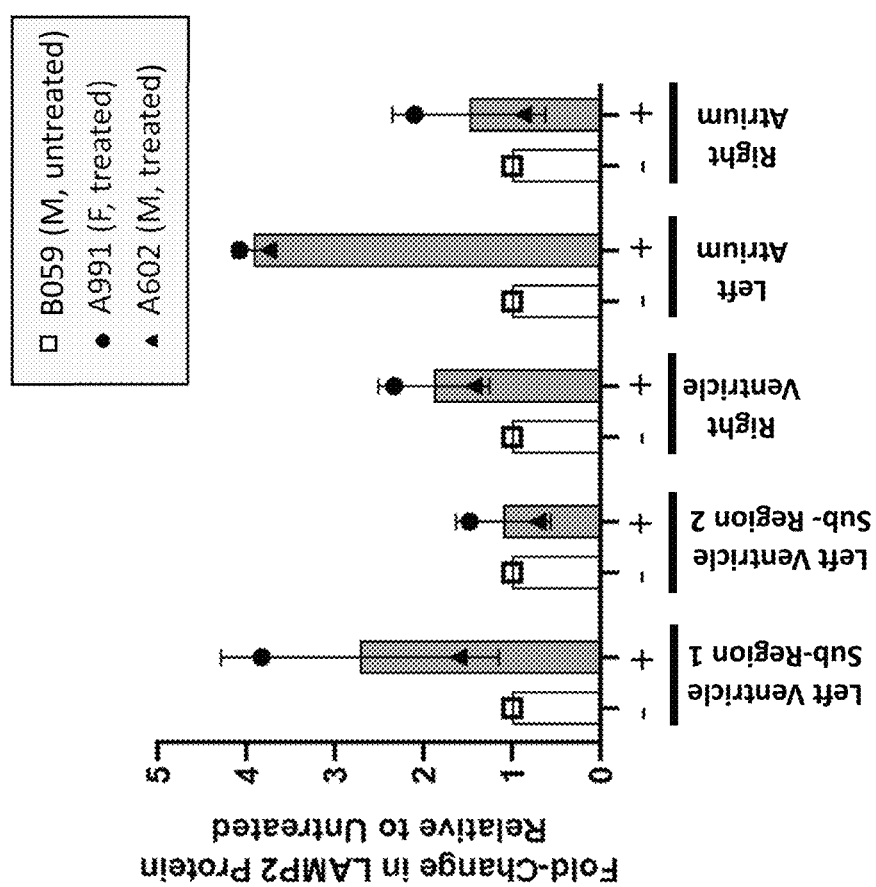
FIG. 10J shows quantification of LAMP-2B protein by ELISA in cardiac chambers isolated from primates treated with the AAV9-optimized human LAMP-2B vector relative to no vector (untreated).
Figure 10I:
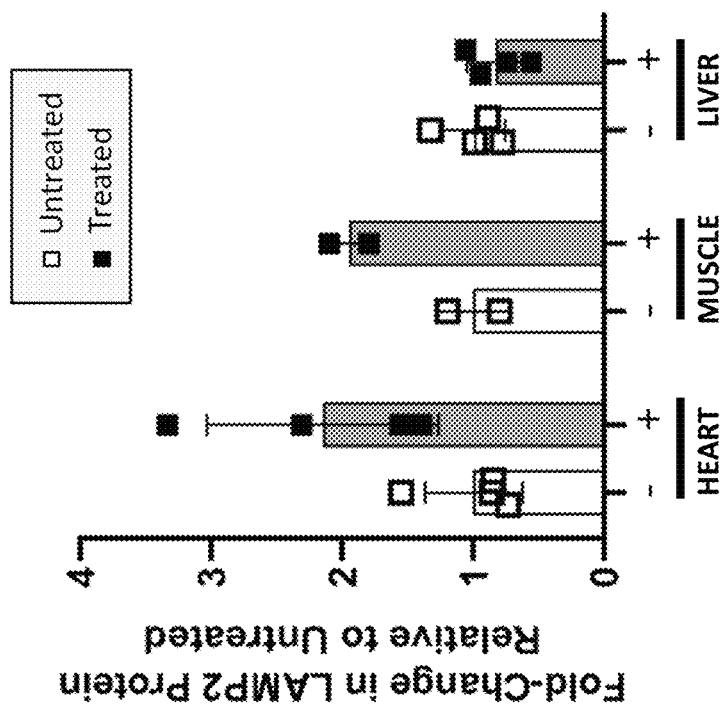
FIG. 10I shows quantification of LAMP-2B protein by ELISA in heart, muscle and liver tissue isolated from primates treated with the AAV9-optimized human LAMP-2B vector relative to no vector (untreated).

Western blot analyses showed that primates systemically treated with LAMP-2B.v1.2 at $1 \times 10^{13}$ vg/kg showed increased human LAMP-2B protein in the left and right ventricles and left atrium of the heart compared to an untreated control (FIG. 10G and FIG. 10H). ELISA also showed that human LAMP-2B protein was increased in the left ventricle and atrium of the heart, as well as skeletal muscle tissue of primates treated with AAV9-LAMP-2B.v1.2 vector compared to an untreated control (FIG. 10I and FIG. 10J). Vector transduction using AAV9.LAMP-2B.v1.2 leads to expression of human LAMP-2B protein in cardiac tissue of primates in vivo.

What is claimed is:

1. An adeno-associated virus (AAV) vector, comprising an expression cassette comprising a polynucleotide sequence that encodes a LAMP-2B protein, operatively linked to a promoter, wherein the polynucleotide sequence comprises any one of SEQ ID NOs: 3-5.

2. The AAV vector of claim 1, wherein the LAMP-2B protein comprises SEQ ID NO: 1.

3. The AAV vector of claim 1, wherein the polynucleotide sequence comprises SEQ ID NO: 3.

4. The AAV vector of claim 1, wherein the polynucleotide sequence comprises SEQ ID NO: 4.

5. The AAV vector of claim 1, wherein the polynucleotide sequence comprises SEQ ID NO: 5.

6. The AAV vector of claim 1, wherein the promoter is a CAG promoter.

7. The AAV vector of claim 1, wherein the promoter comprises an enhancer/promoter region that shares at least 95% identity to SEQ. ID NO: 22.

8. The AAV vector of claim 7, wherein the enhancer/promoter region comprises SEQ ID NO: 22.

9. The AAV vector of claim 1, wherein the expression cassette comprises, in 5' to 3' order:
  (a) an enhancer/promoter region that comprises SEQ. ID NO: 22;
  (b) the polynucleotide sequence that encodes the LAMP-2B protein, wherein the polynucleotide sequence comprises SEQ ID NO: 3;
  (c) a 3' UTR sequence that comprises SEQ ID NO: 27; and
  (d) a poly-adenylation sequence that comprises SEQ ID NO: 7.

10. The AAV vector of claim 9, wherein the expression cassette is flanked by (i) a 5' ITR that comprises SEQ ID NO: 11 and (ii) a 3' ITR that comprises SEQ ID NO: 12.

11. The AAV vector of claim 9, wherein the expression cassette comprises SEQ ID NO: 8.

12. The AAV vector of claim 1, wherein the AAV vector comprises an AAV9 capsid.

13. The AAV vector of claim 12, wherein the AAV9 capsid comprises one or more capsid proteins that comprise amino acids 1 to 736 of SEQ ID NO: 27; amino acids 138 to 736 of SEQ ID NO: 27; or amino acids 203 to 736 of SEQ ID NO: 27.

14. A polynucleotide sequence comprising any one of SEQ ID NOs: 3-5.

15. The polynucleotide sequence of claim 14, comprising SEQ ID NO: 3.

* * * * *